(12) United States Patent
Carroll

(10) Patent No.: US 6,602,851 B1
(45) Date of Patent: Aug. 5, 2003

(54) SMDF AND GGF NEUREGULIN SPLICE VARIANT ISOFORMS AND USES THEREOF

(75) Inventor: Steven L. Carroll, Homewood, AL (US)

(73) Assignee: UAB Research Foundation, Birmingham, AL (US)

( * ) Notice: Subject to any disclaimer, the term of this patent is extended or adjusted under 35 U.S.C. 154(b) by 214 days.

(21) Appl. No.: 09/684,708

(22) Filed: Oct. 6, 2000

Related U.S. Application Data

(60) Provisional application No. 60/158,622, filed on Oct. 8, 1999.

(51) Int. Cl.[7] ............... A61K 38/18; C07K 14/475
(52) U.S. Cl. ................. 514/12; 514/903; 530/350
(58) Field of Search ............... 514/12, 903; 530/350

(56) References Cited

U.S. PATENT DOCUMENTS 6,284,535 B1 * 9/2001 Role

\* cited by examiner

Primary Examiner—Gary Kunz
Assistant Examiner—Stephen Gucker
(74) Attorney, Agent, or Firm—Benjamin Aaron Adler

(57) ABSTRACT

Distinct cDNAs encoding six cysteine-rich domain-NRGs and four glial growth factor isoforms were identified and sequenced. Additional heterogeneity is found in the EGF-like (α- and β-isoforms) and carboxy terminal (a and b variant) regions of CRD-NRGs. Furthermore, the predicted GGF proteins contain glycosylation domains previously found only in mesenchymal NRGs. GGF mRNAs accumulate in axotomized nerve, a subpopulation of DRG neurons and most spinal cord motoneurons. CRD-NRGs, however, are undetectable in injured nerve except by RT-PCR. In contrast, the majority of DRG and spinal cord motor neurons express CRD-NRGs, with a β1 isoform being most abundant and at least some of these proteins are secreted in a form capable of activating erbB receptors. Thus, GGF and CRD-NRG subfamilies are more structurally diverse than previously appreciated. NRG actions during Wallerian degeneration may be modulated by the action of distinct splice variants.

6 Claims, 27 Drawing Sheets

| | |
|---|---|
| GAATTCGGCACGAGGCGATGCTCAGAGGGCAGGCACCTGCTGCTCTGTAA | 50 |
| TGATTCAGCCTCTTTCAGCCGCTGCGTTAACACGACAGGATGCTGTTGCT | 100 |
| ACTGTCGCTGCTGCCTCTCCTGCCGCCGCCGCTGCTGCCGCCGCCGCCTC | 150 |
| CTCTGGTCTTGCTTTTGCTTTTACTTCTCCTGCATGACAGTTGTTTTCTT | 200 |
| CCTCTAAGCAGACACCAGCTTCAGACGCTTGAGGTGAGAAACATGCCTTT | 250 |
| CAGTTTGGGATACTGGTTTACTTAATCGGCTAGGCGGCAGCTTGCTTCCT | 300 |
| ATTTTGGTCCCCTGCCTTCTTGACCAACCCGGCATGGTTTGGAGAAGCAT | 350 |
| TTGAAAGAACTGAAAAGTGTCCCAGAAACAACAGCTCAAGATATTTCGG | 400 |
| TACACTTCTATTTCATAGTTGCTAGAAGCCCTTTCTTTTTCGTTTTTTTT | 450 |
| TTCTTTTTCTTTTTCTTTTTCTTTTTCCTTTTCCTGCTTCCTCCTAAGCT | 500 |
| CTGGTACTTTGGGTAATTGCCTTGGACTTGGGTGCCTTATCGATTTCCCC | 550 |
| CTCCAAGATGCTGTATCATTTGGTTGGGGGGAGCTCTGCGTGGTAATGCA | 600 |
| CTGTGAGAGAGGCCAGGCCTTCTGGAGGTGAGCCGATGGAGATTTATTCC | 650 |

```
                                             M  E  I  Y  S      5
CCAGACATGTCTGAGGTAGCTGGCGGGAGGTCCTCCAGCCCCTCCACTCA             700
  P  D  M  S  E  V  A  G  G  R  S  S  S  P  S  T  Q           22
GCTGAGTGCAGCCCCATCTCTTGATGGCTTCCGGCAGCGGAGGAACATA             750
  L  S  A  A  P  S  L  D  G  L  P  A  A  E  E  H              38
TACCAGACACCCACACAGAAGATGAGAGAAGCCCTGGACTCCTGGGCCTG            800
  I  P  D  T  H  T  E  D  E  R  S  P  G  L  L  G  L           55
```

Fig. 1A

```
GCGGTGCCCTGCTGTGTGTGCCTGGAAGCTGAGCGCCTGAGAGGGTGTCT    850
  A   V   P   C   C   V   L   E   A   E   R   L   R   G   C   L     72
CAACTCCGAGAAGATCTGCATTGTTCCCATTCTGGCTTGCCTAGTCAGCC    900
  N   S   E   K   I   C   I   V   P   I   L   A   C   L   V   S     88
TCTGCCTCTGCATTGCTGGCCTGAAGTGGGTATTTGTGGACAAGATATTT    950
  L   C   L   C   I   A   G   L   K   W   V   F   V   D   K   I   F    105
GAATACGACTCTCCTACCCACCTTGACCCTGGGGGGTTAGGCCAGGACCC   1000
  E   Y   D   S   P   T   H   L   D   P   G   G   L   G   Q   D   P    122
TGTGATTTCTCTGGATCCAACTGCTGCCCCAGCCATTTTGGTATCATCTG   1050
  V   I   S   L   D   P   T   A   A   P   A   I   L   V   S   S      138
AGGCATACACTTCACCTGTCTCTAAGGCTCAGTCTGAAGCTGGGGCTCAT   1100
  E   A   Y   T   S   P   V   S   K   A   Q   S   E   A   G   A   H    155
```

SMDF amino
```
GTTACAGTACAAGGTGACCATGCTGCTGTGGCCTCTGAACCTTCAGCAGT   1150
  V   T   V   Q   G   D   H   A   A   V   A   S   E   P   S   A   V    172
ACCGACCCGGAAGAACCGGCTGTCTGCTTTTCCTCCCTTTCACTCTACTG   1200
  P   T   R   K   N   R   L   S   A   F   P   P   F   H   S   T      188
CACCGCCCTTCCCTTCTCCAGCTCGGACCCCTGAGGTGAGAACACCCAAG   1250
  A   P   P   F   P   S   P   A   R   T   P   E   V   R   T   P   K    205
TCAGGAACTCAGCCACAAACAACAGAAACTAACCTGCAAACTGCTCCTAA   1300
  S   G   T   Q   P   Q   T   T   E   T   N   L   Q   T   A   P   K    222
ACTTTCCACATCGACATCCACGACTGGGACCAGCCATCTCATAAAGTGCG   1350
  L   S   T   S   T   S   T   T   G   T   S   H   L   I   K   C      238
CGGAGAAGGAGAAAACTTTCTGTGTGAATGGGGGCGAGTGCTTCACGGTG   1400
  A   E   K   E   K   T   F   C   V   N   G   G   E   C   F   T   V    255
```

EGF-like Common
```
AAGGACCTGTCAAACCCGTCAAGATACTTGTGCAAGTGCCCAAATGAGTT   1450
  K   D   L   S   N   P   S   R   Y   L   C   K   C   P   N   E   F    272
```

Fig. 1B

```
TACTGGTGATCGTTGCCAAAACTACGTAATGGCCAGCTTCTACAAGCATC  1500
  T  G  D  R  C  D  N  Y  V  M  A  S  F  Y  K  H    288
TTGGGATTGAATTTATGGAAGCGGAGGAACTCTACCAGAAGAGGGTGCTG  1550
  L  G  I  E  F  M  E  A  E  E  L  Y  Q  K  R  V  L  305
              1                        TM
ACAATTACTGGCATCTGTATCGCCCTGCTGGTGGTCGGCATCATGTGTGT  1600
  T  I  I  G  I  C  I  A  L  L  V  V  G  I  M  C  V  322
GGTGGCCTACTGCAAAACCAAGAAGCAGCGGCAGAAGCTTCATGATCGGC  1650
  V  A  Y  C  K  T  K  K  Q  R  Q  K  L  H  D  R    338
TTCGGCAGAGTCTTCGGTCAGAACGGAGCAACCTGGTGAACATAGCGAAT  1700
  L  R  Q  S  L  R  S  E  R  S  N  L  V  N  I  A  N  355
GGGCCTCACCACCCAAACCCGCCGCCAGAGAACGTGCAGCTGGTGAATCA  1750
  G  P  H  H  P  N  P  P  P  E  N  V  Q  L  V  N  C  372
ATACGTATCTAAAAACGTCATCTCCAGTGAGCATATTGTTGAGAGAGAAG  1800
  Y  V  S  K  N  V  I  S  S  F  H  I  V  E  R  E    390
TGGAGACTTCCTTTTCCACCAGTCATTACACTTCCACAGCCCATCACTCC  1850
  V  E  T  S  F  S  T  S  H  Y  T  S  T  A  H  H  S  405
ACGACTGTCACCCAGACTCCTAGTCACAGCTGGAGTAATGGGCACACGGA  1900
                                              Common
  T  T  V  T  Q  T  P  S  H  S  W  S  N  G  H  T  E  422
Carboxy
GAGCGTCATTTCAGAAAGCAACTCCGTAATCATGATGTCTTCGGTAGAGA  1950
  S  V  I  S  E  S  N  S  V  I  M  M  S  S  V  E    438
ACAGCAGGCACAGCAGTCCCGCCGGGGGCCCACGAGGACGTCTTCATGGC  2000
  N  S  R  H  S  S  P  A  G  G  F  R  G  R  L  H  G  455
CTGGGAGGCCCTCGTGATAACAGCTTCCTCAGGCATGCCAGAGAAACCCC  2050
  L  G  G  P  R  D  N  S  F  I  R  H  A  R  E  T  P  472
TGACTCCTACAGAGACTCTCCTCATAGCGAAAGGTATGTATCAGCCATGA  2100
  D  S  Y  R  D  S  P  H  S  E  R  Y  V  S  A  M    488
CCACCCCGGCTCGTATGTCACCTGTAGATTTCCACACGCCAAGCTCCCCT  2150
  T  T  P  A  R  M  S  P  V  D  F  H  T  P  S  S  P  505
```

Fig. 1C

```
AAATCGCCCCCTTCGGAAATGTCTCCACCCGTGTCCAGCATGACGGTGTC  2200
 K   S   P   P   S   E   M   S   P   P | V   S   S   M   T   V   S    522
CATGCCCTCTGTGGCAGTCAGCCCCTTTGTGGAAGAAGAGAGGCCTCTGC  2250
   M   P   S   V   A   V   S   P   F   V   E   E   E   R   P   L      538
TGCTTGTGACGCCACCAAGGCTACGGGAGAAGAAATATGATCATCACCCC  2300
 L   L   V   T   P   P   R   L   R   E   K   K   Y   D   H   H   P    555
CAGCAACTCAACTCCTTTCATCACAACCCTGCACATCAGAGTACCAGCCT  2350
 C   C   L   N   S   F   H   H   N   P   A   H   Q   S   T   S   L    572
                                                    "a" Variant
CCCCCCTAGCCCACTGAGGATAGTGGAGGATGAGGAGTACGAGACGACCC  2400
   P   P   S   P   L   R   I   V   E   D   E   E   Y   E   T   T      588
```
Carboxy Terminus
```
AGGAGTATGAGTCAGTTCAAGAGCCCGTTAAGAAAGTCACCAATAGCCGG  2450
 Q   E   Y   E   S   V   Q   E   P   V   K   K   V   T   N   S   R    605
CGGGCCAAAAGAACCAAGCCCAATGGCCACATTGCCAATAGGTTGGAAAT  2500
   R   A   K   R   T   K   P   N   G   H   I   A   N   R   L   E   M  622
GGACAGCAACACAAGTTCTGTGAGCAGTAACTCAGAAAGTGAGACAGAAG  2550
   D   S   N   T   S   S   V   S   S   N   S   E   S   E   T   E      638
ACGAAAGAGTAGGTGAAGACACACCATTCCTGGGCATACAGAACCCCCTG  2600
   D   E   R   V   G   E   D   T   P   F   L   G   I   D   N   P   L  655
GCAGCCAGCCTTGAGGTGGCCCCCGCCTTCCGTCTGGCTGAGAGCAGGAC  2650
   A   A   S   L   E   V   A   P   A   F   R   L   A   E   S   R   T  672
TAACCCAGCAGGCCGCTTCTCCACACAGGAGGAATTACAGGCCAGGCTGT  2700
   N   P   A   G   R   F   S   T   Q   E   E   L   Q   A   R   L      688
CTAGTGTAATCGCTAACCAAGACCCTATTGCTGTATAAAACCTAAATAAA  2750
 S   S   V   I   A   N   Q   D   P   I   A   V         (SEQ ID NO. 2) 700
CACATAGATTCACCTGTAAAACTTTATTTTATATAATAAAGTATTTCACC  2800

TTAAATTAAACAATTTATTTTATTTTAGCAGTTCTGCAAATACTCGTGCC  2850

GAATTC          (SEQ ID NO. 1)                      2856
```

Fig. 1D

```
Rat      1   MEIYSPDMSEVAGGRSSSPSTQLSAAPSLDGLPAAEEHIPDTHTEDERSPGLLGLAVPCCVCLEAERLRGCLNSEKICIV
Human    1   MEIYSPDMSEVAAERSSSPSTQLSADPSLDGLPAAED-MPEPQTEDGRTPGLVGLAVPCCACLEAERLRGCLNSEKICIV
                ** ***     ***      *** ***     ***      *** *****************

Rat     81   PILACLVSLCLCIAGLKWVFVDKIFEYDSPTHLDPGGLGQDPVISLDPTAAPAILVSSEAYTSPVSKAQSEAGAHVTVQG
Human   80   PILACLVSLCLCIAGLKWVFVDKIFEYDSPTHLDPGGLGQDPIISLDATAASAVWSSEAYTSPVSRAQSESEVQVTVQG
             ****************************************** ****  **** * ********* **** * * ****

Rat    161   DHAAVASEPSAVPTRKNRLSAFPPFHSTAPPFPSPARTPEVRTPKSGTQPQTTETNLQTAPKL STSTSTTGTSHLIKCAE
Human  160   DKAVVSFEPSAAPTPKNRIFAFSFLPSTAPSFPSPTRNPEVRTPKSATQPQTTETNLQTAPKL STSTSTTGTSHLVKCAE
             * * ** ***  * *** ** * * ***** ****  ********  **************  ************ ****

Rat    241   KEKTFCVNGGECFTVKDLSNPSRYLCKCPNEFTGDRCQNYVMASFYKHLGIEFME--AEELYQKRVLTITGICIALLVVG
Human  240   KEKTFCVNGGECFMVKDFMVKDLSNPSRYLCKCPNEFTGDRCQNYVMASFYSTSTPFLSLPE      (SEQ ID NO. 3)
             *************                                     ***********

Rat    319   IMCVVAYCKTKKQRQKLHDRLRQSLRSERSNLVNIANGPHHPNPPPENVQLVNQYVSKNVISSEHIVEREVETSFSTSHY

Rat    399   TSTAHHSTVTVQTPSHSWSNGHTESVISESNSVIMMSSVENSRHSSPAGGPRGRLHGLGGPRDNSFLRHARETPDSYRDS

Rat    479   PHSERYVSAMTTPARMSPVDFHTPSSPKSPPSEMSPPVSSMTVSMPSVAVSPFVEEERPLLLVTPPRLREKKYDHHPQQL

Rat    559   NSFHHNPAHQSTSLPPSPLRIVEDEEYETTQEYESVQEPVKKVTNSRRAKRTKPNGHIANRLEMDSNTSSVSSNSESETE

Rat    639   DERVGEDTPFLGIQNPLAASLEVAPAFRLAESRTNPAGRFSTQEELQARLSSVIANQDPIAV    (SEQ ID NO. 2)
```

Fig. 2

| | |
|---|---|
| GAATTCGGCACGAGGCGGCAGCTTGCTTCCTATTTTGGTCCCCTGCCTTC | 50 |
| TTGACCAACCCGGCATGGTTTGGAGAAGCATTTGAAAGAACTGAAAAAGT | 100 |
| GTCCCAGAAACAACAGCTCAAGATATTTCGGTACACTTCTATTTCATAGT | 150 |
| TGCTAGAAGCCCTTTCTTTTTTCGTTTTTTTTTTTCTTTTTCTTTTTCT | 200 |
| TTTTCTTTTTCCTTTTCCTGCTTCCTCCTAAGCTCTGGTACTTTGGGTAA | 250 |
| TTGCCTTGGACTTGGGTGCCTTATCGATTTCCCCCTCCAAGATGCTGTAT | 300 |
| CATTTGGTTGGGGGGAGCTCTGCGTGGTAATGCACTGTGAGAGAGGCCAG | 350 |
| GCCTTCTGGAGGTGAGCCGATGGAGATTTATTCCCCAGACATGTCTGAGG | 400 |

```
                           M  E  I  Y  S  P  D  M  S  E     10
TAGCTGGCGGGAGGTCCTCCAGCCCCTCCACTCAGCTGAGTGCAGTTCCA         450
 V  A  G  G  R  S  S  S  P  S  T  Q  L  S  A  V  P         27
TCTCTTGATGGCTTCCGGCAGCGGAGGAACATATACCAGACACCCACAC          500
 S  L  D  G  L  P  A  A  E  E  H  I  P  D  T  H  T         44
AGAAGATGAGAGAAGCCCTGGACTCCTGGGCCTGGCGGTGCCCTGCTGTG         550
 E  D  E  R  S  P  G  L  L  G  L  A  V  P  C  C            60
TGTGCCTGGAAGCTGAGCGCCTGAGAGGGTGTCTCAACTCCGAGAAGATC         600
 V  C  L  E  A  E  R  L  R  G  C  L  N  S  E  K  I         77
TGCATTGTTCCCATTCTGGCTTGCCTAGTCAGCCTCTGCCTCTGCATTGC         650
 C  I  V  P  I  L  A  C  L  V  S  L  C  L  C  I  A         94
TGGCCTGAAGTGGGTATTTGTGGACAAGATATTTGAATACGACTCCTA           700
 G  L  K  W  V  F  V  D  K  I  F  E  Y  D  S  P           110
```

Fig. 3A

```
CCCACCTTGACCCTGGGGGGTTAGGCCAGGACCCTGTGATTTCTCTGGAT    750
 T  H  L  D  P  G  G  L  G  Q  D  P  V  I  S  L  D   127
CCAACTGCTGCCCCAGCCATTTTGGTATCATCCGAGGCATACACTTCACC    800
 P  T  A  A  P  A  I  L  V  S  S  E  A  Y  T  S  P   144
```
SMDF amino
```
TGTCTCTAAGGCTCAGTCTGAAGCTGGGGCTCATGTTACAGTACAAGGTG    850
  V  S  K  A  Q  S  E  A  G  A  H  V  T  V  Q  G     160
ACCATGCTGCTGTGGCCTCTGAACCTTCAGCAGTACCGACCCGGAAGAAC    900
 D  H  A  A  V  A  S  E  P  S  A  V  P  T  R  K  N   177
CGGCTGTCTGCTTTTCCTCCCTTTCACCCTACTGCACCGCCCTTCCCTTC    950
 R  L  S  A  F  P  P  F  H  P  T  A  P  P  F  P  S   194
TCCAGCTCGGACCCCTGAGGTGAGAACACCCAAGTCAGGAACTCAGCCAC   1000
  P  A  R  T  P  E  V  R  T  P  K  S  G  T  Q  P    210
AAACAACAGAAACTAACCTGCAAACTGCTCCTAAACTTTCCACATCAACA   1050
 Q  T  T  E  T  N  L  Q  T  A  P  K  L│S  T  S  T    227
TCCACGACTGGGACCAGCCATCTCATAAAGTGTGCGGAGAAGGAGAAAAC   1100
 S  T  T  G  T  S  H  L  I  K  C  A  E  K  E  K  T   244
```
                    EGF-like Common
```
TTTCTGTGTGAATGGGGGCGAGTGCTTCACGGTGAAGGACCTGTCAAACC   1150
   F  C  V  N  G  G  E  C  F  T  V  K  D  L  S  N    260
CGTCAAGATACTTGTGCAAGTGCCAACCTGGATTCACTGGAGCAAGATGT   1200
 P  S  R  Y  L  C  K  C│Q  P  G  F  T  G  A  R  C    277
                       α
ACTGAGAATGTACCCATGAAAGTCCAAACCCAAGAAAAAGCGGAGGAACT   1250
 T  E  N  V  P  M  K  V  Q  T  Q  E│K│A  E  E  L     294
                                   2
CTACCAGAAGAGGGTGCTGACAATTACTGGCATCTGTATCGCCCTGCTGG   1300
  Y  Q  K  R  V  L  T  I  T  G  I  C  I  A  L  L    310
                          TM
```

Fig. 3B

```
TGGTCGGCATCATGTGTGTGGTGGCCTACTGCAAAACCAAGAAGCAGCGG  1350
 V  V  G  I  M  C  V  V  A  Y  C  K  T  K  K  Q  R   327
CAGAAGCTTCATGATCGGCTTCGGCAGAGTCTTCGGTCAGAACGGAGCAA  1400
 Q  K  L  H  D  R  L  R  Q  S  L  R  S  E  R  S  N   344
CCTGGTGAACATAGCGAATGGGCCTCACCACCCAAACCCGCCGCCAGAGA  1450
  L  V  N  I  A  N  G  P  H  H  P  N  P  P  P  E    360
ACGTGCAGCTGGTGAATCAATACGTATCTAAAAACGTCATCTCCAGTGAG  1500
 N  V  Q  L  V  N  Q  Y  V  S  K  N  V  I  S  S  E   377
CATATTGTTGAGAGAGAAGTGGAGACTTCCTTTTCCACCAGTCATTACAC  1550
  P  I  V  E  R  E  V  E  T  S  F  S  T  S  H  Y  T  394
TTCCACAGCCCATCACTCCACGACTGTCACCCAGACTCCTAGTCACAGCT  1600
  S  T  A  H  H  S  T  T  V  T  Q  T  P  S  H  S    410
```

Common Carboxy

```
GGAGTAATGGGCACACGGAGAGCGTCATTTCAGAAAGCAACTCCGTAATC  1650
 W  S  N  G  H  T  E  S  V  I  S  E  S  N  S  V  I   427
ATGATGTCTTCGGTAGAGAACAGCAGGCACAGCAGTCCCGCCGGGGGCCC  1700
  M  M  S  S  V  E  N  S  R  H  S  S  P  A  G  G  P  444
ACGAGGACGTCTTCATGGCCTGGGAGGCCCTCGTGATAACAGCTTCCTCA  1750
  R  G  R  L  H  G  L  G  G  P  R  D  N  S  F  L    460
GGCATGCCAGAGAAACCCCTGACTCCTACAGAGACTCCTCATAGCGAA    1800
 R  H  A  R  E  T  P  D  S  Y  R  D  S  P  H  S  E   477
AGGTATGTATCAGCCATGACCACCCCGGCTCGTATGTCACCTGTAGATTT  1850
 R  Y  V  S  A  M  T  T  P  A  R  M  S  P  V  D  F   494
CCACACGCCAAGCTCCCCTAAATCGCCCCCTTCGGAAATGTCTCCACCCG  1900
  H  T  P  S  S  P  K  S  P  P  S  E  M  S  P  P    510
TGTCCAGCATGACGGTGTCCATGCCCTCTGTGGCAGTCAGCCCCTTTGTG  1950
 V  S  S  M  T  V  S  M  P  S  V  A  V  S  P  F  V   527
GAAGAAGAGAGGCCTCTGCTGCTTGTGACGCCACCAAGGCTACGGGAGAA  2000
 E  E  E  R  P  L  L  L  V  T  P  P  R  L  R  E  K   544
```

Fig. 3C

```
GAAATATGATCATCACCCCCAGCAACTCAACTCCTTTCATCACAACCCTG  2050
  K   Y   D   H   H   P   Q   Q   L   N   S   F   H   H   N   P      560
CACATCAGAGTACCAGCCTCCCCCCTAGCCCACTGAGGATAGTGGAGGAT  2100
  A   H   Q   S   T   S   L   P   P   S   P   L   R   I   V   E   D  577
GAGGAGTACGAGACGACCCAGGAGTATGAGTCAGTTCAAGAGCCCGTTAA  2150
  E   E   Y   E   T   T   Q   E   Y   E   S   V   Q   E   P   V   K  594
                                       "a" Variant
GAAAGTCACCAATAGCCGGCGGGCCAAAAGAACCAAGCCCAATGGCCACA  2200
  K   V   T   N   S   R   R   A   K   R   T   K   P   N   G   H      610
Carboxy Terminus
TTGCCAATAGGTTGGAAATGGACAGCAACACAAGTTCTGTGAGCAGTAAC  2250
  I   A   N   R   L   E   M   D   S   N   T   S   S   V   S   S   N  627
TCAGAAAGTGAGACAGAAGACGAAAGAGTAGGTGAAGACACACCATTCCT  2300
  S   E   S   E   T   E   D   E   R   V   G   E   D   T   P   F   L  644
GGGCATACAGAACCCCCTGGCAGCCAGCCTTGAGGTGGCCCCCGCCTTCC  2350
  G   I   Q   N   P   L   A   A   S   L   E   V   A   P   A   F      660
GTCTGGCTGAGAGCAGGACTAACCCAGCAGGCCGCTTCTCCACACAGGAG  2400
  R   L   A   E   S   R   T   N   P   A   G   R   F   S   T   Q   E  677
GAATTACAGGCCAGGCTGTCTAGTGTAATCGCTAACCAAGACCCTATTGC  2450
  E   L   Q   A   R   L   S   S   V   I   A   N   Q   D   P   I   A  694
TGTATAAAACCTAAATAAACACATAGATTCACCTGTAAAACTTTATTTTA  2500
  V                (SEQ ID NO. 5)                                    695
TATAATAAAGTATTTCACCTTAAAAAAAAAAAAAAAAAAAA(SEQ ID NO. 4)2540
```

Fig. 3D

```
SMDFβ1a    1  MEIYSPDMSEVAGGRSSSPSTQLSAAPSLDGLPAAEEHIPDTHTEDERSPGLLGLAVPCCVCLEAERLRGCLNSEKICIV
SMDFβ3     1                                   THTEDERSPGLLGLAVPCCVCLEAERLRGCLNSEKICIV
SMDFα2a    1  MEIYSPDMSEVAGGRSSSPSTQLSAVPSLDGLPAAEEHIPDTHTEDERSPGLLGLAVPCCVCLEAERLRGCLNSEKICIV

SMDFβ1A   81  PILACLVSLCLCIAGLKWVFVDKIFEYDSPTHLDPGGLGQDPVISLDPTAAPAILVSSEAYTSPVSKAQSEAGAHVTVQG
SMDFβ3    40  PILACLVSLCLCIAGLKWVFVDKIFEYDSPTHLDPGGLGQDPVISLDPTAAPAILVSSEAYTSPVSKAQSEAGAHVTVQG
SMDFα2A   81  PILACLVSLCLCIAGLKWVFVDKIFEYDSPTHLDPGGLGQDPVISLDPTAAPAILVSSEAYTSPVSKAQSEAGAHVTVQG

SMDFβ1A  161  DHAAVASEPSAVPTRKNRLSAFPPFHSTAPPFPSPARTPEVRTPKSGTQPQTTETNLQTAPKLSTSTSTTGTSHLIKCAE
SMDFβ2     1                    AFPPFHSTAPPFPSPARTPEVRTPKSGTQPQTTETNLQTAPKLSTSTSTTGTSHLIKCAE
SMDFβ3   120  DHAAVASEPSAVPTRKNRLSAFPPFHSTAPPFPSPARTPEVRTPKSGTQPQTTETNLQTAPKLSTSTSTTGTSHLIKCAE
SMDFβ4     1                    AFPPFHSTAPPFPSPARTPEVRTPKSGTQPQTTETNLQTAPKLSTSTSTTGTSHLIKCAE
SMDFα2a  161  DHAAVASEPSAVPTRKNRLSAFPPFHPTAPPFPSPARTPEVRTPKSGTQPQTTETNLQTAPKLSTSTSTTGTSHLIKCAE
SMDFα2b    1                    STAPPFPSPARTPEVRTPKSGTQPQTTETNLQTAPKLSTSTSTTGTSHLIKCAE

SMDFβ1a  241  KEKTFCVNGGECFTVKDLSNPSRYLCKCPNEFTGDRCQNYVMASFY---KHLGIEFME----------AEEL
SMDFβ2    61  KEKTFCVNGGECFTVKDLSNPSRYLCKCPNEFTGDRCQNYVMASFY---K----------------AEEL
SMDFβ3   200  KEKTFCVNGGECFTVKDLSNPSRYLCKCPNEFTGDRCQNYVMASFY---STSTPFLSLPE
SMDFβ4    61  KEKTFCVNGGECFTVKDLSNPSRYLCKCPNEFTGDRCQNYVMASFY---MTSRRKRQETEKPLERKLDHSLVKESKAEE
SMDFα2a  241  KEKTFCVNGGECFTVKDLSNPSRYLCKCQPGFTGARCTENVPMKVQTQEK-----------AEEL
SMDFα2b   55  KEKTFCVNGGECFTVKDLSNPSRYLCKCQPGFTGARCTENVPMKVQTQEK-----------AEEL
```

Fig. 4B

```
SMDFβ1a   300  YQKRVLTITGICIALLVVGIMCVVAYCKTKKQRQKLHDRLRQSLRSERSNLVNIANGPHHPNPPPENVQLVNQYVSKNVI
SMDFα2a   295  YQKRVLTITGICIALLVVGIMCVVAYCKTKKQRQKLHDRLRQSLRSERSNLVNIANGPHHPNPPPENVQLVNQYNSKNVI
SMDFα2b   109  YQKRVLTITGICIALLVVGIMCVVAYCKTKKQRQKLHDRLRQSLRSERSNLVNIANGPHHPNPPPENVQLVNQYVSKNVI

SMDFβ1a   380  SSEHIVEREVETSFSTSHYTSTAHHSTTVTQTPSHSWSNGHTESVISESNSVIMMSSVENSRHSSPAGGPRGRLHGLGGP
SMDFα2a   375  SSEHIVEREVETSFSTSHYTSTAHHSTTVTQTPSHSWSNGHTESVISESNSVIMMSSVENSRHSSPAGGPRGRLHGLGGP
SMDFα2b   189  SSEHIVEREVETSFSTSHYTSTAHHSTTVTQTPSHSWSNGHTESVISESNSVIMMSSVENSRHSSPAGGPRGRLHGLGGP

SMDFβ1a   460  RDNSFLRHARETPDSYRDSPHSERYVSAMTTPARMSPVDFHTPSSPKSPPSEMSPPVSSMTVSMPSVAVSPFVEEERPLL
SMDFα2a   455  RDNSFLRHARETPDSYRDSPHSERYVSAMTTPARMSPVDFHTPSSPKSPPSEMSPPVSSMTVSMPSVAVSPFVEEERPLL
SMDFα2b   269  RDNSFLRHARETPDSYRDSPHSERHNLIAE

SMDFβ1a   540  LVTPPRLREKKYDHHPQQLNSFHHNPAHQSTSLPPSPLRIVEDEEYETTQEYESVQEPVKKVTNSRRAKRTKPNGHIANR
SMDFα2a   535  LVTPPRLREKKYDHHPQQLNSFHHNPAHQSTSLPPSPLRIVEDEEYETTQEYESVQEPVKKVTNSRRAKRTKPNGHIANR

SMDFβ1a   620  LEMDSNTSSVSSNSESETEDERVGEDTPFLGIQNPLAASLEVAPAFRLAESRTNPAGRFSTQEELQARLSSVIANQDPIAV
SMDFα2a   615  LEMDSNTSSVSSNSESETEDERVGEDTPFLGIQNPLAASLEVAPAFRLAESRTNPAGRFSTQEELQARLSSVIANQDPIAV

SMDFβ1a   (SEQ ID NO.  2)
SMDFβ2    (SEQ ID NO.  9)
SMDFβ3    (SEQ ID NO. 11)
SMDFβ4    (SEQ ID NO. 13)
SMDFα2a   (SEQ ID NO.  5)
SMDFα2b   (SEQ ID NO.  7)
```

```
CCCAGCGTGGGCTCGGTGCAGGAGCTGGCCCGGCGCGCCGCGGTGGTGAT    50
  P   S   V   G   S   V   Q   E   L   A   R   R   A   A   V   V   I   17
CGAGGGAAAGGTGCACCCGCCGCGGCGGCAGCAGGGGGCACTCGACAGGA   100
   E   G   K   V   H   P   P   R   R   Q   Q   G   A   L   D   R     33
AGGCAGCAGGCGAGGCAGGGGCAGGGGCGCGGGACCAGCCCGTCCAGGAC   150
   K   A   A   G   E   A   G   A   G   A   R   D   Q   P   V   Q   D   50
TCGCCACCTTCACAGGACCCTCTGCCTGCTGTCAACTGGACCCTGCCCAC   200
   S   P   P   S   Q   D   P   L   P   A   V   N   W   T   L   P   T   67
TGGGGGCCCCGAGCCCAGCACCGATCAGCCCGGGGACCCCGCGCCCTATC   250
   G   G   P   E   P   S   T   D   Q   P   G   D   P   A   P   Y     83
TGGTCAAGGTGCACCAGGTGTGGGCTGTGAAAGCCGGGGGTTTGAAGAAG   300
   L   V   K   V   H   Q   V   W   A   V   K   A   G   G   L   K   K  100
GACTCGCTACTCACCGTGCGCCTGGATACCTGGGGCCACCCAGCCTTCCC   350
   D   S   L   L   T   V   R   L   D   T   W   G   H   P   A   F   P  117
GTCCTGCGGGCGGCTCAAGGAGGACAGCAGGTACATCTTCTTCATGGAGC   400
   S   C   G   R   L   K   E   D   S   R   Y   I   F   F   M   E    133
Kringle
CGGATGCCAACAGCAGCGGCCGCGCGCCGCCCGCCTTCCGAGCCTCGTTT   450
   P   D   A   N   S   S   G   R   A   P   P   A   F   R   A   S   F  150
CCCCCACTGGAGACTGGCCGCAACCTCAAGAAGGAGGTCAGCCGGGTGTT   500
   P   P   L   E   T   G   R   N   L   K   K   E   V   S   R   V   L  167
GTGCAAGCGGTGCGCACTGCCTCCCAGATTGAAAGAAATGAAGAGCCAGG   550
   C   K   R   C   A   L   P   P   R   L   K   E   M   K   S   Q    183
AGTCAGCTGCAGGCTCCAAGCTAGTGCTCCGGTGCGAAACCAGCTCCGAG   600
   E   S   A   A   G   S   K   L   V   L   R   C   E   T   S   S   E  200
TACTCCTCACTCAGATTCAAATGGTTCAAGAATGGGAACGAGCTGAACCG   650
   Y   S   S   L   R   F   K   W   F   K   N   G   N   E   L   N   R  217
CAAAAATAAACCAGAAAACATCAAGATACAGAAGAAGCCAGGGAAGTCAG   700
   K   N   K   P   E   N   I   K   I   Q   K   K   P   G   K   S    233
Ig-Like
AGCTTCGAATTAACAAAGCATCCCTGGCTGACTCTGGAGAGTATATGTGC   750
   E   L   R   I   N   K   A   S   L   A   D   S   G   E   Y   M   C  250
```

Fig. 9A

```
AAAGTGATCAGCAAGTTAGGAAATGACAGTGCCTCTGCCAACATCACCAT  800
 K   V   I   S   K   L   G   N   D   S   A   S   A   N   I   T   I   267
TGTTGAGTCAAACGAGTTCATCACTGGCATGCCAGCCTCGACTGAGACAG  850
   V   E   S   N   E   F   I   T   G   M   P   A   S   T   E   T   283
CCTATGTGTCCTCAGAGTCTCCCATTAGAATCTCAGTTTCAACAGAAGGC  900
 A   Y   V   S   S   E   S   P   I   R   I   S   V   S   T   E   G   300
```
Glycosylation
```
GCAAACACTTCTTCATCCACATCGACATCCACGACTGGGACCAGCCATCT  950
 A   N   T   S   S   S   T   S   T   S   T   T   G   T   S   H   L   317
CATAAAGTGCGCGGAGAAGGAGAAAACTTTCTGTGTGAATGGGGGCGAGT 1000
   I   K   C   A   E   K   E   K   T   F   C   V   N   G   G   E   333
```
EGF-Like Common
```
GCTTCACGGTGAAGGACCTGTCAAACCCGTCAAGATACTTGTGCAAGTGC 1050
 C   F   T   V   K   D   L   S   N   P   S   R   Y   L   C   K   C   350
CCAAATGAGTTTACTGGTGATCGTTGCCAAAACTACGTAATGGCCAGCTT 1100
   P   N   E   F   T   G   D   R   C   Q   N   Y   V   M   A   S   F   367
                                  β
CTACAAGCATCTTGGGATTGAATTTATGGAAGCGGAGGAACTCTACCAGA 1150
   Y   K   H   L   G   I   E   F   M   E   A   E   E   L   Y   Q   383
                             1
AGAGGGTGCTGACAATTACTGGCATCTGTATCGCCCTGCTGGTGGTCGGC 1200
 K   R   V   L   T   I   T   G   I   C   I   A   L   L   V   V   G   400
```
TM
```
ATCATGTGTGTGGTGGCCTACTGCAAAACCAAGAAGCAGCGGCAGAAGCT 1250
 I   M   C   V   V   A   Y   C   K   T   K   K   Q   R   Q   K   L   417
TCATGATCGGCTTCGGCAGAGTCTTCGGTCAGAACGGAGCAACCTGGTGA 1300
   H   D   R   L   R   Q   S   L   R   S   E   R   S   N   L   V   433
ACATAGCGAATGGGCCTCACCACCCAAACCCGCCGCCAGAGAACGTGCAG 1350
 N   I   A   N   G   P   H   H   P   N   P   P   P   E   N   V   Q   450
CTGGTGAATCAATACGTATCTAAAAACGTCATCTCCAGTGAGCATATTGT 1400
 L   V   N   Q   Y   V   S   K   N   V   I   S   S   E   H   I   V   467
```

Fig. 9B

```
TGAGAGAGAAGTGGAGACTTCCTTTTCCACCAGTCATTACACTTCCACAG  1450
  E  R  E  V  E  T  S  F  S  T  S  H  Y  T  S  T     483
CCCATCACTCCACGACTGTCACCCAGACTCCTAGTCACAGCTGGAGTAAT  1500
  A  H  H  S  T  T  V  T  Q  T  P  S  H  S  W  S  N  500
```

Common Carboxy

```
GGGCACACGGAGAGCGTCATTTCAGAAAGCAACTCCGTAATCATGATGTC  1550
  G  H  T  E  S  V  I  S  E  S  N  S  V  I  M  M  S  517
TTCGGTAGAGAACAGCAGGCACAGCAGTCCCGCCGGGGGCCCACGAGGAC  1600
  S  V  E  N  S  R  H  S  S  P  A  G  G  P  R  G     533
GTCTTCATGGCCTGGGAGGCCCTCGTGATAACAGCTTCCTCAGGCATGCC  1650
  R  L  H  G  L  G  G  P  R  D  N  S  F  L  R  H  A  550
AGAGAAACCCCTGACTCCTACAGAGACTCTCCTCATAGCGAAAGGTATGT  1700
  R  E  T  P  D  S  Y  R  D  S  P  H  S  E  R  Y  V  567
ATCAGCCATGACCACCCCGGCTCGTATGTCACCTGTAGATTTCCACACGC  1750
  S  A  M  T  T  P  A  R  M  S  P  V  D  F  H  T     583
CAAGCTCCCCTAAATCGCCCCCTTCGGAAATGTCTCCACCCGTGTCCAGC  1800
  P  S  S  P  K  S  P  P  S  E  M  S  P  P  V  S  S  600
ATGACGGTGTCCATGCCCTCTGTGGCAGTCAGCCCCTTTGTGGAAGAAGA  1850
  M  T  V  S  M  P  S  V  A  V  S  P  F  V  E  E     617
GAGGCCTCTGCTGCTTGTGACGCCACCAAGGCTACGGGAGAAGAAATATG  1900
  R  P  L  L  L  V  T  P  P  R  L  R  E  K  K  Y     633
```

"a" Variant Carboxy Terminus

```
ATCATCACCCCCAGCAACTCAACTCCTTTCATCACAACCCTGCACATCAG  1950
  D  H  H  P  Q  Q  L  N  S  F  H  H  N  P  A  H  Q  650
AGTACCAGCCTCCCCCCTAGCCCACTGAGGATAGTGGAGGATGAGGAGTA  2000
  S  T  S  L  P  P  S  P  L  R  I  V  E  D  E  E  Y  667
CGAGACGACCCAGGAGTATGAGTCAGTTCAAGAGCCCGTTAAGAAAGTCA  2050
  E  T  T  Q  E  Y  E  S  V  Q  E  P  V  K  K  V     683
CCAATAGCCGGCGGGCCAAAAGAACCAAGCCCAATCGCCACATTGCCAAT  2100
  T  N  S  R  R  A  K  R  T  K  P  N  G  H  I  A  N  700
```

Fig. 9C

```
AGGTTGGAAATGGACAGCAACACAAGTTCTGTGAGCAGTAACTCAGAAAG   2150
  R  L  E  M  D  S  N  T  S  S  V  S  S  N  S  E  S   717
TGAGACAGAAGACGAAAGAGTAGGTGAAGACACACCATTCCTGGGCATAC   2200
  E  T  E  D  E  R  V  G  E  D  T  P  F  L  G  I     733
AGAACCCCCTGGCAGCCAGCCTTGAGGTGGCCCCCGCCTTCCGTCTGGCT   2250
  Q  N  P  L  A  A  S  L  E  V  A  P  A  F  R  L  A   750
GAGAGCAGGACTAACCCAGCAGGCCGCTTCTCCACACAGGAGGAATTACA   2300
  E  S  R  T  N  P  A  G  R  T  S  T  Q  E  E  L  Q   767
GGCCAGGCTGTCTAGTGTAATCGCTAACCAAGACCCTATTGCTGTATAAA   2350
  A  R  L  S  S  V  I  A  N  Q  D  P  I  A  V         782
ACCTAAATAAACACATAGATTCACCTGTAAAACTTTATTTTATATAATAA   2400
AGTATTTCACCTTAAATTAAACAATTTATTTTATTTTAGCAGTTCTGCAA   2450
ATAGAAAACAGGAAGAAAAAAACTTTTATAAATTAAATATATGTATGTAA   2500
AAATGTGTTATGTGCCATATGTAGCAATTTTTTACAGTATTTCAAAAACG   2550
AGAAAGATATCAATGGTGCCTTTATGTTCTGTTATGTCGAGAGCAAGTTT   2600
TATAAAGTTATGGTGATTTCTTTTTCACAGTATTTCAGCAAAACCTCCCA   2650
TATATTCAGTTTCTGCTGGCTTTTTGTGGATTGCATTATGATGTTGACTG   2700
GATGTATGGTTTGCAAGGCTAGCAGCTAGCTCGCACTCGCTCTCTCTCTC   2750
TCTCTCTCTCTGTCTGTCTCTCTGTCTCTCTCTCTCTCTCTCTCTCTCTC   2800
TGTCTCTCTCTCTCTCTCTCTCTCTCTCTCTCTCAGCTTCCCGTAGCT    2850
CCCAACCCGTACTGTCTTGGACTGGCACATCCATCCAAATACCTTTCTAC   2900
TTTGTATGAAGTTTTCTTTGCTTTCCAATATGAAATGAGTTCTCTCTAC   2950
TCTGTCAGCCAAAGGTTTGCTTCACTGGACTCTGAGATAATAGTAGACCC   3000
AGCAGCATGCTACTATTATGTATAGCAGGAAACTGCACCAAGTAATGTCC   3050
AATAATAGGAAGAAACGATATC                                3072
```

Fig. 9D

```
CCCATCTCCCCCTTCCTCCCCATAAACAACTCTCCTACCCCCCCATCCCCA      50
ATAAATAAATAAAAGGAGGAGGGTCAGGGTAGGAGTGGGGGCAGGCAAGG      100
CAAGGCAGCTGGAACCAGCCAGGCAGAGTCCGCACCGACAGGCGCTCGCA      150
CGCACCTCACACCATGAGATGGCGACGCGCCCCGCGCCGCCCGCTGGGTA      200
              M   R   W   R   R   A   P   R   R   P   L   G       12
CCAGCCCCAGCGCCGGGCATCCCTGGTCCGCCGGCCGCTCGCCTCCGCTG      250
  T   S   P   S   A   G   H   P   W   S   A   G   R   S   P   P   L      29
CTGCTGCTGCCGCTGCCTCCGCCGCCGCCGCTGCTGCTGCTGCTACT         300
  L   L   L   P   L   P   P   P   P   P   L   L   L   L   L           46
ACTGGGGACCGCGGCCCTGGCTCCGGGGGCGGCGGCTGAGCGGGCGGCTC      350
  L   G   T   A   A   L   A   P   G   A   A   A   E   R   A   A      62
CCGCGGGGGCCTCGGTGTGCTACTCGTCCCCGCCCAGCGTGGGCTCGGTG      400
  P   A   G   A   S   V   C   Y   S   S   P   P   S   V   G   S   V      79
CAGGAGCTGGCCCGGCGCGCCGCGGTGGTGATCGAGGGAAAGGTGCACCC      450
  Q   E   L   A   R   R   A   A   V   V   I   E   G   K   V   H   P      96
GCCGCGGCGGCAGCAGGGGGCACTCGACAGGAAGGCAGCAGGCGAGGCAG      500
  P   R   R   Q   Q   G   A   L   D   R   K   A   A   G   E   A      112
GGGCAGGGGCGCGGGACCAGCCCGTTCAGGACTCGCCACCTTCACAGGAC      550
  G   A   G   A   R   D   Q   P   V   Q   D   S   P   P   S   Q   D      129
CCTCTGCCTGCTGTCAACTGGACCCTGCCCACTGGGGGCCCCGAGCCCAG      600
  P   L   P   A   V   N   W   T   L   P   T   G   G   P   E   P   S      146
CACCGATCAGCCCGGGGACCCCGCGCCCTATCTGGTCAAGGTGCACCAGG      650
  T   D   Q   P   G   D   P   A   P   Y   L   V   K   V   H   Q      162
TGTGGGCTGTGAAAGCCGGGGGTTTGAAGAAGGACTCGCTACTCACCGTG      700
  V   W   A   V   K   A   G   G   L   K   K   D   S   L   L   T   V      179
CGCCTGGATACCTGGGGCCACCCAGCCTTCCCGTCCTGCGGGCGGCTCAA      750
  R   L   D   T   W   G   H   P   A   F   P   S   C   G   R   L   K      196
GGAGGACAGCAGGTACATCTTCTTCATGGAGCCGGATGCCAACAGCAGCG      800
  E   D   S   R   Y   I   F   F   M   E   P   D   A   N   S   S      212
GCCGCGCGCCGCCCGCCTTCCGAGCCTCGTTTCCCCCACTGGAGACTGGC      850
  G   R   A   P   P   A   F   R   A   S   F   P   P   L   E   T   G      229
CGCAACCTCAAGAAGGAGGTCAGCCGGGTGTTGTGCAAGCGGTGCGGTAA      900
  R   N   L   K   K   E   V   S   R   V   L   C   K   R   C           244
GTGCCTCGCCATCCCC                                          916
```

Fig. 9E

```
Rat    MRWRRAPRRPLGTSPSAGHPWSAGRS-PPLLLLPLPPPPPLLLLLLGTAALAPGAAAER-AAPAGASVCYSSPPSVGS    78
       ***** * *** *  *   *  *    * ********** ********         *** ****************
Human  MRWRRAPRRSGRPGPRAQRPGSAARSSPPLPLLP--------LLLLLGTAALAPGAAAGNEAAPAGASVCYSSPPSVGS    71

Rat    VQELARRAAVVIEGKVHPPRRQQGALDRKAA---GEAGA--GARDQPVQDS----PPSQDPLPAVNWTLPT--GGPEPST   147
       ****  ******** **** *********    ***    ** * ****      ******
Human  VQELAQRAAVVIEGKVHPQRRQQGALDRKAAAAAGEAGAWGGDREPPAAGPRALGPPAEEPLLAANGTVPSWPTAPVPSA   151
                                               Kringle Rat    DQPGDPAPYLVKVHQVWAVKAGGLKKDSLLTVRLDTWGHPAFPSCGRLKEDSRYIFFMEPDANSSGRAPPAFRASFPPLE   227
          ********************* *************************     ***********
Human  GEPGEEAPYLVKVHQVWAVKAGGLKKDSLLTVRLGTWGHPAFPSCGRLKEDSRYIFFMEPDANSTSRAPAAFRASFPPLE   231
                                                                   Ig-Like Rat    TGRNLKKEVSRVLCKRCALPPRLKEMKSQESAAGSKLVLRCETSSEYSSLRFKWFKNGNELNRKNKPENIKIQKKPGKSE   307
       ****************** * ****************************************** *********
Human  TGRNLKKEVSRVLCKRCALPPQLKEMKSQESAAGSKLVLRCETSSEYSSLRFKWFKNGNELNRKNKPQNIKIQKKPGKSE   311

Rat    LRINKASLADSGEYMCKVISKLGNDSASANITIVESNEFITGMPASTETAYVSSESPIRISVSTEGANTSSSTSTTTGT   387
       ******************************                                         ******
Human  LRINKASLADSGEYMCKVISKLGNDSASANITIVESN------------------------------ATSTSTTGT    357
                                            Glycosylation
```

Fig. 10A

```
Rat    SHLIKCAEKEKTFCVNGGECFTVKDLSNPSRYLCKCPNEFTGDRCQNYVMASFYKHLGIEFME--AEELYQKRVLTITGI   465
Human  SHLVKCAEKEKTFCVNGGECFMVKDLSNPSRYLCKCPNEFTGDRCQNYVMASFYSTSTPFLSLPE                  422
                     EGF-Like Common                                       JM
                              β                                                       TM
Rat    CIALLVVGIMCVVAYCKTKKQRQKLHDRLRQSLRSERSNLVNIANGPHHPNPPENVQLVNQYVSKNVISSEHIVEREVE   545
Rat    TSFSTSHYTSTAHHSTTVTQTPSHSWSNGHTESVISESNSVIMMSSVENSRHSSPAGGPPRGRLHGLGGPRDNSFLRHARE 625
                                              Common Carboxy
Rat    TPDSYRDSPHSERYVSAMTTPARMSPVDFHTPSSPKSPPSEMSPPVSSMTVSMPSVAVSPFVEEERPLLLVTPPRLREKK  705
Rat    YDHHPQQLNSFHHNPAHQSTSLPPSPLRIVEDEEYETTQEYESVQEPVKKVTNSRRAKRTKPNGHIANRLEMDSNTSSVS  785
                                  "a" Variant Carboxy Terminus
Rat    SNSESETEDERVGEDTPFLGIQNPLAASLEVAPAFRLAESRTNPAGRFSTQEELQARLSSVIANQDPIAV             855
```

Fig. 10B

```
GGFβ1a  MRWRRAPRRPLGTSPSAGHPWSAGRSPPLLLLPLPPPPPLLLLLLGTAALAPGAAAERAAPAGASVCYSSPPSVGSVQ              80

GGFβ1a  ELARRAAVVIEGKVHPPRRQQGALDRKAAGEAGAGARDQPVQDSPPSQDPLPAVNWTLPTGGPEPSTDQPGDPAPYLVKV            160
GGFβ2                                                      PLPAVNWTLPTGGPEPSTDQPGDPAPYLVKV             31
GGFβ4                                                      PLPAVNWTLPTGGPEPSTDQPGDPAPYLVKV             31
GGFβ3                                                      PAPAVNWTLPTGGPEPSTDQPGDPAPYLVKV             31

GGFβ1a  HQVWAVKAGGLKKDSLLTVRLDTWGHPAFPSCGRLKEDSRYIFFMEPDANSSGRAPPAFRASFPPLETGRNLKKEVSRVL            240
GGFβ2   HQVWAVKAGGLKKDSLLTVRLDTWGHPAFPSCGRLKEDSRYIFFMEPDANSSGRAPPAFRASFPPLETGRDLKKEVSRVL            111
GGFβ4   HQVWAVKAGGLKKDSLLTVRLDTWGHPAFPSCGRLKEDSRYIFFMEPDANSSGRAPPAFRASFPPLETGRNLKKEVSRVL            111
GGFβ3   HQVWAVKAGGLKKDSLLTVRLDTWGHPAFPSCGRLKEDSRYIFFMEPDANSSGRAPPAFRASFPPLETGRNLKKEVSRVL            111

GGFβ1a  CKRCALPPRLKEMKSQESAAGSKLVLRCETSSEYSSLRFKWFKNGNELNRKNKPENIKIQKKPGKSELRINKASLADSGE            320
GGFβ2   CKRCALPPRLKEMKSQESAAGSKLVLRCETSSEYSSLRFKWFKNGNELNRKNKPENIKIQKKPGKSELRINKASLADSGE            191
GGFβ4   CKRCALPPRLKEMKSQESAAGSKLVLRCETSSEYSSLRFKWFKNGNELNRKNKPENIKIQKKPGKSELRINKASLADSGE            191
GGFβ3   CKRCALPPRLKEMKSQESAAGSKLVLRCETSSEYSSLRFKWFKNGNELNRKNKPENIKIQKKPGKSELRINKASPADSGE            191

GGFβ1a  YMCKVISKLGNDSASANITIVESNEFITGMPASTETAYVSSESPIRISVSTEGANTSSSTSTSTSTTGTSHLIKCAEKEKTF          400
GGFβ2   YMCKVISKLGNDSASANITIVESNEFITGMPASTETAYVSSESPIRISVSTEGANTSSSTSTSTSTTGTSHLIKCAEKEKTF          271
GGFβ4   YMCKVISKLGNDSASANITIVESNEFITGMPASTETAYVSSESPIRISVSTEGANTSSSTSTSTSTTGTSHLIKCAEKEKTF          271
GGFβ3   YMCKVISKLGNDSASANITIVESNEFITGMPASTETAYVSSESPIRISVSTEGANTSSSTSTSTSTTGTSHLIKCAEKEKTF          271
```

Fig. 11B

```
GGFβ1a  CVNGGECFTVKDLSNPSRYLCKCPNEFTGDRCQNYVMASFYKHLGIEFME-------------------AEELYQKRVLTI  462
GGFβ2   CVNGGECFTVKDLSNPSRYLCKCPNEFTGDRCQNYVMASFYK----------------------AEEL              317
GGFβ4   CVNGGECFTVKDLSNPSRYLCKCPNEFTGDRCQNYVMASFYMTSRRKRQETEKPLERKLDHSLVKESKAEE            342
GGFβ3   CVNGGECFTVKDLSNPSRYLCKCPNEFTGDRCQNYVMASFYSTSTPFLSLPE                               323

GGFβ1a  TGICIALLVVGIMCVVAYCKTKKQRQKLHDRLRQSLRSERSNLVNIANGPHHPNPPPENVQLVNQYVSKNVISSEHIVER   542
GGFβ1a  EVETSFSTSHYTSTAHHSTTVTQTPSHSWSNGHTESVISESNSVIMSSVENSRHSSPAGGPRGRLHGLGGPRDNSFLRH    622
GGFβ1a  ARETPDSYRDSPHSERYVSAMTTPARMSPVDFHTPSSPKSPPSEMSPPVSSMTVSMPSVAVSPFVEEERPLLLVTPPRLR   702
GGFβ1a  EKKYDHHPQQLNSFHHNPAHQSTSLPPSPLRIVEDEEYETTQEYESVQEPVKKVTNSRRAKRTKPNGHIANRLEMDSNTS   782
GGFβ1a  SVSSNSESETEDERVGEDTPFLGIQNPLAASLEVAPAFRLAESRTNPAGRFSTQEELQARLSSVIANQDPIAV          855
```

Fig. 11C

SMDF AND GGF NEUREGULIN SPLICE VARIANT ISOFORMS AND USES THEREOF

CROSS-REFERENCE TO RELATED APPLICATION

This non-provisional patent application claims benefit of provisional patent application U.S. Ser. No. 60/158,622, filed Oct. 8, 1999, now abandoned.

FEDERAL FUNDING LEGEND

This invention was produced in part using funds from the Federal government under grant no. R01 NS37514. Accordingly, the Federal government has certain rights in this invention.

BACKGROUND OF THE INVENTION

1. Field of the Invention

The present invention relates generally to the fields of neurobiology and developmental biology. More specifically, the present invention relates to the identification of novel neuregulin splice variant isoforms.

2. Description of the Related Art

Traumatic injury of adult mammalian peripheral nerve results in degeneration of axon segments and myelin distal to the injury site with concomitant Schwann cell dedifferentiation and proliferation. These changes in Schwann cell morphology are essential for subsequent axonal regeneration (Hall and Gregson, 1977; Pellegrino et al., 1986; Fawcett and Keynes, 1990; Nadim et al., 1990) and are accompanied by increased Schwann cell expression of molecules promoting neurite sprouting [e.g., neurotrophic factors and cell adhesion molecules; reviewed in Fawcett and Keynes, 1990; Fu and Gordon, 1997]. The signals responsible for repressing myelin protein synthesis, inducing expression of molecules supportive of axonal regeneration, and stimulating Schwann cell mitogenesis in injured nerve are poorly understood. It is likely, however, that these signaling molecules include several members of the neuregulin (NRG) family of growth and differentiation factors.

The neuregulin (NRG) family of growth and differentiation factors is thought to form a complex network of intercellular signaling molecules mediating multiple important developmental, maintenance and regenerative functions throughout the nervous system. For instance, neuregulins are highly expressed by sensory and motor neurons during development (Chen et al., 1994; Falls et al., 1993; Ho et al., 1995; Marchionni et al., 1993) and have been implicated as axon-derived signals influencing the differentiation, survival and proliferation of associated Schwann cells during this same period (reviewed in (Topilko et al., 1996; Lemke, 1996)). Neuregulins are also highly potent mitogens for neonatal Schwann cells in vitro (Brockes et al., 1980; Goodearl et al., 1993; Levi et al., 1995) and repress expression of myelin protein zero ($P_0$) and myelin basic protein in these same cells (Cheng and Mudge, 1996). Furthermore, axon-associated NRGs are a component of the "axon-associated mitogen" found on the neurites of neonatal dorsal root ganglion (DRG) neurons (Morrissey et al., 1995). Based on these developmental and in vitro observations, it is hypothesized that neuregulins, potentially released from the injured axon, similarly induce the Schwann cell dedifferentiation and proliferation during the Wallerian degeneration which follows traumatic injury of peripheral nerve and which is essential for subsequent axonal regeneration (Hall and Gregson, 1977; Pellegrino et al., 1986; Fawcett and Keynes, 1990; Nadim et al., 1990).

These molecules are indeed expressed with the temporal and spatial distribution expected for postaxotomy mediators of Schwann cell proliferation and/or other effects in axotomized rat sciatic nerve (Carroll et al., 1997). However, Schwann cells themselves apparently produce neuregulin, a finding consistent with recent reports of neuregulin expression by cultured neonatal Schwann cells in vitro (Raabe et al., 1996; Rosenbaum et al., 1997). Furthermore, the dorsal root ganglia (DRG) sensory and spinal cord motor neurons projecting into the sciatic nerve express the erbB receptors necessary for neuregulin responsiveness during embryogenesis and adulthood. Also, recombinant neuregulin is a survival factor for embryonic day 15 spinal cord motor neurons in vitro. It is therefore likely that neuregulin signaling proceeds bidirectionally between these cell types or that Schwann cell- and neuron-derived neuregulins act in an autocrine fashion.

Since astrocytes, oligodendrocytes and many populations of central nervous system (CNS) neurons similarly express both neuregulins and neuregulin receptors, these same possibilities may need to be considered in the brain. Given the potential complexity of neuregulin signaling among glia and neurons, the question arises as to how neuregulin signaling might be compartmentalized or otherwise regulated. This control may be facilitated, in part, by the synthesis of distinct forms of neuregulin by each expressing cell type. Cloning of neuregulin family members (Wen et al., 1992; Marchionni et al., 1993; Carroll et al., 1997; Falls et al., 1993; Ho et al., 1995; Carroll et al., 1997; Yang et al., 1998) demonstrated these molecules to be structurally diverse proteins translated from alternatively spliced mRNAs transcribed from a single locus. Neuregulins may be divided into three subfamilies, each defined by their unique N terminus and known as the heregulin (HRG)/neu differentiation factor (NDF)/mesenchymal, glial growth factor (GGF) and sensory and motor neuron-derived factor [SMDF; also known as cysteine-rich domain (CRD)-neuregulin] subfamilies.

The structures of various members of the neu differentiation factor subfamily have been thoroughly studied. The seven known neu differentiation factor isoforms are synthesized as either directly secretable forms or as transmembrane precursors requiring proteolytic cleavage for release (Wen et al., 1994). These proteins possess distinct epidermal growth factor (EGF)-like domains ($\alpha$ and $\beta$ isoforms) resulting in differences in receptor affinity (Wen et al., 1994) and ability to induce biological effects (Marikovsky et al., 1995; Pinkas-Kramarski et al., 1996).

The EGF-like domain, which consists of a common region fused to either $\alpha$- or $\beta$-domains, is essential for biologic activity. Truncated $\beta$-neuregulin molecules containing only the EGF-like domain bind to the neuregulin receptor with an affinity similar to that of the full-length factor (Holmes et al., 1992; Peles et al., 1993) and are capable of inducing a variety of biologic responses (Holmes et al., 1992; Peles et al., 1993; Chu et al., 1995; Levi et al., 1995; Syroid et al., 1996).

In spite of their similar structures, neuregulin $\alpha$ and $\beta$ EGF-like domains are not functionally equivalent; $\beta$-neuregulins have an affinity for erbB receptors an order of magnitude greater than $\alpha$-neuregulins (Wen et al., 1994). Furthermore, $\alpha$-neuregulins are nonmitogenic for some, but not all, cell types which proliferate in response to $\beta$-neuregulins (Pinkas-Kramarski et al., 1996).

Further variability in other regions may alter glycosylation (Wen et al., 1994), protease-mediated release from the cell membrane (Wen et al., 1994) and direct signaling by transmembrane precursors (Wang et al., 1998). In addition to the unique amino termini (the functions of which are currently unknown), the mesenchymal and GGF (but not the SMDF) neuregulin subfamilies contain an immunoglobulin-like domain (Ben-Baruch and Yarden, 1994; Peles and Yarden, 1993; Ho et al., 1995) mediating neuregulin interactions with cell surface glycoproteins, with resultant concentration and specific localization of the factor (Sudhalter et al., 1996). Splice variants in the glial growth factor and mesenchymal neuregulin subfamilies also may contain serine and threonine-rich spacer domains which serve as the site of o- and n-linked glycosylation (Wen et al., 1994; Carroll et al., 1997); this glycosylation is non-essential for biologic activity and the precise function(s) of this region is as yet unknown.

Neuregulins may be synthesized as either transmembrane precursors or directly secretable forms. This distinction depends upon the juxtamembrane domain, which is immediately C terminal to the EGF-like domain. Four juxtamembrane domains, designated 1 to 4, have been identified in the rat. In this regard, the '3' juxtamembrane domain is notable in that it, unlike other juxtamembrane domains, contains a termination codon, thus leading to truncation of the factor and synthesis in a directly secretable form. In all other neuregulin isoforms, the juxtamembrane domain is followed by a transmembrane domain which anchors the factor in the cell membrane and is itself coupled to one of three possible cytoplasmic domains (designated a, b, and c) (Wen et al., 1994). The cytoplasmic domains are highly conserved between species, suggesting an essential function (Wen et al., 1994); indeed, it has been recently reported that neuregulin cytoplasmic domains bind LIM kinase 1, suggesting that neuregulin transmembrane precursors are capable of transmitting signals into the interior of the cell synthesizing these proteins (Wang et al., 1998).

Whether members of the glial growth factor and sensory and motor neuron-derived factor subfamilies demonstrate the same degree of structural diversity described for the NDF subfamily has not yet been determined. It is highly likely that the neuregulin isoforms present in injured peripheral nerve represent a diverse population of previously unknown glial growth factor and sensory and motor neuron-derived factor splice variants. The neuregulins selectively induced in axotomized peripheral nerve coincident with the onset of Schwann cell DNA synthesis belong predominantly to the glial growth factor subfamily, while neuregulins of both the glial growth factor and sensory and motor neuron-derived factor subfamilies are expressed in DRG and spinal cord (Carroll et al., 1997).

The prior art is deficient in the lack of knowledge about the sensory and motor neuron-derived factor (SMDF) and glial growth factor (GGF) neuregulin splice variants expressed in the nervous system. The present invention fulfills this longstanding need and desire in the art.

SUMMARY OF THE INVENTION

Other and further aspects, features, and advantages of the present invention will be apparent from the following description of the presently preferred embodiments of the invention. These embodiments are given for the purpose of disclosure.

Reverse transcription-polymerase chain reaction (RT-PCR) analyses suggest that axotomized sciatic nerve, DRG and spinal cord all contain complex mixtures of neuregulin isoforms, potentially representing a large number of previously undescribed splice variants with novel functional characteristics. Consequently, an exhaustive cloning approach was used to identify the neuregulin isoforms expressed in surgically transected rat sciatic nerve, postaxotomy lumbar dorsal root ganglia, postaxotomy lumbar spinal cord and JS1 schwannoma cells, a rat line mimicking at least some characteristics of primary cultures of neonatal rat Schwann cells. The structures of cDNAs encoding six SDMF splice variants and four GGF isoforms are described here, representing both directly secreted proteins and transmembrane precursors. These proteins demonstrate extensive structural variability in multiple regions, suggesting they are functionally distinct.

Whether neuregulin isoforms are predominantly expressed in axotomized peripheral nerve and postaxotomy DRG and spinal cord; (2) whether distinct neuronal subpopulations in the latter two tissues express specific neuregulin splice variants; and, (3) what was the distribution of each group of transcripts was examined. In addition, the biochemical properties of particular neuregulin isoforms, was characterized. These results suggest that neuregulins acting in injured peripheral nerve are part of a complex and tightly regulated network of autocrine/paracrine signals. The operation of this network may rely, in part, on the synthesis of structurally and functionally distinct neuregulin splice variants by specific cellular populations within these tissues.

In one embodiment of the current invention, a cDNA encoding SMDFβ1a, a novel sensory and motor neuron-derived factor (SMDF) splice variant isoform cDNA, is provided. The instant invention is also directed to an isolated. SMDFβ1a protein and a plasmid allowing expression of SMDFβ1a in a cell.

In another embodiment of the current invention, a cDNA encoding a second novel sensory and motor neuron-derived factor (SMDF) splice variant isoform, SMDFα2a, is described. The instant invention is directed to a plasmid containing this cDNA sequence and the regulatory elements necessary for expression of SMDFα2a in a cell and is also directed to an isolated SMDFα2a protein.

A further embodiment of the instant invention is a partial amino acid sequence of SMDF splice variant protein, SMDFα2b. The current invention includes an SMDFα2b protein containing this sequence as well as and a cDNA and plasmid encoding it.

Yet another embodiment of the instant invention comprises partial amino acid and nucleotide sequences of SMDF splice variant proteins SMDFβ2, SMDFβ3, and SMDFβ4. The instant invention is directed to isolated proteins containing these amino acid sequences as well as cDNA molecules and plasmids encoding them.

Yet another embodiment of the instant invention comprises partial amino acid and nucleotide sequences of glial growth factor splice variant proteins GGFβ1a, GGFβ2, GGFβ3, and GGFβ4. The instant invention is directed to isolated proteins containing these amino acid sequences as well as cDNA molecules and plasmids encoding them.

A further embodiment of the instant invention is a method of treating condition of nerve dysfunction comprising the step of administering an effective dose of SMDFβ1a, SGGFα2a, SMDFα2b, SMDFβ2, SMDFβ3, SMDFβ4, GGFβ1a, GGFβ2, GGFβ3, or GGFβ4. Such a method of treatment is likely to be useful in the treatment of demyelinating diseases such as multiple sclerosis, nerve injuries such as spinal cord and peripheral nerve injuries and neuropathies, neurodegenerative diseases such as Alzheimer's disease and Parkinson's disease, and motor neuron diseases such as ALS and Werdnig-Hoffman disease.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A–1D show nucleotide and deduced amino acid sequence of a rat SMDFβ1a cDNA clone isolated from a spinal cord/brainstem library. Numbering of the cDNA sequence is relative to the first nucleotide of the clone. The predicted amino acid sequence (underlined) corresponds to the largest open reading frame identified in the cDNA and is numbered (italicized, to right) relative to the first amino acid of this reading frame. Neuregulin protein domains are identified as follows: SMDF amino, the unique SMDF amino terminal domain; EGF-like Common, the portion of the neuregulin EGF-like domain common to all neuregulin isoforms; β, the neuregulin EGF-like β variant domain; 1, the "1" variant juxtamembrane domain; TM, transmembrane domain; Common Carboxy, intracellular domain common to all neuregulin transmembrane splice variants; "a" Variant Carboxy Terminus, the "a" variant carboxy terminal domain. Two hydrophobic segments representing potential membrane insertion signals are doubly underlined within the SMDF amino terminal domain. The protein coding sequences are preceded by a 635 bp 5' untranslated region. This cDNA contains only 118 bp of 3' untranslated region which does not include a polyadenylated tract.

FIG. 2 shows a comparison of the predicted full-length protein sequences of rat SMDFβ1a and human SMDFβ3 (Ho et al., 1995). Residues which differ between these sequences are indicated by asterisks. Dashes indicate gaps introduced to maximize alignment. The SMDF amino terminal domain sequences are boxed. Bold overlines designate the positions of two hydrophobic segments representing potential membrane insertion signals. The putative transmembrane segment is underlined in the rat SMDFβ1a sequence.

FIGS. 3A–3D shows nucleotide and deduced amino acid sequence of a rat SMDFα2a cDNA isolated from a JS1 schwannoma cDNA library. The predicted amino acid sequence (underlined) is derived from the largest open reading frame identified in this cDNA and is numbered (italicized, to right) relative to the first amino acid of this reading frame. Neuregulin protein domains are identified as follows: SMDF amino, the SMDF amino terminal domain; EGF-like Common, the portion of the EGF-like domain common to all neuregulin splice variants; α, the neuregulin EGF-like α domain; 2, the "2" variant juxtamembrane domain; TM, transmembrane domain; Common Carboxy, intracellular domain common to all neuregulin transmembrane precursors; "a" Variant Carboxy Terminus, the "a" variant carboxy terminal domain found in a subset of neuregulin transmembrane precursors. Two hydrophobic segments within the SMDF amino terminal domain which are potential membrane insertion signals are doubly underlined. A consensus polyadenylation signal within the 3' untranslated region is boldly underlined.

FIGS. 4A–4C show rat SMDF cDNA sequences isolated from rat spinal cord/brainstem and JS1 schwannoma cDNA libraries and by reverse transcription-polymerase chain reaction using a rat lumbar dorsal root ganglion/spinal cord cDNA template. In FIG. 4A, boxes represent protein coding, 5' and 3' untranslated regions; connecting lines are included only to designate association of adjacent regions. Domains are indicated as follows: 5' UTR, 5' untranslated region; Amino, SMDF amino terminal domain with the internal dark bar marking the location of the putative membrane insertion signal within the SMDF amino terminal domain; EGF, the neuregulin EGF-like common domain; α and β, the neuregulin α and β EGF-like variant domains; 1,2,3 or 4, juxtamembrane domains; TM, transmembrane domain; Cytoplasmic, the intracellular domain common to all neuregulin transmembrane splice variants; a or b, variant carboxy terminal domains; 3' UTR, 3' untranslated region. The size of each isolated cDNA (in base pairs, bp) and the number of amino acid residues (aa) encoded by the corresponding cDNA is indicated to the right of each structure. Note that several of these cDNAs include only partial protein coding sequences and that the predicted protein sizes therefore do not reflect the complete length of the precursor protein. FIGS. 4B–4C show alignment of the deduced amino acid sequences of rat SMDFβ1a, SMDFβ2, SMDFβ3, SMDFβ4, SMDFα2a and SMDFα2b. The putative transmembrane segment is underlined. Dashes represent gaps introduced to produce optimal alignment of the sequences. The region demonstrating the greatest degree of sequence diversity, the EGF-like variable and juxtamembrane domains, is boxed. Arrowheads indicate positions of specific amino acids in the SMDF amino and EGF-like common domains differing between some clones. A bold bracket indicates the partial "b" variant carboxy terminus identified in one cDNA.

FIG. 5A shows polyadenylated RNA (2 μg per lane) isolated from adult rat brain and spinal cord as well as from noninjured sciatic nerve (Noninj.) and sciatic nerve distal to a site of surgical transection 3 days postaxotomy (3 day) was blotted and probed for expression of SMDF transcripts. The probe, indicated in the diagram beneath the blot, is a 1014 bp fragment encoding sequences spanning the 5' untranslated region and amino terminal half of the SMDF amino terminal region from pSLC135, the SMDFβ1a cDNA presented in FIG. 1. This probe detects two major mRNA transcripts, estimated at 3.5 and 7.5 kb (arrows, to left of diagram), in brain and spinal cord but not in noninjured or axotomized sciatic nerve. FIG. 5B shows PCR fingerprint analysis and indicates that neuregulin transmembrane isoforms, including SMDF splice variants, in rat lumbar dorsal root ganglia (DRG) and lumbar spinal cord (Spinal Cord) are overwhelmingly represented by β-isoforms. PCR was performed using cDNAs reverse transcribed from the indicated tissues and primers (arrows) hybridizing to sequences flanking the EGF-like domain and the juxtamembrane domains; these two regions are common to all known transmembrane neuregulin isoforms. PCR reactions were divided into thirds, with one portion digested with HaeIII (specifically cleaving PCR products encoding βneuregulin isoforms), the second portion digested with DdeI (specific for αneuregulin isoform cDNAs) and the third portion remaining undigested. Virtually all of the PCR product from DRG and spinal cord is cleaved by HaeIII to release a fragment of the expected 167 bp size. In contrast, DdeI produces no recognizable shift in the size of the PCR product. Consequently, neuregulins in the spinal cord and DRG, including SMDF isoforms, are predominantly represented by β-isoforms, with α-isoforms being undetectable in this assay.

FIG. 6A shows that 10, 25 or 50 μg of total cellular RNA from adult rat brain, 50 μg of total cellular RNA from the rat JS1 schwannoma cell line or 50 μg of yeast tRNA was hybridized to an antisense $^{32}$P-labeled riboprobe spanning the carboxy terminal portion of the SMDF amino terminus (SMDF), the neuregulin βEGF-like domain (EGF, β), the "1" juxtamembrane domain (1) and the initial portion of the transmembrane domain (TM; see diagram beneath autoradiogram). The diagram below the autoradiogram also indicates the fragment sizes expected for SMDFβ1, other SMDFβ isoforms (SDMFβ), SMDFα isoforms, neuregulinβ1 and neuregulinβ splice variants other than SMDF (EGFβ1 and EGFβ, respectively) and neuregulinα splice variants other than SMDFα (EGFα). Arrows to the light of the diagram indicate the positions of neuregulin splice variants detected following ribonuclease digestion; the size of standards, in base pairs, is indicated to the left of the diagram. FIG. 6B shows that 25 μg of total cellular RNA from adult rat whole brain (Brain), Cortex, Midbrain, Brainstem, Cerebellum, spinal cord (Cord), noninjured sciatic nerve (Noninj.Nerve), sciatic nerve distal to a site of surgical transection collected 7 days postaxotomy (7 DayNerve), adrenal gland (Adrenal) and lumbar dorsal root ganglia (DRG) was hybridized to the same SMDFβ1 riboprobe illustrated in A. Arrows to the right of the panel indicate the positions of neuregulin isoforms detected in this experiment. The sizes of standards, in base pairs (bp) is indicated on the left of the panel.

FIG. 7A shows that 10 μg of total cellular RNA isolated from gastrocnemius/soleus muscle (Muscle), skin from the dorsum of the hindfoot (Skin), Testis, Kidney, small intestine (Sm. Intestine), Stomach, Liver, Spleen, Thymus, Lung and Heart was resolved by electrophoresis, blotted and probed with the 1014 bp SMDF-specific probe illustrated in FIG. 5. In this prolonged (two week) exposure, bands of estimated at 2.5, 3.5 and 7.5 kb sizes are detected in total cellular RNA from several non-neural tissues, including stomach and testis. FIG. 7B shows that templates for reverse transcription were prepared from 5 μg of total cellular RNA isolated from the indicated tissues. PCR was performed using these templates or a water blank (Blank) with primers hybridizing to sequences in the SMDF amino terminus and the transmembrane domain (Arrows); the sequences recognized by these primers are common to all SMDF transmembrane isoforms. Tissues examined include whole adult rat brain (Brain), Cortex, Cerebellum, Brainstem, Spinal Cord, Adrenal, sciatic nerve [both Noninjured and distal to a site of surgical transection 3 days after axotomy (3 days distal)], Heart, Lung, Thymus, Spleen, Liver, Stomach, large intestine (Large Int.), Kidney, Testis, skin from the dorsum of the hind foot (Skin) and gastrocnemius/soleus muscle (Muscle). In these experiments, SMDF transcripts were routinely detected in virtually all tissues in the body except spleen; in some experiments, SMDF mRNA was also detectable in this tissue.

FIGS. 9A–9E show the nucleotide and deduced amino acid sequence of a rat GGFβ1a cDNA clone and genomic sequences encoding the amino terminus of this cDNA. FIGS. 9A–9D: numbering of this rat GGFβ1a cDNA sequence is relative to the first nucleotide of the clone. The predicted amino acid sequence (underlined) corresponds to the largest open reading frame identified in the cDNA and is numbered (italicized, to right) relative to the first amino acid of this reading frame. Neuregulin protein domains are identified as follows: Kringle, the GGF amino terminal domain; Ig-Like, the neuregulin immunoglobulin-like domain; Glycosylation, a 34 amino acid region containing multiple potential sites of O- and N-linked glycosylation; EGF-like Common, the neuregulin EGF-like common domain; β, the neuregulin EGF-like β variant domain; 1, the "1" juxtamembrane domain; TM, transmembrane domain; Common Carboxy, intracellular domain common to all neuregulin transmembrane splice variants; "a" Variant Carboxy Terminus, the "a" variant carboxy terminal domain. A region which we have noted to be poorly conserved between the rat and human sequences is doubly underlined in the kringle domain. FIG. 9E: nucleotide and deduced amino acid sequence of genomic DNA encoding the rat GGF amino terminus. Numbering of the genomic sequence (nonitalicized, to right) is relative to the first nucleotide of the sequence presented above. The predicted amino acid sequence indicated partially overlaps with the amino terminus of the GGFβ1a protein presented in A (amino acid residues 74–244 of the protein sequence derived from this genomic clone; italicized numbers, to right). The methionine residue designated as the translation start site represents the first methionine present in this reading frame and is preceded by several termination codons.

FIGS. 10A–10B show the comparison of rat GGFβ1a and human GGF-II proteins. The predicted full-length protein sequences of rat GGFβ1a and human GGF-II [GGFβ3 {Marchionni, Goodearl, et al. 1993 ID: 77}(GenBank accession no. AAB59622)] were aligned by the Clustal method. Residues differing between these sequences are indicated by asterisks. Dashes indicate gaps introduced to maximize alignment. Neuregulin protein domains are identified as follows: Kringle, the GGF amino terminal domain; Ig-Like, the neuregulin immunoglobulin-like domain; Glycosylation, a 34 amino acid region containing multiple potential sites of O- and N-linked glycosylation; EGF-like Common, the neuregulin EGF-like common domain; β, the neuregulin EGF-like β variant domain; JM, juxtamembrane domains; TM, transmembrane domain; Common Carboxy, intracellular domain common to all neuregulin transmembrane splice variants; "a" Variant Carboxy Terminus, the "a" variant carboxy terminal domain. Note that the human sequence lacks the glycosylation domain identified in the rat sequence. The rat and human sequences also have distinct juxtamembrane domains; human GGF-II has a "3" juxtamembrane domain which contains a termination codon, allowing its synthesis as a directly secreted protein. In contrast, the EGF-like domain of the rat protein is coupled to a "1" juxtamembrane domain which is followed by a transmembrane domain and extensive cytoplasmic sequences. In contrast to human GGF-II, the rat GGFβ1a protein is synthesized as a transmembrane precursor requiring proteolytic cleavage for release.

FIGS. 11A–11C show a comparison of the structure of GGF cDNAs isolated from postaxotomy sciatic nerve, DRG and cord and their encoded proteins. FIG. 11A: Rat GGF structures predicted from cDNA sequences isolated from a rat JS1 schwannoma cDNA library and by reverse transcription-polymerase chain reaction using a rat lumbar dorsal root ganglion/spinal cord cDNA template. Boxes represent protein coding, 5' and 3' untranslated regions; connecting lines are included only to indicate association of adjacent regions. Domains are indicated as follows: Kringle, the GGF amino terminal domain; Ig-Like, the neuregulin immunoglobulin-like domain; Glycosylation, a 34 amino acid region containing multiple potential sites of O- and N-linked glycosylation; EGF, the neuregulin EGF-like common domain; β, the neuregulin β EGF-like variant domain; 1,2,3 or 4, juxtamembrane domains; Cytoplasmic, the intracellular domain common to all neuregulin transmembrane splice variants; a or b, variant carboxy terminal domains; 3'UTR, 3' untranslated region. The size of the isolated cDNA (in base pairs, bp) and the number of amino acid residues (aa) encoded by each of these clones is indicated to the right of each structure. Note that several of these cDNAs include only partial protein coding sequences and that the sizes therefore do not reflect the complete length of the precursor protein. (FIGS. 11B–11C) Alignment of the deduced amino acid sequences of rat GGFβ1a, GGFβ2, GGFβ3 and GGFβ4. Dashes represent gaps introduced to produce optimal alignment of the sequences. Arrowheads indicate positions of amino acid residues differing between some isolated clones. The region of maximum sequence diversity among these sequences is boxed.

DETAILED DESCRIPTION OF THE INVENTION

Figure 4A:
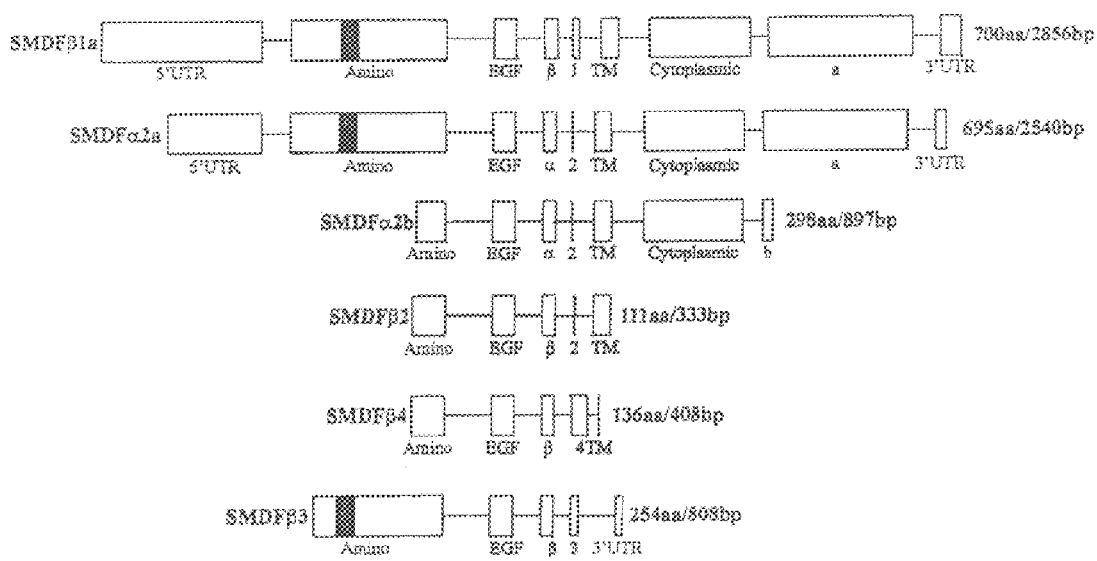

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acid described herein are preferred to be in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552–59 (1969), abbreviations for amino acid residues are known in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl)

terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, the term "host" is meant to include not only prokaryotes but also eukaryotes such as yeast, plant and animal cells. A recombinant DNA molecule or gene which encodes a protein of the present invention can be used to transform a host using any of the techniques commonly known to those of ordinary skill in the art. Prokaryotic hosts may include *E. coli, S. tymphimurium, Serratia marcescens* and *Bacillus subtilis.* Eukaryotic hosts include yeasts such as *Pichia pastoris,* mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors.

Reverse transcription-polymerase chain reaction (RT-PCR) analyses suggest that axotomized sciatic nerve, DRG and spinal cord all contain complex mixtures of neuregulin isoforms, potentially representing a large number of previously undescribed splice variants with novel functional characteristics. Consequently, an exhaustive cloning approach was used to identify the neuregulin isoforms expressed in surgically transected rat sciatic nerve, postaxotomy lumbar dorsal root ganglia, postaxotomy lumbar spinal cord and JS1 schwannoma cells, a rat line mimicking at least some characteristics of primary cultures of neonatal rat Schwann cells. The structure of cDNAs encoding six SDMF splice variants and four GGF isoforms was determined, representing both directly secreted proteins and transmembrane precursors.

These proteins demonstrate extensive structural variability in multiple regions, suggesting they are functionally distinct. These results suggest that neuregulins acting in injured peripheral nerve are part of a complex and tightly regulated network of autocrine/paracrine signals. The operation of this network may rely, in part, on the synthesis of structurally and functionally distinct neuregulin splice variants by specific cellular populations within these tissues.

The current invention is directed to SMDFβ1a, a sensory and motor neuron-derived factor (SMDF) splice variant isoform. The instant invention also includes an isolated cDNA encoding SMDFβ1a and a plasmid allowing expression of SMDFβ1a in a cell.

The instant invention is also directed to a second sensory and motor neuron-derived factor (SMDF) splice variant isoform, SGGFα2a. The instant invention also includes the cDNA encoding SMDFα2a as well as a plasmid containing this cDNA sequence and the regulatory elements necessary for expression the protein in a cell.

Yet another embodiment of the instant invention comprises the partial amino acid sequence of SMDF splice variant protein, SMDFα2b. The current invention includes an isolated SMDFα2b protein and a cDNA and a plasmid encoding this protein.

The instant invention is also directed to novel SMDF splice variant isoforms SMDFβ2, SMDFβ3, and SMDFβ4. Partial amino acid sequences for each of these proteins are given. The instant invention include proteins containing these sequences and cDNAs and plasmids encoding these proteins.

The current invention is further directed to comprises partial amino acid and nucleotide sequences of glial growth factor splice variant proteins GGFβ1a, GGFβ2, GGFβ3, and GGFβ4. The instant invention is also directed to isolated proteins containing these amino acid sequences as well as cDNA molecules and plasmids encoding them.

In addition, the instant invention is directed to a method of treating various forms of nerve dysfunction comprising the step of administering an effective dose of SMDFβ1a, SGGFα2a, SGGFα2b, SMDFβ2, SMDFβ3, SMDFβ4, GGFβ1a, GGFβ2, GGFβ3, or GGFβ4 to a patient to induce nerve repair Such a method is likely to find use in the treatment of demyelinating diseases such as multiple sclerosis, nerve injuries such as spinal cord and peripheral nerve injuries and neuropathies, neurodegenerative diseases such as Alzheimer's disease and Parkinson's disease, and motor neuron diseases such as ALS and Werdnig-Hoffman disease.

The following examples are given for the purpose of illustrating various embodiments of the invention and are not meant to limit the present invention in any fashion.

EXAMPLE 1

Cell Culture

MCF-7 breast carcinoma cells were obtained from the American Type Culture Collection (Rockville, Md.). JS1 rat schwannoma cells and DG44 Chinese hamster ovary (CHO) cells were provided by Drs. Eugene Johnson (Dept. of Pharmacology and Molecular Biology, Washington University School of Medicine) and Jeffrey Milbrandt (Dept. of Pathology, Washington University School of Medicine), respectively. MCF-7 cells were grown in minimal essential medium (MEM) supplemented with 10% fetal calf serum (FCS), 200 μM L-glutamine, 10 μg/ml streptomycin and 10 IU/ml penicillin. JS1 cells were cultured in Dulbecco's modified Eagle medium (DMEM) with 10% FCS, 200 μM L-glutamine, 10 μg/ml streptomycin and 10 IU/ml penicillin. DG44 CHO cells were grown in Ham's F12 medium supplemented with 10% FCS, 200 μM L-glutamine, 10 μg/ml streptomycin and 10 IU/ml penicillin.

EXAMPLE 2

Primary Cultures of Rat Neonatal Schwann Cells

Primary cultures of rat neonatal Schwann cells were established from the sciatic nerve of postnatal day five rat pups by the technique of Brockes et al. (1979). Contaminating fibroblasts were removed by treating cultures for 72 hours with $10^{-5}$M cytosine arabinoside. Cultures were then expanded in DMEM containing 10% FCS, 0.2 nM rNRGβ1$_{168-237}$ (see below), 5 μM forskolin, 200 μM L-glutamine, 10 μg/ml streptomycin and 10 IU/ml penicillin. 98–99% of the surviving cells were Schwann cells as assessed by their immunoreactivity for S100β. Schwann cells in their second and third passages were used for the experiments described in this work.

EXAMPLE 3

Isolation and Sequencing of Rat SMDF and GGF Precursor cDNA's Expressed in Spinal Cord The isolation of four neuregulin cDNAs from a rat spinal cord/brainstem library was previously described (Carroll et al., 1997). Preliminary analysis revealed that clone pSLC135 was a SMDF splice variant while another clone, pSLC132, encoded a GGF splice variant. The complete nucleotide sequences of these cDNA's were determined using a commercial dye terminator cycle sequencing kit (Applied Biosystems, Inc.; Foster City, Calif.) with synthetic oligonucleotide primers and an automated sequencing machine (ABI Model 373A DNA Sequencing System). The resulting sequences were assembled and analyzed with the aid of Lasergene Seqman II software (Windows Version 3.58; DNAStar, Madison, Wis.).

EXAMPLE 4
Construction and Screening of a JS1 Schwannoma Cell cDNA Library

Polyadenylated RNA isolated from 80% confluent cultures of JS1 schwannoma cells was used to synthesize cDNA by the technique of Gubler and Hoffman (1983); cDNAs were synthesized in two separate reactions in which first strand synthesis was primed with either oligo dT or random hexamers. Following treatment with EcoRI methylase, T4 DNA polymerase and DNA polymerase I (Klenow fragment), double-stranded cDNA was ligated to EcoRI linkers and then digested with EcoRI. The resulting cDNA was fractionated by gel filtration chromatography and cDNAs larger than 500 bp were ligated to EcoRI digested λZAPII arms (Stratagene; La Jolla, Calif.). Ligated phage was packaged (Gigapack Gold; Stratagene) and plated on *E. coli* (XL-1 Blue mrf' strain; Stratagene). A total of $2\times10^6$ primary recombinants was amplified.

For screening, phage were plated at high density (50,000 plaques per plate), and duplicate filter lifts prepared from each plate (Maniatis et al., 1990). The insert from pSLC135 was $^{32}$P-labeled by the random oligonucleotide priming method (Feinberg and Vogelstein, 1984) using a commercial kit (Prime-a-Gene Labeling System; Promega, Madison, Wis.) and labeled probe purified using spin columns (MidiSELECT-D columns; 5 Prime-3Prime, Inc., Boulder, Colo.). Radiolabeled probe ($5\times10^5$ cpm/ml) was hybridized to filters representing a total of $1.2\times10^6$ plaque forming units under high stringency conditions [50% formamide/5×saline-sodium citrate (SSC)/5×Denhardt's/0.1% sodium dodecyl sulfate (SDS) at 42° C.]. Filters were washed four times at room temperature in 2×SSC/0.1% SDS (fifteen minutes per wash) followed by two 68° C. washes in 0.2×SSC/0.1% SDS (one hour per wash). Three clones were identified in this manner and purified by limiting dilution (Maniatis et al., 1990). Plasmids were rescued from λ phage by coinfecting XL-1 Blue mrf' bacteria with the λ phage and ExAssist helper phage (Stratagene) and then passaging the resulting rescued phagemid through *E. coli* (SOLR strain; Stratagene). Initial sequence analyses of two of the resulting cDNAs (pSLC275 and pSLC276) demonstrated them to be SMDF cDNAs. The complete sequence of these cDNAs was determined using an automated DNA sequencer and synthetic oligonucleotide primers as described above.

EXAMPLE 5
RACE Analyses

For rapid amplification of cDNA ends (RACE) analysis, the cDNA template was synthesized using a commercial kit (Marathon cDNA Amplification kit; CLONTECH Laboratories Inc., Palo Alto, Calif.) and polyadenylated RNA was isolated from JS1 schwannoma cells. 5' RACE products were amplified from the JS1 cDNA by long-distance PCR (Expand High Fidelity kit; Boehringer-Mannheim) using the universal forward primer (AP1) supplied with the RACE kit and a reverse primer designed from either the sequence of the SMDFβ1a cDNA [pSLC135; primer sequence TATGT-TCCTCCGCTGCCGGAA (SEQ ID No.: 14)] or the sequence of the GGFβ1a cDNA (pSLC132; primer sequence CAATCTGGGAGGCAGTGCGCA (SEQ ID No. 28). PCR parameters, after an initial two minute melt at 94° C., were thirty cycles of 94° C. for 30 seconds, 55° C. for 30 seconds and 72° C. for two minutes, with a 20 second/cycle increase in the 72° C. step for cycles 11–30.

PCR products were resolved on a 1% gel, depurinated (10 minutes at room temperature in 0.25N HCl) and denatured (15 minute and 30 minute room temperature incubations in 0.5N NaOH/0.6M NaCl). Nucleic acids were then blotted to Sureblot membrane (Oncor; Gaithersburg, Md.) and baked per the manufacturer's recommendations. A 1014 bp BamHI/EcoRI fragment encoding the 5' untranslated region and a portion of the amino terminus of a SMDFβ1a cDNA (pSLC135) was $^{32}$P-labeled by the random oligonucleotide priming method (Feinberg and Vogelstein, 1984). Likewise, a 432 bp NotI fragment encoding a portion of the amino terminus (kringle domain) of a GGFβ1a cDNA (pSLC132) was $^{32}$P-labeled by the same random priming method. Radiolabeled probes ($5\times10^5$ cpm/ml) were hybridized to the blots under high stringency conditions (50% formamide/5× SSC/5×Denhardt's/0.1% SDS at 42° C.). The blots were washed four times at room temperature in 2×SSC/0.1% SDS (15 minutes per wash), twice at 68° C. washes in 0.2×SSC/0.1% SDS (one hour per wash) and then exposed to Kodak XAR-5 film at –80° C. with two intensifying screens.

EXAMPLE 6
PCR Cloning of Additional SMDF and GGF Splice Variants

Oligonucleotides were designed with the aid of Lasergene PrimerSelect software (Windows Version 3.10; DNAStar) whenever possible. The common SMDF amino terminus forward oligonucleotides used for PCR of SMDF isoforms were designed from the sequence of a SMDFβ1a cDNA (clone pSLC135) and have the sequences GCTTTTCCTC-CCTTTCAC (SEQ ID No.: 15) and CACCCACACAGAA-GATGAGAG (SEQ ID No.: 16). The GGF amino terminus (kringle domain) forward primer used for amplification of GGF cDNAs was derived from the sequence of a GGFβ1a cDNA (pSLC132) and has the sequence ACCCTCTGCCT-GCTGTCAACT (SEQ ID No.: 29). The common reverse oligonucleotide for PCR of SMDF and GGF transmembrane isoforms corresponds to nucleotides 1067–1049 of a rat NDF transmembrane precursor cDNA (GenBank accession no. U02323)(Wen et al., 1994). The specific α2 reverse oligonucleotide represents nucleotides 1058–1038 of a NDFα2b clone (GenBank accession no. U02316) (Wen et al., 1994). The specific β2 reverse primer corresponds to nucleotides 1049–1029 of a NDFβ2a cDNA (GenBank accession no. U02321) (Wen et al., 1994). The α-specific reverse oligonucleotide represents nucleotides 1040–1020 of a NDFα2b cDNA (GenBank accession no. U02316) (Wen et al., 1994). The β-specific reverse oligonucleotide spans residues 1034–1016 of a NDFβ2a clone (GenBank accession no. U02321) (Wen et al., 1994). The specific "4" juxtamembrane domain reverse oligonucleotide corresponds to nucleotides 1124–1101 of a NDFβ4a splice variant (GenBank accession no. U02322)(Wen et al., 1994). The specific reverse oligonucleotide for secreted SMDF and GGF isoforms corresponds to nucleotides 731–710 in the 3' untranslated region of a NDFβ3 splice variant (GenBank accession no. U02315)(Wen et al., 1994).

Single-stranded cDNA templates were synthesized from polyadenylated RNA isolated from a pool of lumbar dorsal root ganglia and lumbar spinal cord (collected 7d and 10d postaxotomy) and a pool of sciatic nerve distal to a site of surgical transection (16 hr, 3d and 7d postaxotomy). Synthesis of cDNA was performed in a 20 μl reaction using random hexamer primers and Moloney murine leukemia virus reverse transcriptase (Superscript Plus; Life Technologies, Gaithersburg, Md.). After completion of reactions, samples were diluted to 100 μl with distilled water, boiled for five minutes and stored at –20° C. until use. Two microliters of cDNA was used as PCR template in reactions performed for 35 cycles of 94° C. for 1 min., 55° C. for 1 min. and 72° C. for 2 min. After verification of synthesis by gel electrophoresis, PCR products were chloroform extracted, ligated directly into the EcoRV site of pT7Blue or pT7Blue-3, and ligations were transformed into E. coli (NovaBlue strain) as recommended by the manufacturer (Novagen). The identity and sequence of the clones was then determined by cycle sequencing using an automated sequencer (see above).

A partial SMDF and GGF cDNA's were amplified using long-distance (LD)-PCR performed as per the manufacturer's recommendations (Expand High Fidelity kit; Boehringer-Mannheim), with a rat spinal cord/DRG cDNA template produced. Conditions used for this LD-PCR were identical to the conditions described above (see RACE Analyses). The resulting PCR product was cloned into pT7Blue-3 and sequenced as described above.

EXAMPLE 7

Northern Blot Analyses

Total cellular RNA was isolated from tissues by the technique of Chomczynski and Sacchi (1987). Polyadenylated RNA was isolated from total cellular RNA by oligo dT affinity chromatography (Oligotex Kit; Qiagen). For. Northern blot analyses, fifteen micrograms of each total cellular RNA or one microgram of each polyadenylated RNA was fractionated on 1% agarose gels containing 2.2M formaldehyde and transferred to Sureblot nylon membrane (Oncor; Gaithersburg, Md.) per the manufacturer's recommendations. Blots were baked under vacuum for 30 minutes at 80° C. Following a 1–2 hour prehybridization at 42° C. in Hybrisol III (45% formamide/5×SSC/10% dextran sulfate/1% SDS/100 µg/ml denatured salmon sperm DNA/1 µg/ml poly A), membranes were hybridized for 16–24 hours with DNA probes ($5 \times 10^5$ cpm/ml) 32P-labeled by the random oligonucleotide priming method (Feinberg and Vogelstein, 1984). Blots were washed three times in 2×SSC/0.5% SDS at room temperature (15 minutes per wash) followed by two washes (30 minutes per wash) in 0.2×SSC/0.5% SDS at 68° C. Membranes were exposed to Kodak XAR-5 film at –80° C. with two intensifying screens.

EXAMPLE 8

Ribonuclease Protection Assays

The template used to produce a $^{32}$P-labeled riboprobe for ribonuclease protection assays was pSLC331 (encoding a portion of the SMDF amino terminus, EGF-like β1 domain and a small region of the transmembrane domain). $^{32}$P-labeled riboprobes were transcribed from the linearized template with T7 RNA polymerase and purified from 5% polyacrylamide gels containing 8M urea. After initial optimization of hybridization conditions and RNase concentrations, ribonuclease protection assays were performed with an RPA II kit following the manufacturer's recommendations (Ambion; Austin, Tex.). Protected fragments were resolved on 5% polyacrylamide gels containing 8M urea. Gels were dried and exposed to Kodak XAR-5 film at –80° C. with two intensifying screens to visualize reaction products. Size standards used in these experiments were pBluescript II KS(+) digested with HpaII and $^{32}$P-end-labeled with DNA polymerase I (Kienow fragment). In some experiments, a cyclophilin riboprobe transcribed from pSLC109 (Carroll and Frohnert, 1998) was hybridized to RNA together with the SMDF riboprobes to verify recovery of protected fragments.

EXAMPLE 9

Reverse Transcription (RT)-PCR Detection and Fingerprint Analyses of SMDF Isoforms in Rat Tissues Five micrograms of total cellular RNA isolated from tissues of interest was treated with 3U of RNase-free DNase (RQ1 DNase; Promega) for 1 hour at 37° C. in MMLV reverse transcription buffer and then heated for five minutes at 95° C. RNA was then reverse transcribed in a 20 µl reaction with random hexamer primers and MMLV reverse transcriptase; a portion of each DNase digested sample was not reverse transcribed and was used to verify an absence of genomic DNA contamination. After completion of the reactions, samples were diluted to 100 µl with distilled water, boiled for five minutes and stored at –20° C. until use.

For detection of SMDF RNA, two non-overlapping pairs of primers were used in independent experiments. The first set of primers used was the first common SMDF amino terminus primer and the common reverse primer for transmembrane isoforms described above. The second set of primers corresponds to sequences in the 5' untranslated region of a SMDFβ1a cDNA (pSLC135) and have the sequences CAGACGCCTGAGGTGAGAAACAT (SEQ ID No.: 17) and AAGTCCAAGGCAATTACCCAAAGT (SEQ ID No.: 18). 0.6 µM concentrations of each primer were used in reactions containing 5 µl of cDNA template; 1×Taq buffer; 1.5 mM MgCl$_2$; 80 µM each of dATP, dGTP and dTTP; 40 µM dCTP; 1.5 µCi of α-$^{32}$P-dCTP and 1.5 U Taq polymerase in a 50 µl reaction volume. Cycle parameters, following an initial two minute melt at 94° C., were 35 cycles of 94° C. for 30 seconds, 55° C. for 30 seconds and 72° C. for 2 minutes. Ten microliters of each PCR reaction was resolved on 5% polyacrylamide gels containing 0.5×TBE (44.5 mM Tris/44.5 mM boric acid/1 mM EDTA). Gels were dried and reaction products visualized by exposing gels to Kodak XAR-5 film at –80° C. with two intensifying screens.

For PCR fingerprint analyses, PCR reactions were performed with α-$^{32}$P-dCTP as described above. After completion of the PCR reaction, 20 µl aliquots were digested with restriction endonucleases in a 50 µl reaction volume. The entire restriction digestion as well as the remaining 10 µl of undigested PCR product was resolved on 5% polyacrylamide gels containing 0.5×TBE. Gels were dried and exposed to Kodak XAR-5 film at –80° C. with two intensifying screens.

EXAMPLE 10

In situ Hybridizations

Surgical transection of one sciatic nerve was performed on adult (300–350 g male Harlan Sprague-Dawley rats as previously described (Carroll et al., 1997; Carroll and Frohnert, 1998). At the desired postaxotomy interval, rats were anesthetized and perfused transcardially first with 0.85% saline and then with 4% paraformaldehyde in phosphate-buffered saline (PBS; pH 7.4). Lumbar DRG and the lumbar enlargement of the spinal cord were dissected free and postfixed overnight at 4° C. in 4% paraformaldehyde in PBS. The next morning, tissues were rinsed twice with ice-cold PBS, transferred to 0.5M sucrose in PBS and equilibrated at 4° C. for 24–38 hrs. In situ hybridizations were performed using eight micron cryosections as previously described (Carroll et al., 1992). Sense and antisense $^{33}$P-labeled riboprobes were transcribed from plasmids pSLC123 (encoding NRG EGF-like common, EGF-like β and 1 juxtamembrane domains) and pSLC111 (encoding the NRG immunoglobulin-like domain).

EXAMPLE 11
Production of Bacterially-Expressed Truncated Neuregulin

Truncated rat NRGβ1 containing the EGF-like and juxtamembrane regions (rNRGβ1$_{168-237}$) was produced using the bacterial expression vector pSLC219, which contains the indicated amino acids under the control of the T7lac promoter in pET28b(+) (Novagen); this vector was selected for the production of recombinant neuregulin after preliminary experiments with other expression vectors [pET21b(+), pET22b(+)] demonstrated that neither varying the size of the resulting protein or attempting to direct its secretion into the periplasmic space prevented bacteria from sequestering recombinant protein into inclusion bodies.

For expression of recombinant protein, pSLC219 was transferred into the BL21(DE3) strain of *E. coli*. 50 ml cultures were grown to an OD$_{600}$ of 0.6 and expression induced with 1 mM isopropyl-1-thio-β-D-galactopyranoside (IPTG) for three hours. Bacteria were pelleted and lysed by sonication in 1×binding buffer [20 mM Tris (pH 7.9)/0.5 M NaCl/5 mM imidazole] containing 6M guanidinium isothiocyanate. Recombinant protein was bound to nickel chelate columns (His-Bind resin; Novagen). Bound recombinant protein was washed with 1×wash buffer [20 mM Tris (pH 7.9)/0.5 M NaCl/60 mM imidazole] and then eluted with elution buffer [20 mM Tris (pH 7.9)/0.5 M NaCl/1M imidazole] containing 8M urea. Denatured neuregulin protein was refolded by sequential dialysis against a base buffer [10 mM Tris (pH 7.9)/100 mM NaH$_2$PO$_4$/150 mM NaCl/3 mM cysteine/10% glycerol/0.02% Tween-20] containing progressively decreasing concentrations of urea (8M, 4M, 2M, 1M, 0.5 M urea; 24 hours dialysis per step) and then against 1×phosphate buffered saline (PBS) containing 10% glycerol. Using this approach, 5–6 mg of recombinant protein is typically obtained from a 50 ml bacterial culture. The resulting protein is >98% pure as assessed by analytical reverse phase high pressure liquid chromatography. Protein preparations were assayed for bacterial endotoxin contamination using a Limulus amebocyte lysate assay (BioWhittaker; Walkerville, Md.) and verified to be free of detectable levels of endotoxin. Biological activity of the recombinant protein was assessed by examining its ability to stimulate erbB receptor tyrosine phosphorylation in MCF-7 cells (see below for specifics of this assay). With these preparations, maximal tyrosine phosphorylation is obtained with nanomolar concentrations of recombinant protein, a result identical to that previously reported with similarly truncated neuregulin proteins (Holmes et al., 1992; Peles et al., 1993).

EXAMPLE 12
Stable Expression of SMDF Protein in DG44 CHO Cells

To produce full-length recombinant SMDF protein in mammalian cells, the insert from pSLC135 (a SMDFβ1a cDNA) was excised with XhoI and NotI and cloned into the expression vector pBK-CMV (Stratagene) digested with the same enzymes to produce plasmid pSLC338.

EXAMPLE 13
Stable Expression of SMDF and GGF Proteins in DG44 CHO Cells

Nine micrograms of each SMDF or GGF expression plasmid, together with one microgram of a plasmid (pHLD-DHFR) expressing dihydrofolate reductase (DHFR) and carrying a genomic sequence promoting effective amplification of the transected sequences (the HSAG-1 element (McArthur and Stanners, 1991)), was transfected into a CHO line with a null mutation of the DHFR locus (DG44 CHO cells) by calcium precipitation (Chen and Okayama, 1987). Twenty-four hours after transfection, cells were refed with Ham's F12 supplemented with 10% FCS, 200 μM L-glutamine, 10 μg/ml streptomycin and 10 IU/ml penicillin. Seventy-two hours after transfection, cells were changed to MEMα medium (which selects for dhfr expression) containing 400 μg/ml G418 (which selects for the pBK-CMV resistance marker). After initial selection, expression of SMDF or GGF protein was amplified by selection with increasing concentrations of methotrexate. Pools of selected clones were used for subsequent experiments.

EXAMPLE 14
Assay of ErhB Tyrosine Phosphorylation in MCF-7 Cells $3 \times 10^5$ MCF-7 breast carcinoma cells were plated in each well of a 24 well plate in MEM supplemented with 10% FCS, 10 μg/ml streptomycin and 10 IU/ml penicillin. Twenty-four hours after plating, the complete medium was replaced with MEM containing 0.1% bovine serum albumin (BSA) and the cells were serum-starved for two hours. Media was then replaced with MEM containing 0.1% BSA with specific concentrations of recombinant neuregulin or media conditioned by candidate cell lines. MCF-7 cells were stimulated for 15 minutes at 37° C. At the end of this time, media was removed and cells rinsed with Hanks' balanced salt solution. Cells were then lysed by the addition of 100 μl of 1×SDS sample buffer [0.125 M Tris (pH 6.6)/10% β-mercaptoethanol/2% SDS/2 μg/ml aprotinin/10 μg/ml leupeptin/2 mM PMSF/50 mM sodium fluoride/10 mM sodium orthovanadate/10 mM sodium molybdate/20 μM phenylarsine oxide/10 mM sodium pyrophosphate]. Lysates were collected and stored at −20° C. until use. 25 μl of each lysate was resolved on 8% SDS polyacrylamide gels and electroblotted onto PVDF membrane. Equivalent transfer was verified by Coomassie staining of residual protein in the gel. A rabbit polyclonal antiphosphotyrosine antibody (Transduction Laboratories; Lexington, Ky.) was diluted in TBST [0.15 M NaCl, 10 mM Tris (pH 8.0), 0.05% Tween 20, 0.002% sodium azide] containing 1% nonfat dry milk and applied to membranes. Horseradish peroxidase conjugated goat anti-rabbit secondary antibody (Jackson Immunoresearch Laboratories; West Grove, Pa.) was used at a 1:7000 dilution in TBST. Immunoreactive species were detected by enhanced chemiluminescence (Pierce).

EXAMPLE 15
Clone Designations and Nucleotide Sequence Accession Numbers

The SMDF clones isolated and their designations are as follows: SMDFβ1a, pSLC135; SMDFβ4, pSLC252; SMDFα2b, pSLC275; SMDFα2a, pSLC276; SMDFβ3, pSLC284; SMDFβ2, pSLC348. The GGF clones isolated and their designations are GGFβ1a, pSLC132; GGFβ2, pSLC346; GGFβ3, pSLC347; and, GGFβ4, pSLC345.

EXAMPLE 16
Nucleotide Sequence of a Rat SMDF Transmembrane Precursor Expressed in the Adult Central Nervous System The isolation of four neuregulin cDNAs from a rat spinal cord/brainstem library was previously described (Carroll et al., 1997). Preliminary analyses indicated that one of these clones, plasmid pSLC135, encoded a previously undescribed SMDF transmembrane precursor protein. To fully establish the structure of this novel protein, the complete sequence of the pSLC135 cDNA was determined and is given in SEQ ID No. 1.

The largest open reading frame in this 2856 bp cDNA (FIGS. 1A–1D, underlined) begins with an ATG at nucleotide 636, extends to a TAA termination codon at residue 2736 and encodes a 700 amino acid polypeptide with predicted $M_r$ 76,385. The amino acid sequence is listed in SEQ ID No. 2. These protein coding sequences are preceded by a 635 bp 5' untranslated region. Rapid amplification of cDNA ends (RACE) performed using a rat JS1 schwannoma cell template (see below) followed by hybridization with SMDF specific probes internal to the expected amplified sequences identified no sequences extending beyond the 5' end of the pSLC135 cDNA (data not shown), suggesting that this clone contains a nearly complete representation of the mRNA 5' untranslated region. In contrast, the protein coding region of the pSLC135 cDNA is followed by only 118 bp of 3' untranslated sequences which do not include a polyadenylated tract. Based on these structural characteristics and an estimate of a minimal 3.5 kb size for the major SMDF mRNAs expressed in spinal cord and brain (see below), it is likely that the pSLC135 cDNA does not include the entire length of 3' untranslated region sequences present in the corresponding mRNA.

EXAMPLE 17

Deduced Amino Acid Sequence of the pSLC135 Rat SMDF

The amino terminal portion of the protein sequence predicted by the pSLC135 cDNA has several important structural features that confirm its identification as an SMDF isoform. A sequence database search with the protein sequence predicted by the pSLC135 cDNA established that the amino terminal region of this polypeptide (FIGS. 1A–1D, SMDF amino; FIG. 2, boxed sequences) is closely related (82.5% sequence identity) to the equivalent region of a protein encoded by a human SMDFβ3 cDNA(Ho et al., 1995) (Ho et al., 1995). As with ARIA (Falls et al., 1993), heregulin (Holmes et al., 1992), NDF (Wen et al., 1994) and human SMDF (Ho et al., 1995), the pSLC135 protein lacks a hydrophobic N-terminal signal peptide. Hydrophilicity analysis (Kyte and Doolittle, 1982) of the pSLC135 polypeptide instead demonstrates the presence of two hydrophobic regions near the N terminus, $Ser^{49}$-$Leu^{63}$ and $Ile^{77}$-$Val^{101}$, which are highly conserved between rat and man [three conservative mutations in the first hydrophobic stretch and complete identity in the second (FIGS. 1A–1D, doubly underlined; FIG. 2, bars over the SMDF domain)]; it has been suggested that these hydrophobic stretches function as uncleaved internal signals for membrane translocation (Ho et al., 1995). Eight cysteine residues within the hydrophobic sequences are identically placed and conserved between these two species. Given the high degree of sequence conservation within the amino terminal domain and the identification of the conserved structural features noted above, it is concluded that the pSLC135 cDNA encodes a rat SMDF splice variant.

EXAMPLE 18

Relationship of Rat pSLC135 SMDF to Other SMDF Proteins

Although the protein encoded by the pSLC135 cDNA is clearly a member of the SDMF neuregulin subfamily, it is not the rat equivalent of the human SMDFβ3 isoform reported by Ho et al. (Ho et al., 1995). Alignment of the proteins predicted by the rat pSLC135 and human SMDFβ3 cDNAs shows that the closely related amino terminal sequences of these proteins (FIG. 2, boxed sequences) are both followed by an EGF-like domain containing a region common to all neuregulin isoforms and a β variant domain (one of two possible sequences, α or β, previously found in other neuregulins at this position). Thereafter the rat and human sequences diverge. The EGF-β variant domain of the human SMDFβ3 sequence is followed by an 11 amino acid region (a "3" juxtamembrane domain (Wen et al., 1994)) which culminates in a termination codon, thereby allowing the synthesis of this molecule in a directly secreted form.

In contrast, the EGF-β variant domain in the pSLC135 protein is followed by a nine amino acid juxtamembrane domain sequence (1, FIGS. 1A–1D) identical to a similarly located sequence in some NDF isoforms (Wen et al., 1994) which in turn is coupled to a large region identical to the equivalent portion of a protein sequence predicted by a NDFβ2a cDNA isolated from ras-transformed Rat-1-EJ cells (Wen et al., 1994). This large expanse of carboxy terminal sequence includes a 31 amino acid putative transmembrane domain (FIGS. 1A–1D, TM; FIG. 2, underlined), a 157 amino acid cytoplasmic region common to all neuregulin transmembrane precursors (FIG. 1, Common Carboxy), and a 219 amino acid "a" variant carboxy terminus [one of three alternative sequences (a, b or c) reported by Wen et al. (Wen et al., 1994) in rat NDF splice variants].

It is therefore apparent that, in contrast to the directly secreted human SMDFβ3 isoform, the rat pSLC135 protein is synthesized as a transmembrane precursor requiring proteolytic cleavage for the release of soluble factor. Following a convention which names neuregulin splice variants on the basis of their alternative usage of variable domains in the order amino terminus-EGF variable domain-juxtamembrane domain-variable carboxy terminal domain (Holmes et al., 1992; Wen et al., 1994), the protein encoded by the pSLC135 cDNA was designated as an SMDFβ1a isoform.

EXAMPLE 19

Analysis of SMDFα Isoforms Expressed by JS1 Schwannoma Cells

In light of the extreme structural variability previously identified in the mesenchymal (heregulin/NDF) neuregulin subfamily (Wen et al., 1994), it is reasonable to postulate that the SMDF neuregulin subfamily may demonstrate a similar array of alternative forms with diverse functional characteristics. As an initial test of this hypothesis, an expanded search for SMDF cDNAs was undertaken. It was previously reported that the rat JS1 schwannoma cell line (Schubert et al., 1974) expresses a variety of neuregulin mRNAs, including transcripts encoding SMDF isoforms (Carroll et al., 1997). Therefore, a JS1 cDNA library was constructed and screened with the SMDFβ1a cDNA described above, resulting in the isolation of three additional neuregulin clones. Based on their characteristic amino terminal sequences, two cDNAs, 2.5 kb and 0.9 kb in length, were identified as SDMF isoforms; the third cDNA represents a novel GGF clone which will be described in Example 30.

EXAMPLE 20

Characterization of JS1 Schwannoma Cell pSLC276 SMDF cDNA

To establish the structure of the encoded proteins, the complete sequence of the two SMDF cDNAs isolated from JS1 schwannoma cells was determined. The larger of these cDNAs, pSLC276 (SEQ ID No. 4), spans 2540 bp, which includes a complete SMDF coding sequence, beginning with an ATG at nucleotide 370 and extending through a TAA termination codon at residue 2455 (FIGS. 3A–3D). This reading frame is preceded by 353 bp (nucleotides 18–369) of 5' untranslated region which is completely colinear with the 5' untranslated sequences present in the rat SMDFβ1a cDNA described above.

In contrast, the 3' untranslated region of the pSLC276 cDNA differs from that of the pSLC135 clone. The coding sequences in the pSLC276 cDNA are followed by only a short region (63 bp) of 3' untranslated sequences which show complete identity with the initial 63 bp of the 3' untranslated region found in pSLC135. Notably, the truncated 3' untranslated region of pSLC276 contains a consensus polyadenylation signal [AATAAA (SEQ ID No.: 19); nucleotides 2504–2508] which begins 18 bp 5' of a 19 bp polyadenylated tract (FIGS. 3A–3D). Based on the identity of the initial sequences of the pSLC135 and pSLC276 3' untranslated sequences, the presence of a polyadenylation consensus signal and a poly A(+) tract, it was concluded that the shortening of the 3' untranslated region of the pSLC276 cDNA results from the utilization of alternative polyadenylation sites rather than an alternative splicing event involving the 3' end of this transcript.

EXAMPLE 21
Protein Encoded by JS1 Schwannoma Cell pSLC276 SMDF cDNA

The protein sequence derived from the pSLC276 cDNA is also that of an SMDF transmembrane precursor protein. Translation of the largest open reading frame in this clone predicts a 695 amino acid polypeptide ($M_r$ 75,646) (SEQ ID No. 5), which contains the distinctive SMDF amino terminus (FIGS. 3A–3D, SMDF amino). Alignment of the pSLC276 protein with the rat SMDFβ1a polypeptide (presented diagrammatically in FIG. 4A and as aligned sequences in FIGS. 4B–4C) demonstrates these sequences to be highly similar with the exception of the C terminal portion of the EGF-like domain and the adjacent segment coupling the EGF-like domain to the transmembrane segment and cytoplasmic domains. In the pSLC276 protein, the EGF-like β and "1" juxtamembrane domain are replaced by EGF-like α and "2" juxtamembrane domains (FIGS. 4B–4C, boxed). Following the nomenclature conventions cited above, the protein predicted by this cDNA is therefore an SMDFα2a isoform. Also of note are two conservative amino acid substitutions in the SMDF amino terminal sequences (FIGS. 4B–4C, first two arrowheads); it is currently unclear whether these changes represent simple polymorphisms, mutations arising in the neoplastic JS1 schwannoma cell line or cloning artifacts introduced during reverse transcription of the original mRNA.

EXAMPLE 22
JSI Schwannoma Cell pSLC275 SMDF cDNA

The second SMDF clone isolated from the JS1 schwannoma library, pSLC275, is a partial cDNA (SEQ ID No. 6) which encodes a portion of an SMDF transmembrane precursor protein (FIG. 4A). Alignment of the partial protein sequence (SEQ ID No. 7) predicted by the pSLC276 cDNA with the rat SMDFβ1a and SMDFα2a polypeptides shows that the pSLC275 protein is virtually identical to SMDFα2a with the exception of its last six amino acids (bracket, FIGS. 4B–4C). These sequences instead encode the first six amino acids of an alternative ("b" variant) carboxy terminal domain previously identified in a NDF transmembrane precursor (Wen et al., 1994). Accordingly, the protein encoded by the pSLC275 cDNA represents an SMDFα2b isoform.

EXAMPLE 23
Analysis of Additional SMDF Splice Variants Expressed in Rat Spinal Cord and Dorsal Root Ganglia Following Sciatic Axotomy Although the cDNA library screens led to the identification of three novel rat SMDF splice variants (SMDFβ1a, SMDFα2a and SMDFα2b), considerably greater structural diversity is found in the rat NDF subfamily (seven isoforms (Wen et al., 1994)), suggesting that further SMDF splice variants remained unidentified. Therefore, reverse transcription-polymerase chain reaction (RT-PCR) was used to investigate the potential existence of additional SMDF isoforms expressed in the rat nervous system.

Dorsal root ganglion sensory and spinal cord motor neurons express high levels of SMDF mRNA (Ho et al., 1995), possibly representing a component of the "axon-associated mitogen" associated with newly extending axons of DRG sensory neurons (Morrissey et al., 1995). Accordingly, the cDNA template used for these experiments was prepared from a pool of total cytoplasmic RNA isolated from noninjured rat lumbar dorsal root ganglia and spinal cord and the same tissues collected 7 and 10 days after surgical transection of the sciatic nerve (a period during which neurite outgrowth is actively occurring).

The greatest degree of structural variability was observed clustered in the EGF-like variable and juxtamembrane domains. Multiple PCR primers were designed to amplify sequences encompassing the carboxy terminal portion of the SMDF amino terminus, the EGF-like common and variant domains, and the juxtamembrane domains of both directly secreted and transmembrane precursor SMDF isoforms. The reverse oligonucleotides used in these experiments included primers expected to hybridize to a target cDNA regardless of which EGF-like variant and juxtamembrane domains are present as well as oligonucleotides directed towards specific expected splice variants. All possible combinations of these primers were used to amplify SMDF sequences from the DRG/spinal cord template. After initial screening and grouping of 104 candidate cDNAs, representative clones from each group of PCR products were sequenced in their entirety. SMDF sequences were readily detectable in DRG and spinal cord with this analysis and were represented by multiple alternatively spliced transcripts. In addition to partial cDNAs with a sequence identical to that determined for pSLC135, the previously described SMDFβ1a clone, other clones were identified which had complete sequence identity with SMDFβ1a in the amino-terminal region and EGF-like domain, but diverged thereafter (FIG. 4A). In total, three additional SMDF cDNA were isolated which are SEQ ID No. 8 encoding SEQ ID No. 9, SEQ ID No. 10 encoding SEQ ID No. 11, and SEQ ID No. 12 encoding SEQ ID No. 13.

EXAMPLE 24
Comparison of Isolated SMDF Splice Variants to SMDFβ1a

A comparison of the complete sequences of each of the cDNAs isolated from JS1 cells, dorsal root ganglia, and spinal cord to that of the SMDFβ1a cDNA demonstrates that the larger cDNA isolated from the JS1 line contains a complete protein coding sequence whereas the other clones contain sequences encoding only a portion of each polypeptide (FIGS. 4A, B, C). These cDNAs include representatives of clones encoding six related SMDF precursor proteins. The amino terminal sequences and EGF-like common domain of the five additional predicted proteins are identical to that of SMDFβ1a, with no internal insertions or deletions seen in these structures in any clone. However, structural variation is present in three regions carboxy terminal to the constant regions.

First, the two cDNAs isolated from JSI cells contain an α EGFvariable domain rather than the β variable domain present in all clones isolated from spinal cord and DRG. Second, four distinct juxtamembrane domains were present which were identical to sequences previously designated as 1 to 4 in mesenchymal neuregulin isoforms (Wen et al., 1994). Lastly, two different variant carboxy terminal domains were identified in the clones isolated from JS1 schwannoma cells. A comparison of these latter sequences to those previously identified in the mesenchymal neuregulin subfamily demonstrates the variable carboxy terminal domains are identical to regions previously designated as "a" and "b" carboxy terminal sequences (Wen et al., 1994). Following the nomenclature convention noted above, the isolated SMDF cDNAs encode SMDFβ1a, SMDFα2a, SMDFα2b, SMDFβ2 (SEQ ID No. 8), SMDFβ3 (SEQ ID No. 10) and SMDFβ4 (SEQ ID No. 12) isoforms.

EXAMPLE 25
Northern Blot Analysis of SMDF mRNA Expression in Noninjured and Postaxotomy Rat Sciatic Nerve, Lumbar Spinal Cord and Dorsal Root Ganglia To examine the specific expression and size of any SMDF transcripts in rat sciatic nerve and tissues containing the neurons projecting into this structure (lumbar spinal cord and the L4 to L6 dorsal root ganglia), Northern blot analyses were performed. Polyadenylated RNA isolated from adult rat brain (a control tissue expected to express SMDF mRNA), adult rat lumbar spinal cord, noninjured adult rat sciatic nerve and sciatic nerve collected 3 days after surgical transection was blotted and hybridized to a probe specific for SMDF mRNAs (spanning the 5' untranslated region and a portion of the SMDF amino terminus; see the diagram at the bottom of FIG. 5A).

Figure 5A:
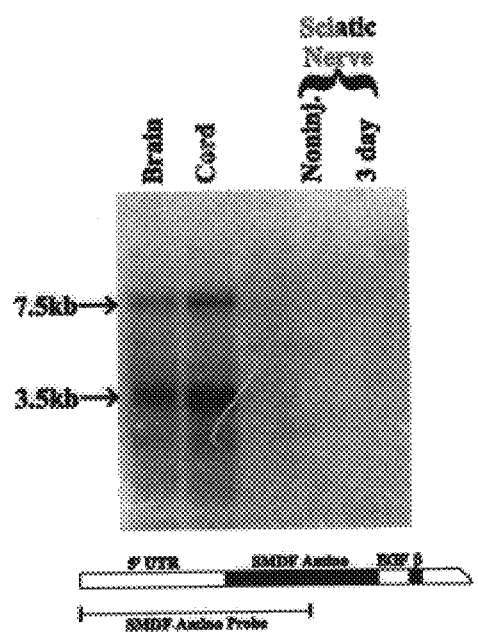
FIGS. 5A and 5B show Northern blot and PCR fingerprint analyses of SMDF splice variant expression in adult rat sciatic nerve and tissues containing the neurons contributing motor and sensory axons to this structure.

The results of a Northern blot analysis are shown in FIG. 5A. Two major SMDF messengers, 3.5 kb and 7.5 kb in size, are evident in poly A+ RNA from both adult rat brain and lumbar spinal cord, with the 3.5 kb mRNA being particularly prominent in spinal cord (FIG. 5A). In contrast, SMDF transcripts were undetectable in noninjured or 3 day post-axotomy sciatic nerve (FIG. 5A), even with prolonged (three week) exposures (data not shown). It is therefore apparent that sciatic nerve and spinal cord differ in their relative expression of this neuregulin subfamily.

EXAMPLE 26
Fingerprint Analyses of RT-PCR Products to Distinguish the Expression of the Splice Variants Although it is evident from these experiments that SMDF mRNAs accumulate in adult rat lumbar spinal cord, little information is available regarding the structure of the SMDF splice variants present in this tissue. In particular, identification of SMDFα isoforms raises the question of whether these splice variants are also expressed by DRG sensory and spinal cord motor neurons, a finding which would have important biologic implications given the differing affinities and biologic activities of α and β neuregulins. As an initial assessment of a and β-isoform expression in lumbar spinal cord and dorsal root ganglia following nerve injury, finger-print analyses of RT-PCR products were used to distinguish the expression of these splice variants.

Figure 5B:
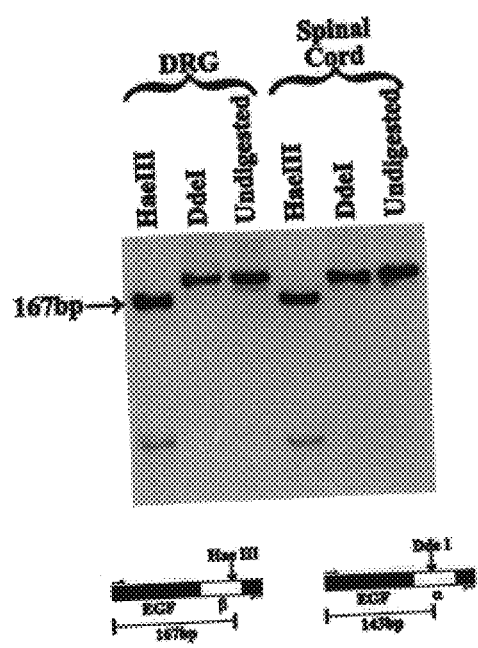

For these experiments, the EGF-like domains of the neuregulin transmembrane precursors expressed in lumbar dorsal root ganglia and spinal cord (7 and 10 days after surgical transection of the sciatic nerve) were amplified using primers spanning this domain and the adjacent juxtamembrane domain. A portion of each product was then digested with restriction endonucleases specifically cleaving α or β isoforms. The results of this analysis are shown in FIG. 5B.

Figure 6A:
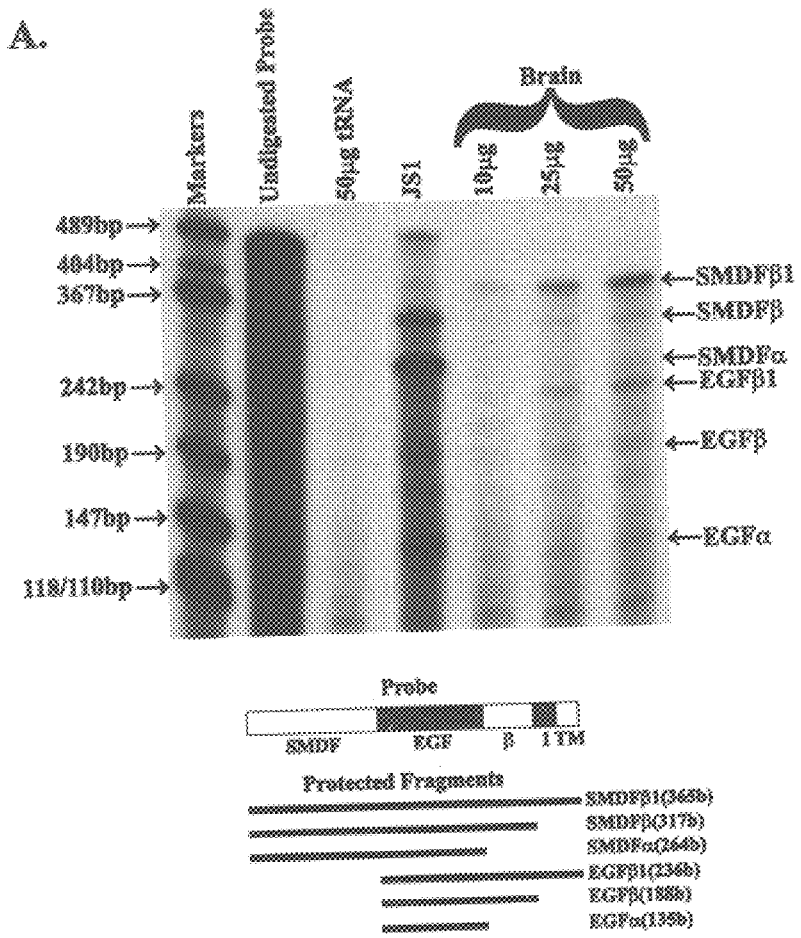
FIGS. 6A and 6B show ribonuclease protection analyses of SMDF splice variant expression in adult rat nervous system.

EXAMPLE 27
Ribonuclease Protection Analyses of SMDF Splice Variant Expression SMDF splice variant expression in adult rat nervous system was analyzed by ribonuclease protection analysis. Total cellular RNA from adult rat brain or from rat JS1 schwannoma cell was hybridized to an antisense $^{32}$P-labeled riboprobe spanning a region from the carboxy terminal portion of the SMDF amino terminus to the initial portion of the transmembrane domain. After hybridization and RNase digestion, protected fragments were resolved on 8M urea 5% polyacrylamide gels and exposed to autoradiography. The results of the RNAse protection are shown in FIG. 6A. The diagram below the autoradiogram indicates the fragment sizes expected for SMDFβ1, other SMDFβ isoforms (SDMFβ), SMDFα isoforms, NRGβ1, NRGβ splice variants EGFβ1 and EGFβ, and NRGα splice variants EGFα.

Figure 6B:
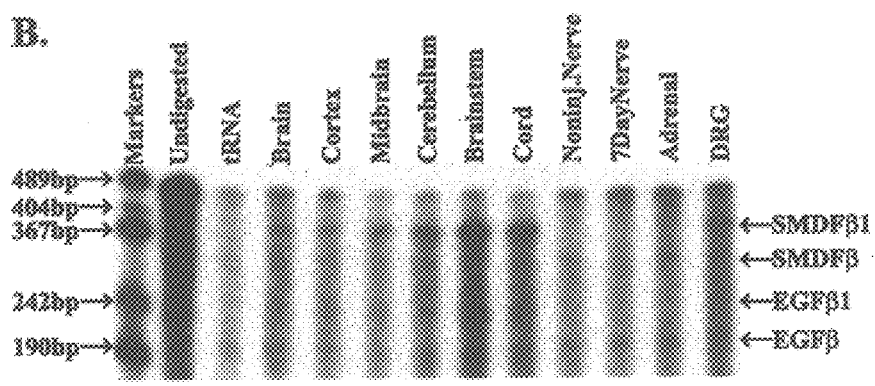

The same probe was used to perform RNAse protection analysis with total cellular RNA from adult rat whole brain, Cortex, Midbrain, Brainstem, Cerebellum, spinal cord, non-injured sciatic nerve, sciatic nerve distal to a site of surgical transection collected 7 days postaxotomy, adrenal gland, and lumbar dorsal root ganglia. These results are shown in FIG. 6B.

EXAMPLE 28
SMDF Expression Non-neural Adult Rat Tissues

Figure 7A:
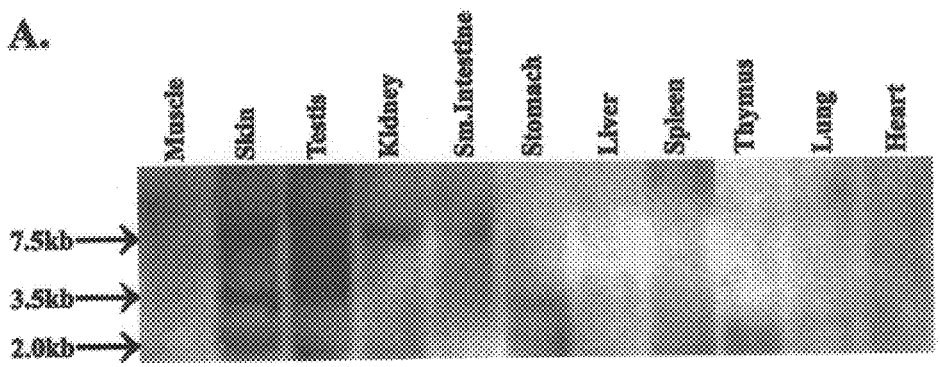
FIGS. 7A and 7B shows distribution of SMDF expression in adult rat tissues analyzed by Northern blot and reverse transcription-polymerase chain reaction analyses.

SMDF expression was analyzed in adult rat tissues by Northern blot and reverse transcription-polymerase chain reaction analyses to determine if any SMDF isoforms were expressed in non-neural tissue. Tissues analyzed included gastrocnemius/soleus muscle, skin from the dorsum of the hindfoot, Testis, Kidney, small intestine, Stomach, Liver, Spleen, Thymus, Lung and Heart. The results of Northern blot analysis with the 1014 bp SMDF-specific probe (FIG. 5) are shown in FIG. 7A. In this prolonged (two week) exposure, bands of estimated at 2.5, 3.5 and 7.5 kb sizes are detected in total cellular RNA from several non-neural tissues, including stomach and testis.

Figure 7B:
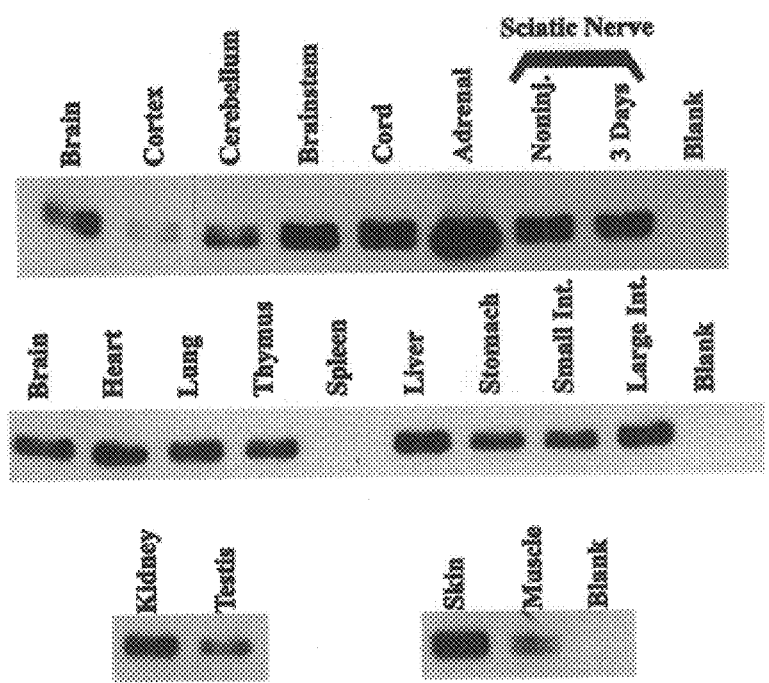

For the reverse transcription-polymerase chain reaction analyses, total cellular RNA from whole adult rat brain, cortex, cerebellum, brainstem, spinal cord, adrenal, sciatic nerve [both Noninjured and distal to a site of surgical transection 3 days after axotomy (3 days distal)], heart, lung, thymus, spleen, liver, stomach, large intestine, kidney, testis, skin from the dorsum of the hind foot, and gastrocnemius/soleus muscle was reverse transcribed and PCR amplified with primers hybridizing to sequences in the SMDF amino terminus and the transmembrane domains. The sequences recognized by these primers are common to all SMDF transmembrane isoforms. The results are shown in FIG. 7B. In these experiments, SMDF transcripts were routinely detected in virtually all tissues in the body except spleen; in some experiments, SMDF mRNA was also detectable in this tissue.

Figure 8:
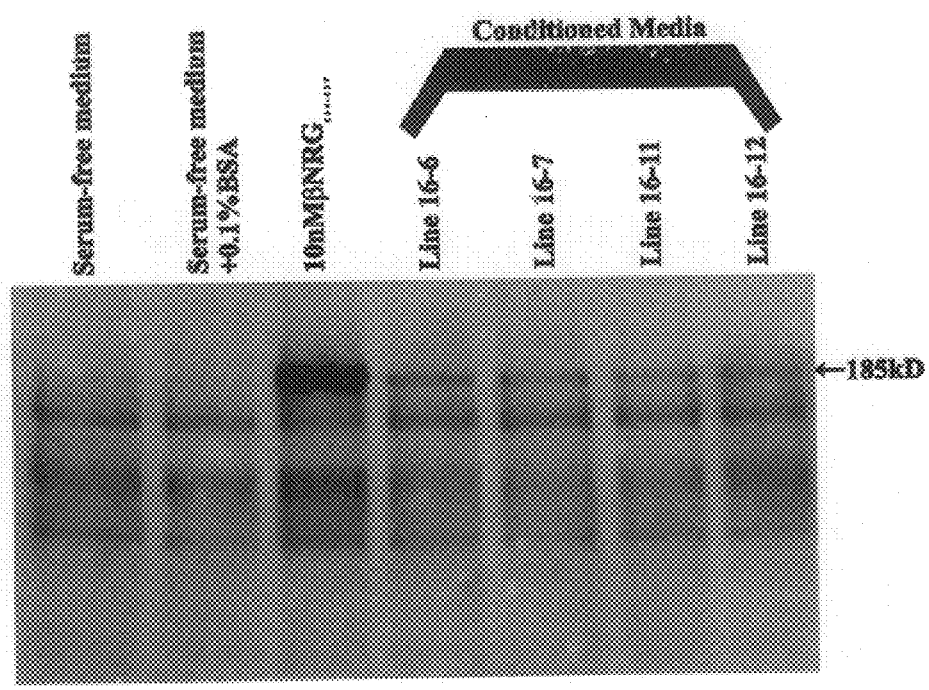
FIG. 8 shows Chinese hamster ovary (CHO) cells expressing SMDF isoforms secrete functional neuregulin into their media. Monolayers of MCF-7 breast carcinoma cells were serum-starved and then challenged for 15 minutes with serum-free medium alone, serum-free media with 0.1% bovine serum albumin (BSA), 10 nM bacterially produced neuregulinβ1$_{168-237}$ or conditioned medium from four CHO cell lines stably transfected with a plasmid directing the expression of SMDFβ1a. Cell lysates were prepared from these lysates, immunoblotted and probed with a rabbit polyclonal antiphosphotyrosine antibody. A 185 kD band was detected in lysates of cells stimulated with neuregulinβ1$_{168-237}$ or media conditioned by each of the four SMDFβ1a expressing cell lines, but not from cells challenged with serum-free medium alone or containing 0.1% BSA.

EXAMPLE 29
Secretion of Functional SMDF Isoforms into the Media of Chinese Hampster Ovary (CHO) Cells Transfection of plasmid pSLC338 into CHO cells resulted in four CHO cell lines expressing SMDFβ1a. To determine if the SMDFβ1a protein produced by these cell lines was functional, monolayers of MCF-7 breast carcinoma cells were serum-starved and then challenged for 15 minutes with serum-free medium alone, serum-free media with 0.1% bovine serum albumin (BSA), 10 nM bacterially produced neuregulinβ$1_{168-237}$ or conditioned medium from the four CHO cell expressing SMDFβ1a. Following this, cell lysates were prepared from the MCF-7 cells, immunoblotted and probed with a rabbit polyclonal antiphosphotyrosine antibody. The results are shown in FIG. 8. A 185 kD band was detected in lysates of cells stimulated with neuregulinβ1$_{168-237}$ or media conditioned by each of the four SMDFβ1a expressing CHO cell lines, but not from cells challenged with serum-free medium alone or media containing 0.1% BSA.

EXAMPLE 30
Sequencing and Characterization of GGFβ1a cDNA (Clone pSLC132)

Initial analyses indicated that the fourth NRG cDNA, clone pSLC132, previously identified in a rat spinal cord library (Carroll et al., 1997) encoded a previously undescribed transmembrane NRG isoform from the GGF subfamily. To establish the structure of the NRG isoform encoded by this clone, the complete sequence of the pSLC132 cDNA was determined.

The largest open reading frame in this 3086 bp cDNA (SEQ ID No.: 20) begins immediately at the 5' end of the sequence and extends to a TAA termination codon at nucleotide 2361 (FIGS. 9A–9D). A comparison between the protein sequence predicted by the pSLC132 cDNA (SEQ ID No.: 21) and sequences currently deposited in GenBank showed a strong similarity to the sequence of human GGFβ3 (Marchionni et al., 1993). The amino terminal sequences of the rat cDNA are highly similar to the carboxy terminal half of the human GGF kringle domain with the exception of an amino acid region in the middle of this region. The predicted protein sequences C-terminal to this kringle domain are identical to those predicted by a rat NDFβ1a cDNA (Wen et al., 1994) and consist (in order) of an immunoglobulin-like domain, a glycosylation "spacer", EGF-like common and b sequences, a hydrophobic transmembrane segment, a cytoplasmic domain common to all NRG transmembrane precursors and an "a" variant carboxy terminus. These potential protein coding sequences are followed by a 722 bp 3' untranslated region which lacks a polyadenylated tract, suggesting that the pSLC132 cDNA does not completely represent the native 3' untranslated region of the corresponding mRNA.

As the amino terminal sequences of the pSLC132 cDNA were apparently incomplete, the inserts from the pSLC132 clone and a near-full length SMDF transmembrane precursor cDNA (see below) were used to screen a rat genomic library, resulting in the isolation of twenty clones hybridizing to these probes. Three of these clones (λRNR24, 25 and 26) specifically hybridized to a probe derived from the kringle domain sequences of pSLC132. A 4.0 kb EcoRI fragment from λRNR26 Containing these hybridizing sequences was subcloned and sequenced. The protein coding sequences of the rat GGF kringle domain are contained within a single exon (FIG. 11A).

EXAMPLE 31
Structural Variability of GGF Splice Variants

Single-stranded cDNA templates were synthesized from polyadenylated RNA isolated from a pool of lumbar dorsal root ganglia and lumbar spinal cord (collected 7 and 10d postaxotomy) and a pool of sciatic nerve distal to a site of surgical transection (16 hr, 3d and 7d postaxotomy). Partial GGF cDNAs were produced using long-distance (LD)-PCR. Although the secreted isoforms (eg. GGFβ3) were generated with a single set of primers, cDNAs encoding GGF transmembrane isoforms (GGFβ2 and GGFβ4) were isolated using nested primer sets using the kringle domain forward oligonucleotide and the common transmembrane domain oligonucleotide. PCR products were cloned into pT7Blue-3 and sequenced as described above. A total of three novel partial cDNA sequences were generated: GGFβ2—SEQ ID No.: 22, GGFβ3—SEQ ID No.: 24, and GGF4—SEQ ID No.: 26). The predicted amino acid sequence are given in SEQ ID No. 23 (GGFβ2), SEQ ID No. 25 (GGFβ3), and SEQ ID No. 26 (GGFβ4).

Figure 11A:
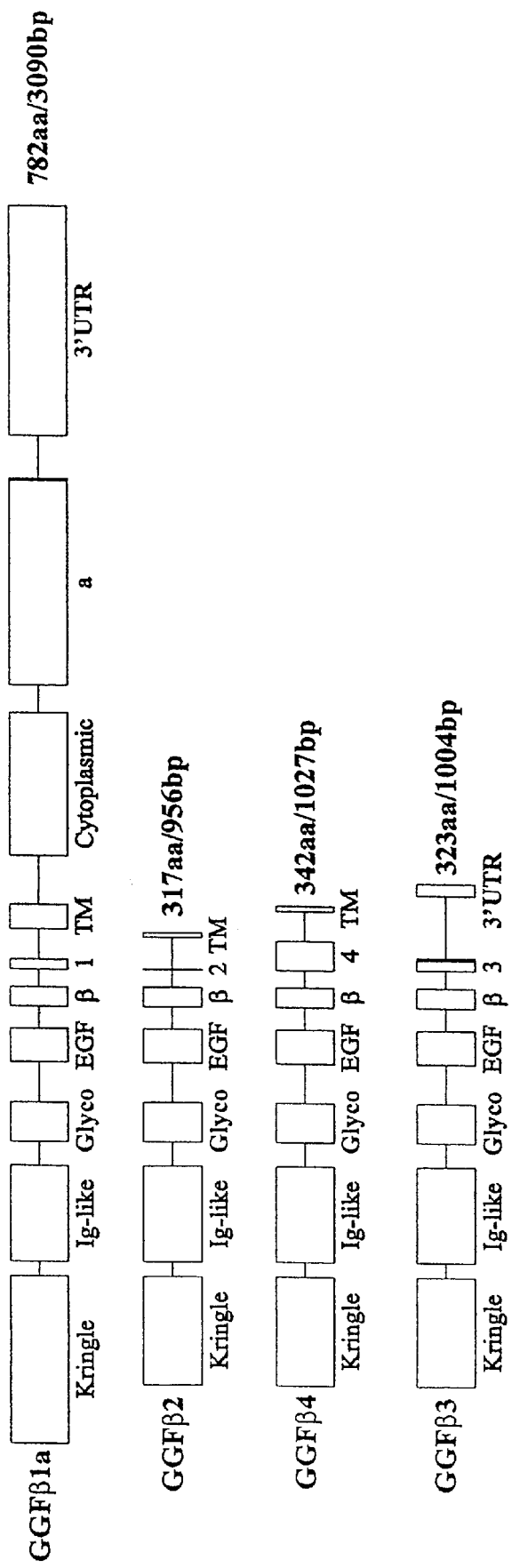

Comparisons of these partial GGF sequences to the GGFβ1a are shown in FIGS. 11A–11C. i.e., shows a comparison of the structure of GGF cDNAs isolated from postaxotomy sciatic nerve, DRG and cord and their encoded proteins. FIG. 11A shows rat GGF structures as predicted from cDNA sequences including the neuregulin EGF-like common domain, the neuregulin β EGF-like variant domain, juxtamembrane domains, the intracellular domain common to all neuregulin transmembrane splice variants, and variant carboxy terminal domains. FIGS. 11B–11C show the alignments of the deduced amino acid sequences of rat GGFβ1a, GGFβ2, GGFβ3 and GGFβ4.

EXAMPLE 32
Analysis of GGF Expression in Adult Rat Tissues

Figure 12:
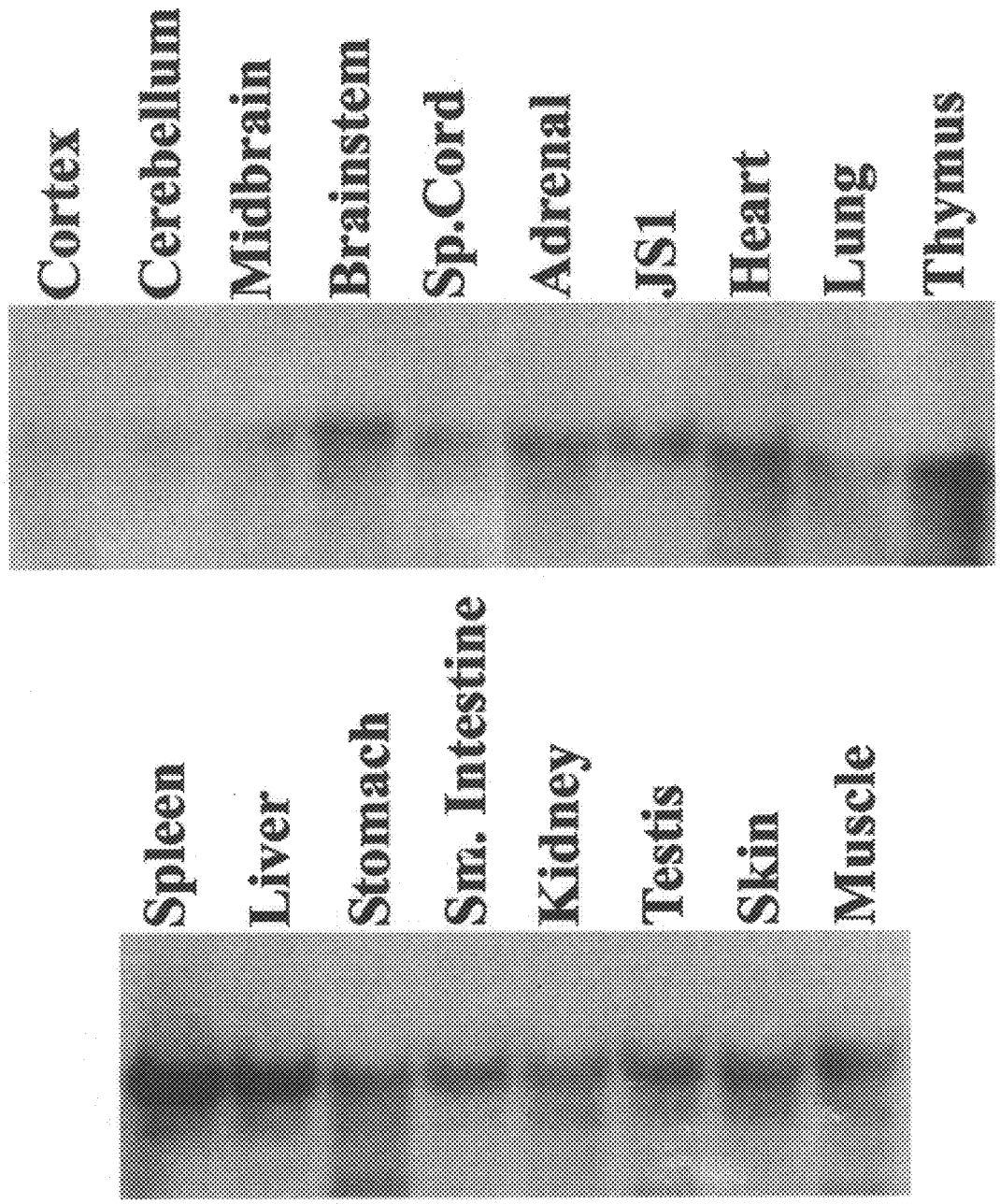
FIG. 12 shows the distribution of GGF expression in adult rat tissues analyzed by Northern blot analysis. 10 μg of total cellular RNA isolated from the indicated tissues was resolved by electrophoresis, blotted and probed with a 432 bp GGF-specific probe encoding a portion of the kringle domain. In this exposure, predominant 2.5–3.0 kb bands are detected in total cellular RNA from both neural and non-neural tissues, albeit with differing levels of expression; longer exposures of these same blots also demonstrate the presence of lesser amounts of larger transcripts (data not shown). Tissues examined include whole adult rat brain (Brain), Cortex, Cerebellum, Midbrain, Brainstem, spinal cord (Sp. Cord), Adrenal, JS1 schwannoma cells (JS1), Heart, Lung, Thymus, Spleen, Liver, Stomach, small intestine (Sm.Intestine), Kidney, Testis, skin from the dorsum of the hind foot (Skin) and gastrocnemius/soleus muscle (Muscle).

FIG. 12 shows a detailed distribution of GGF expression in adult rat tissues analyzed by Northern blot analysis. The GGF expression in adult rat tissues was carefully analyzed by Northern blot, ribonuclease protection, and reverse transcription-polymerase chain reaction analyses. For Northern blot analysis, total cellular RNA isolated from various tissues and JS1 schwannoma cells was resolved by electrophoresis, blotted, and probed with the 1014 bp probe. The probe detects RNA of the expected size in the JS1 schwannoma control. In this long (two week) exposure, bands of differing sizes are also detected in total cellular RNA from non-neural tissues, including stomach and testis.

For the ribonuclease protection experiment, total cellular RNA isolated from the various tissues and JS1 schwannoma cells is hybridized to the antisense riboprobe.

Reverse transcription-polymerase chain reaction analyses was performed by amplifying total cellular RNA from whole adult rat brain, cortex, cerebellum, brainstem, spinal cord, adrenal, sciatic nerve [both Noninjured and distal to a site of surgical transection 3 days after axotomy (3 days distal)], heart, lung, thymus, spleen, liver, stomach, large intestine, kidney, testis, skin from the dorsum of the hind foot and gastrocnemius/soleus muscle with primers hybridizing to sequences in the amino terminus and the transmembrane domains of the GGF's.

EXAMPLE 33
In situ Hybridization Analysis of GGF Expression

A sciatic nerve, lumbar DRG, and the lumbar enlargement of the spinal cord were surgically transected from anesthetized adult male Harlan Sprague-Dawley rats. The tissues were fixed and eight micron cryosections were prepared as previously described (Carroll et al., 1992). Sense and antisense $^{33}$P-labeled riboprobes were transcribed from plasmids pSLC123 (encoding NRG EGF-like common, EGF-like β and 1 juxtamembrane domains) and pSLC111 (encoding the NRG immunoglobulin-like domain) and in situ hybridizations were performed.

EXAMPLE 34
Secretion of Functional GGF Isoforms

Chinese hamster ovary (CHO) cells expressing GGF isoforms secrete functional NRG into their media. Monolayers of MCF-7 breast carcinoma cells were serum-starved and then challenged for 15 minutes with serum-free medium alone, serum-free media with 0.1% bovine serum albumin (BSA), 10 nM bacterially produced NRGβ1$_{168-237}$ or conditioned medium from four cell lines stably transfected with plasmids directing the expression of either GGFβ1a or GGFβ3. Cell lysates were prepared from these lysates, immunoblotted and probed with a rabbit polyclonal antiphosphotyrosine anti body. A 185 kD band was detected in lysates of cells stimulated with NRGβ1$_{168-237}$ or media conditioned by each of the GGF expressing cell lines, but not from cells challenged with serum-free medium alone or containing 0.1% BSA. GGF expression plasmids for GGFβ1a or GGFβ3 were transfected into a CHO line, and cell lines stably transfected with the plasmids were selected. Medium from each cell lines was tested for the presence of functional GGF isoforms using the same MCF-7 assay as was used to detect functional SMDFβ1a. Monolayers of MCF-7 breast carcinoma cells were serum-starved and then challenged for 15 minutes with serum-free medium alone, serum-free media with 0.1% bovine serum albumin (BSA), 10 nM bacterially produced NRGβ1$_{168-237}$ or conditioned medium from four cell lines stably expressing GGFβ1a or GGFβ3. Cell lysates were prepared from these lysates, immunoblotted and probed with a rabbit polyclonal antiphosphotyrosine antibody. A 185 kD band was detected in lysates of cells stimulated with NRGβ1$_{168-237}$ or media conditioned by each of the GGF expressing cell lines, but not from cells challenged with serum-free medium alone or containing 0.1% BSA.

EXAMPLE 35

Comparison of the Structures of SMDF and GGF Neuregulins

In spite of the structural complexity of the NRGs, all of these proteins share an EGF-like domain. The EGF-like domain, which consists of a common region fused to either α- or β-domains, is essential for biologic activity. Truncated β-NRG molecules containing only the EGF-like domain bind to the NRG receptor with an affinity similar to that of the full-length factor (Holmes et al., 1992; Peles et al., 1993) and are capable of inducing a variety of biologic responses (Holmes et al., 1992; Peles et al., 1993; Chu et al., 1995; Levi et al., 1995; Syroid et al., 1996). In spite of their similar structures, NRG α and β EGF-like domains are not functionally equivalent; β-NRGs have an affinity for erbB receptors an order of magnitude greater than α-NRGs (Wen et al., 1994). Furthermore, α-NRGs are nonmitogenic for some, but not all, cell types which proliferate in response to β-NRGs (Pinkas-Kramarski et al., 1996).

Other domains within the neuregulins are also structurally and functionally variable. In addition to the unique amino termini noted above (for which functions are currently unknown), the mesenchymal and GGF (but not the SMDF) neuregulin subfamilies contain an immunoglobulin-like domain (Ben-Baruch and Yarden, 1994; Peles and Yarden, 1993; Ho et al., 1995) mediating NRG interactions with cell surface glycoproteins, with resultant concentration and specific localization of the factor (Sudhalter et al., 1996). Splice variants in the GGF and mesenchymal neuregulin subfamilies also may contain serine and threonine-rich spacer domains which serve as the site of o- and n-linked glycosylation (Wen et al., 1994; Carroll et al., 1997); this glycosylation is non-essential for biologic activity and the precise function(s) of this region is as yet unknown.

NRGs may be synthesized as either transmembrane precursors or directly secretable forms. This distinction depends upon the juxtamembrane domain, which is immediately C terminal to the EGF-like domain. Four juxtamembrane domains, designated 1 to 4, have been identified in the rat. In this regard, the '3' juxtamembrane domain is notable in that it, unlike other juxtamembrane domains, contains a termination codon, thus leading to truncation of the factor and synthesis in a directly secretable form. In all other NRG isoforms, the juxtamembrane domain is followed by a transmembrane domain which anchors the factor in the cell membrane and is itself coupled to one of three possible cytoplasmic domains (designated a, b, and c) (Wen et al., 1994). The cytoplasmic domains are highly conserved between species, suggesting an essential function (Wen et al., 1994); indeed, it has been recently reported that neuregulin cytoplasmic domains bind LIM kinase 1, suggesting that NRG transmembrane precursors are capable of transmitting signals into the interior of the cell synthesizing these proteins (Wang et al., 1998).

Discussion

The neuregulins and their erbb receptors are widely expressed in the developing and adult nervous system, suggesting that these molecules perform multiple essential functions in the brain and associated tissues. Neuregulins act on both CNS and PNS glia, although their actions on Schwann cells are at present better defined. The neuregulins have been implicated as neuronally synthesized, axon-associated signals influencing Schwann cell differentiation, survival and proliferation at multiple stage s in their development. Neuregulins direct neural crest cell differentiation into Schwann cells (Shah et al., 1994) and act on the Schwann cell precursor, an intermediate cell type arising from neural crest cells. Schwann cell precursors undergo apoptosis if not in contact with axons; neuregulins prevent axotomy-induced apoptosis of both Schwann cell precursors and neonatal Schwann cells surrounding neuromuscular junctions (Dong et al., 1995; Lee et al., 1995; Marchionni, 1995; Trachtenberg and Thompson, 1996; Lee et al., 1995; Marchionni, 1995; Trachtenberg and Thompson, 1996). Furthermore, neuregulins and erbB2 represent components of the "axon-associated mitogen" associated with neonatal sensory neuron axons (Morrissey et al., 1995), an observation consistent with the ability of members of the GGF and mesenchymal neuregulin subfamilies to stimulate proliferation of neonatal Schwann cells in vitro (Porter et al., 1986; Raff et al., 1978; Raabe et al., 1996).

Considered together, these observations have led to the concept of neuregulins as an axon-associated factor influencing Schwann cell differentiation, survival and proliferation during development (Lemke, 1996; Topilko et al., 1996; Lemke, 1996). However, this hypothesis may have to be modified in light of the finding that neonatal rat Schwann cells synthesize and secrete neuregulins in vitro (Raabe et al., 1996). Furthermore, Schwann cell expression of neuregulins is induced in adult rat sciatic nerve following axotomy (Carroll et al., 1997).

Neuregulins expressed by CNS neurons may also act as axon-associated factors regulating oligodendrocyte differentiation and survival (Vartanian et al., 1997). Both ARIA and GGF neuregulin isoforms act on developing oligodendrocytes, although the reported effects of these two isoforms differ from one another. ARIA acts to enhance oligodendrocyte differentiation from O2A progenitor cells without promoting proliferation (Vartanian et al., 1994). In contrast, Canoll et al. (Canoll et al., 1996) have reported that GGF inhibits differentiation and lineage commitment of oligodendroglial progenitors while acting as a mitogen for pro-oligodendrocytes, oligodendrocytes and type-2 astrocytes. Additionally, neonatal oligodendrocytes can be rescued from an apoptotic death by β- or α-neuregulin isoforms (Raabe et al., 1997). However, in an interesting parallel to the findings described above for Schwann cells, cultured oligodendrocytes have also been found to be capable of secreting neuregulin proteins themselves (Raabe et al., 1997). It is thus apparent that this class of glial cells is also capable of both responding to and secreting neuregulins.

Neuregulins have multiple actions on developing neurons, some of which are the result of direct actions of neuregulins on these cells and others which are indirectly mediated by neighboring glia. Verdi et al (Verdi et al., 1996) have demonstrated that the survival and development of sympathetic neuroblasts is indirectly mediated by neuronally produced neuregulin which is released, subsequently stimulating neurotrophin-3 release from adjacent ganglionic satellite cells. Neuregulins also promote maintenance and elongation of radial glia in the developing cortex (Anton et al., 1997) and cerebellum (Rio et al., 1997) and stimulate neuroblast migration along these glia.

Neuregulins may influence neuronal morphology and synaptic function. The GGFβ3 neuregulin isoform promotes survival and neurite extension in cultures of embryonic and neonatal rat retinal neurons (Bermingham-McDonogh et al., 1996). Neuregulins also stimulate functional expression of calcium-activated potassium channels in developing chick parasympathetic neurons (Subramony and Dryer, 1997) and increase neuronal expression of neurotransmitter receptors including NMDA (Ozaki et al., 1997) and nicotinic acetylcholine (Yang et al., 1998) receptor subunits. Although in some of these examples it is still unclear whether in vitro neuregulin effects result from neuregulins acting directly through the erbB receptors widely expressed by neurons throughout the nervous system (Pinkas-Kramarski et al., 1997; Burden and Yarden, 1997) or are mediated indirectly by contaminating glia, it is nonetheless clear that these factors have profound effects on multiple aspects of neuronal biology.

To test this hypothesis, it is necessary to first understand the range of structural and functional diversity of neuregulin isoforms expressed by neurons and glia. This study was therefore performed as an initial assessment of the structural and functional heterogenity of the SMDF subfamily, the predominant neuregulin isoforms expressed in many regions of the nervous system. It was previously reported that SMDF transcripts are undetectable in Northern blots of total cytoplasmic RNA isolated from noninjured adult rat sciatic nerve and sciatic nerve 7 days postaxotomy (Carroll et al., 1997). However, Ratner and colleagues subsequently found that SMDF mRNA is detectable in early postnatal rat sciatic nerve using highly sensitive RT-PCR analyses (Rosenbaum et al., 1997). These observations, considered together with the isolation of SMDF cDNAs from the JS1 schwannoma cell line described herein (see above), raise the question of whether earlier failures to detect SMDF mRNA in noninjured or axotomized adult peripheral nerve could be the result of the relative insensitivity of Northern blot analyses with total cytoplasmic RNA.

The following reference were cited herein:
Anton, et al., (1997). Development 124, 3501–3510.
Ben-Baruch, et al., (1994). Proceedings of the Society for Experimental Biology and Medicine 206, 221–227.
Bermingham-McDonogh, et al., (1996). Development 122, 1427–1438.
Brockes, et al., (1979). Brain Res. 165, 105–118.
Brockes, et al., (1980). J.Biol.Chem. 255, 8374–8377.
Burden, S. and Yarden, Y. (1997). Neuron 18, 847–855.
Canoll, et al., (1996). Neuron 17, 229–243.
Carroll, et al., (1998). J.Neuropath.Exp.Neurol. 57, 915–929.
Carroll, et al.,. (1997). J.Neurosci. 17, 1642–1659.
Carroll, et al., (1992). Neuron 9, 779–788.
Chen, C. and Okayama, H. (1987). Mol.Cell.Biol. 7, 2745–2752.
Chen, et al., (1994). J.Comp.Neurol. 349, 389–400.
Cheng, L. and Mudge, A. W. (1996). Neuron 16, 309–319.
Chomczynski, P. and Sacchi, N. (1987). Analyt.Biochem. 162, 156–159.
Chu et al., (1995). Neuron 14, 329–339.
Dong, et al., (1995). Neuron 15, 585–596.
Falls, et al., (1993). Cell 72, 801–815.
Fawcett, et al., (1990). Ann.Rev.Neurosci. 13, 43–60.
Feinberg, A. P. and Vogelstein, B. (1984). Anal.Biochem. 67, 15–28.
Fu, S. Y. and Gordon, T. (1997). Molec.Neurobiology 14, 67–116.
Goodearl, et al., (1993). J.Biol.Chem. 268, 18095–18102.
Gubler, U. and Hoffman, B. J. (1983). Gene 25, 263–269.
Hall, et al., (1977). Neuropathol.Appl.Neurobiol. 3, 65–78.
Ho, et al., (1995). J.Biol.Chem. 270, 14523–14532.
Holmes, et al., (1992). Science 256, 1205–1210.
Kyte, J. and Doolittle, R. F. (1982). J.Mol.Biol. 157, 105–132.
Lee, et al., (1995). Nature 378, 394–398.
Lemke, G. (1996). Mol.Cell.Neurosci. 7, 247–262.
Levi, et al., (1995). J.Neurosci. 15, 1329–1340.
Maniatis, et al., (1990). Molecular Cloning: A Laboratory Manual (Cold Spring Harbor, N.Y.: Cold Spring Harbor Laboratory Press).
Marchionni, M. A. (1995). Nature 378, 334–335.
Marchionni, et al., (1993). Nature 362, 312–318.
Marikovsky, et al., (1995). Oncogene 10, 1403–1411.
McArthur, J. G. and Stanners, C. P. (1991). J.Biol.Chem. 266, 6000–6005.
Morrissey, et al., (1995). Proc.Natl.Acad.Sci.USA 92, 1431–1435.
Nadim, et al., (1990). Neuropathol.Appl.Neurobiol. 16, 411–421.
Ozaki, et al., (1997). Nature 390, 691–694.
Peles, et al., (1993). EMBO J. 12, 961–971.
Peles, E. and Yarden, Y. (1993). Bioessays 15, 815–824.
Pellegrino, et al., (1986). J.Neurocytol. 15, 17–28.
Pinkas-Kramarski, et al., (1997). Oncogene 15, 2803–2815.
Pinkas-Kramarski, et al., (1996). J.Biol.Chem. 271, 19029–19032.
Porter, et al., (1986). J.Neurosci. 6, 3070–3078.
Raabe, et al.,. (1996). J.Neurosci.Res. 46, 263–270.
Raabe, T et al., (1997). J.Neurochem. 69, 1859–1863.
Raabe, et al., (1997). J.Neurosci.Res. 50, 755–768.
Raff, et al., (1978). Schwann cell growth factors. Cell 15, 813–822.
Rio, C., Rieff, H. I., Qi, P., and Corfas, G. (1997). Neuron 19, 39–50.
Rosenbaum, et al., (1997). Exp.Neurol. 148, 604–615.
Schubert, et al., (1974). Nature 249, 224–227.
Shah, et al., (1994). Cell 77, 349–360.
Subramony, et al., (1997). Proc.Natl.Acad.Sci.USA 94, 5934–5938.
Sudhalter, et al., (1996). Glia 17, 28–38.
Syroid, et al., (1996). Proc.Natl.Acad.Sci.USA 93, 9229–9234.
Topilko, et al., (1996). Mol.Cell.Neurosci. 8, 71–75.
Trachtenberg, J. T. and Thompson, W. J. (1996). Nature 379, 174–177.
Vartanian, et al., (1994). Proc.Natl.Acad.Sci.USA 91, 11626–11630.
Vartanian et al., (1997). J.Cell Biol. 137, 211–220.
Verdi, et al., (1996). Neuron 16, 515–527.

Wang, et al., (1998). J.Biol.Chem. 273, 20525–20534.
Wen, et al., (1992). Cell 69, 559–572.
Wen, et al., (1994). Molecular and Cellular Biology 14, 1909–1919.
Yang, et al., (1998). Neuron 20, 255–270.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated splice variant isoform of sensory and motor neuron-derived factor (SMDF) SMDFβ1a protein having an amino acid sequence of SEQ ID No 2.

2. A method of treating a condition involving nervous system dysfunction, comprising the step of:

administering an effective dose of neuregulin SMDFβ1a.

3. The method of claim 2, wherein said condition is a demyelinating disease.

4. The method of claim 3, wherein said demyelinating disease is multiple sclerosis.

5. The method of claim 2, wherein said condition comprises of nerve damage.

6. The method of claim 5, wherein said nerve damage is selected from the group consisting of spinal cord injury, spinal cord neuropathy, peripheral nerve injury, and peripheral nerve nueropathy.

* * * * *

SEQUENCE LISTING

<160> NUMBER OF SEQ ID NOS: 27

<210> SEQ ID NO 1
<211> LENGTH: 2856
<212> TYPE: DNA
<213> ORGANISM: Rattus norvegicus
<220> FEATURE:
<222> LOCATION:
<223> OTHER INFORMATION: Nucleotide sequence SMDF
      (1a cDNA (from clone pSLC135)

<400> SEQUENCE: 1

```
gaattcggca cgaggcgatg ctcagagggc aggcacctgc tgctctgtaa tgattcagcc      60
tctttcagcc gctgcgttaa cacgacagga tgctgttgct actgtcgctg ctgcctctcc     120
tgccgccgcc gctgctgccg ccgccgcctc ctctggtctt gcttttgctt ttacttctcc     180
tgcatgacag ttgttttctt cctctaagca gacaccagct tcagacgctt gaggtgagaa     240
acatgccttt cagtttggga tactggttta cttaatcggc taggcggcag cttgcttcct     300
attttggtcc cctgccttct tgaccaaccc ggcatggttt ggagaagcat tgaaagaac      360 tgaaaaagtg tcccagaaac aacagctcaa gatatttcgg tacacttcta tttcatagtt     420
gctagaagcc cttctttttt cgtttttttt ttcttttttct ttttcttttt cttttcctt     480 ttcctgcttc ctcctaagct ctggtacttt gggtaattgc cttggacttg ggtgccttat     540
cgatttcccc ctccaagatg ctgtatcatt tggttggggg gagctctgcg tggtaatgca     600
ctgtgagaga ggccaggcct tctggaggtg agccgatgga gatttattcc ccagacatgt     660
ctgaggtagc tggcgggagg tcctccagcc cctccactca gctgagtgca gccccatctc     720
ttgatgggct tccggcagcg gaggaacata taccagacac ccacacagaa gatgagagaa     780
gccctggact cctgggcctg gcggtgccct gctgtgtgtg cctggaagct gagcgcctga     840
gagggtgtct caactccgag aagatctgca ttgttcccat tctggcttgc ctagtcagcc     900
tctgcctctg cattgctggc ctgaagtggg tatttgtgga caagatattt gaatacgact     960
ctcctaccca ccttgaccct ggggggttag gccaggaccc tgtgatttct ctggatccaa    1020
ctgctgcccc agccattttg gtatcatctg aggcatacac ttcacctgtc tctaaggctc    1080
agtctgaagc tggggctcat gttacagtac aaggtgacca tgctgctgtg gcctctgaac    1140
cttcagcagt accgacccgg aagaaccggc tgtctgcttt tcctcccttt cactctactg    1200
caccgccctt cccttctcca gctcggaccc ctgaggtgag aacacccaag tcaggaactc    1260
agccacaaac aacagaaact aacctgcaaa ctgctcctaa actttccaca tcgacatcca    1320
cgactgggac cagccatctc ataaagtgcg cggagaagga gaaactttc tgtgtgaatg     1380 ggggcgagtg cttcacggtg aaggacctgt caaacccgtc aagatacttg tgcaagtgcc    1440
```

-continued

```
caaatgagtt tactggtgat cgttgccaaa actacgtaat ggccagcttc tacaagcatc  1500
ttgggattga atttatggaa gcggaggaac tctaccagaa gagggtgctg acaattactg  1560
gcatctgtat cgccctgctg gtggtcggca tcatgtgtgt ggtggcctac tgcaaaacca  1620
agaagcagcg gcagaagctt catgatcggc ttcggcagag tcttcggtca gaacggagca  1680
acctggtgaa catagcgaat gggcctcacc acccaaaccc gccgccagag aacgtgcagc  1740
tggtgaatca atacgtatct aaaaacgtca tctccagtga gcatattgtt gagagagaag  1800
tggagacttc ctttttccacc agtcattaca cttccacagc ccatcactcc acgactgtca  1860
cccagactcc tagtcacagc tggagtaatg ggcacacgga gagcgtcatt tcagaaagca  1920
actccgtaat catgatgtct tcggtagaga acagcaggca cagcagtccc gccgggggcc  1980
cacgaggacg tcttcatggc ctgggaggcc ctcgtgataa cagcttcctc aggcatgcca  2040
gagaaacccc tgactcctac agagactctc ctcatagcga aaggtatgta tcagccatga  2100
ccaccccggc tcgtatgtca cctgtagatt tccacacgcc aagctcccct aaatcgcccc  2160
cttcggaaat gtctccaccc gtgtccagca tgacggtgtc catgccctct gtggcagtca  2220
gcccctttgt ggaagaagag aggcctctgc tgcttgtgac gccaccaagg ctacgggaga  2280
agaaatatga tcatcacccc cagcaactca actcctttca tcacaaccct gcacatcaga  2340
gtaccagcct ccccctagc ccactgagga tagtggagga tgaggagtac gagacgaccc  2400
aggagtatga gtcagttcaa gagcccgtta agaaagtcac caatagccgg cgggccaaaa  2460
gaaccaagcc caatggccac attgccaata ggttggaaat ggacagcaac acaagttctg  2520
tgagcagtaa ctcagaaagt gagacagaag acgaaagagt aggtgaagac acaccattcc  2580
tgggcataca gaaccccctg gcagccagcc ttgaggtggc ccccgccttc cgtctggctg  2640
agagcaggac taacccagca ggccgcttct ccacacagga ggaattacag gccaggctgt  2700
ctagtgtaat cgctaaccaa gaccctattg ctgtataaaa cctaaataaa cacatagatt  2760
cacctgtaaa actttatttt atataataaa gtatttcacc ttaaattaaa caatttattt  2820
tattttagca gttctgcaaa tactcgtgcc gaattc                           2856
```

<210> SEQ ID NO 2
<211> LENGTH: 700
<212> TYPE: PRT
<213> ORGANISM: Rattus norvegicus
<220> FEATURE:
<223> OTHER INFORMATION: Amino acid sequence of SMDF(1a (encoded by clone pSLC135)

<400> SEQUENCE: 2

```
Met Glu Ile Tyr Ser Pro Asp Met Ser Glu Val Ala Gly Gly Arg
                5                  10                  15

Ser Ser Ser Pro Ser Thr Gln Leu Ser Ala Ala Pro Ser Leu Asp
                20                  25                  30

Gly Leu Pro Ala Ala Glu Glu His Ile Pro Asp Thr His Thr Glu
                35                  40                  45

Asp Glu Arg Ser Pro Gly Leu Leu Gly Leu Ala Val Pro Cys Cys
                50                  55                  60

Val Cys Leu Glu Ala Glu Arg Leu Arg Gly Cys Leu Asn Ser Glu
                65                  70                  75

Lys Ile Cys Ile Val Pro Ile Leu Ala Cys Leu Val Ser Leu Cys
                80                  85                  90

Leu Cys Ile Ala Gly Leu Lys Trp Val Phe Val Asp Lys Ile Phe
                95                  100                 105
```

-continued

```
Glu Tyr Asp Ser Pro Thr His Leu Asp Pro Gly Gly Leu Gly Gln
            110                 115                 120

Asp Pro Val Ile Ser Leu Asp Pro Thr Ala Ala Pro Ala Ile Leu
            125                 130                 135

Val Ser Ser Glu Ala Tyr Thr Ser Pro Val Ser Lys Ala Gln Ser
            140                 145                 150

Glu Ala Gly Ala His Val Thr Val Gln Gly Asp His Ala Ala Val
            155                 160                 165

Ala Ser Glu Pro Ser Ala Val Pro Thr Arg Lys Asn Arg Leu Ser
            170                 175                 180

Ala Phe Pro Pro Phe His Ser Thr Ala Pro Pro Phe Pro Ser Pro
            185                 190                 195

Ala Arg Thr Pro Glu Val Arg Thr Pro Lys Ser Gly Thr Gln Pro
            200                 205                 210

Gln Thr Thr Glu Thr Asn Leu Gln Thr Ala Pro Lys Leu Ser Thr
            215                 220                 225

Ser Thr Ser Thr Thr Gly Thr Ser His Leu Ile Lys Cys Ala Glu
            230                 235                 240

Lys Glu Lys Thr Phe Cys Val Asn Gly Gly Glu Cys Phe Thr Val
            245                 250                 255

Lys Asp Leu Ser Asn Pro Ser Arg Tyr Leu Cys Lys Cys Pro Asn
            260                 265                 270

Glu Phe Thr Gly Asp Arg Cys Gln Asn Tyr Val Met Ala Ser Phe
            275                 280                 285

Tyr Lys His Leu Gly Ile Glu Phe Met Glu Ala Glu Glu Leu Tyr
            290                 295                 300

Gln Lys Arg Val Leu Thr Ile Thr Gly Ile Cys Ile Ala Leu Leu
            305                 310                 315

Val Val Gly Ile Met Cys Val Val Ala Tyr Cys Lys Thr Lys Lys
            320                 325                 330

Gln Arg Gln Lys Leu His Asp Arg Leu Arg Gln Ser Leu Arg Ser
            335                 340                 345

Glu Arg Ser Asn Leu Val Asn Ile Ala Asn Gly Pro His His Pro
            350                 355                 360

Asn Pro Pro Pro Glu Asn Val Gln Leu Val Asn Gln Tyr Val Ser
            365                 370                 375

Lys Asn Val Ile Ser Ser Glu His Ile Val Glu Arg Glu Val Glu
            380                 385                 390

Thr Ser Phe Ser Thr Ser His Tyr Thr Ser Thr Ala His His Ser
            395                 400                 405

Thr Thr Val Thr Gln Thr Pro Ser His Ser Trp Ser Asn Gly His
            410                 415                 420

Thr Glu Ser Val Ile Ser Glu Ser Asn Ser Val Ile Met Met Ser
            425                 430                 435

Ser Val Glu Asn Ser Arg His Ser Ser Pro Ala Gly Gly Pro Arg
            440                 445                 450

Gly Arg Leu His Gly Leu Gly Gly Pro Arg Asp Asn Ser Phe Leu
            455                 460                 465

Arg His Ala Arg Glu Thr Pro Asp Ser Tyr Arg Asp Ser Pro His
            470                 475                 480

Ser Glu Arg Tyr Val Ser Ala Met Thr Thr Pro Ala Arg Met Ser
            485                 490                 495
```

```
Pro Val Asp Phe His Thr Pro Ser Ser Pro Lys Ser Pro Pro Ser
                500                 505                 510

Glu Met Ser Pro Val Ser Ser Met Thr Val Ser Met Pro Ser
        515                 520                 525

Val Ala Val Ser Pro Phe Val Glu Glu Arg Pro Leu Leu Leu
            530                 535                 540

Val Thr Pro Pro Arg Leu Arg Glu Lys Lys Tyr Asp His His Pro
                545                 550                 555

Gln Gln Leu Asn Ser Phe His His Asn Pro Ala His Gln Ser Thr
                560                 565                 570

Ser Leu Pro Pro Ser Pro Leu Arg Ile Val Glu Asp Glu Tyr
            575                 580                 585

Glu Thr Thr Gln Glu Tyr Glu Ser Val Gln Glu Pro Val Lys Lys
                590                 595                 600

Val Thr Asn Ser Arg Arg Ala Lys Arg Thr Lys Pro Asn Gly His
                605                 610                 615

Ile Ala Asn Arg Leu Glu Met Asp Ser Asn Thr Ser Ser Val Ser
                620                 625                 630

Ser Asn Ser Glu Ser Glu Thr Glu Asp Glu Arg Val Gly Glu Asp
                635                 640                 645

Thr Pro Phe Leu Gly Ile Gln Asn Pro Leu Ala Ala Ser Leu Glu
                650                 655                 660

Val Ala Pro Ala Phe Arg Leu Ala Glu Ser Arg Thr Asn Pro Ala
                665                 670                 675

Gly Arg Phe Ser Thr Gln Glu Glu Leu Gln Ala Arg Leu Ser Ser
                680                 685                 690

Val Ile Ala Asn Gln Asp Pro Ile Ala Val
                695                 700

<210> SEQ ID NO 3
<211> LENGTH: 296
<212> TYPE: PRT
<213> ORGANISM: Homo sapiens
<220> FEATURE:
<223> OTHER INFORMATION: Amino acid sequence of human SMDF(3

<400> SEQUENCE: 3

Met Glu Ile Tyr Ser Pro Asp Met Ser Glu Val Ala Ala Glu Arg
                5                   10                  15

Ser Ser Ser Pro Ser Thr Gln Leu Ser Ala Asp Pro Ser Leu Asp
                20                  25                  30

Gly Leu Pro Ala Ala Glu Asp Met Pro Glu Pro Gln Thr Glu Asp
                35                  40                  45

Gly Arg Thr Pro Gly Leu Val Gly Leu Ala Val Pro Cys Cys Ala
                50                  55                  60

Cys Leu Glu Ala Glu Arg Leu Arg Gly Cys Leu Asn Ser Glu Lys
                65                  70                  75

Ile Cys Ile Val Pro Ile Leu Ala Cys Leu Val Ser Leu Cys Leu
                80                  85                  90

Cys Ile Ala Gly Leu Lys Trp Val Phe Val Asp Lys Ile Phe Glu
                95                  100                 105

Tyr Asp Ser Pro Thr His Leu Asp Pro Gly Gly Leu Gly Gln Asp
                110                 115                 120

Pro Ile Ile Ser Leu Asp Ala Thr Ala Ala Ser Ala Val Trp Val
                125                 130                 135
```

```
Ser Ser Glu Ala Tyr Thr Ser Pro Val Ser Arg Ala Gln Ser Glu
                140                 145                 150

Ser Glu Val Gln Val Thr Val Gln Gly Asp Lys Ala Val Val Ser
                155                 160                 165

Phe Glu Pro Ser Ala Ala Pro Thr Pro Lys Asn Arg Ile Phe Ala
                170                 175                 180

Phe Ser Phe Leu Pro Ser Thr Ala Pro Ser Phe Pro Ser Pro Thr
                185                 190                 195

Arg Asn Pro Glu Val Arg Thr Pro Lys Ser Ala Thr Gln Pro Gln
                200                 205                 210

Thr Thr Glu Thr Asn Leu Gln Thr Ala Pro Lys Leu Ser Thr Ser
                215                 220                 225

Thr Ser Thr Thr Gly Thr Ser His Leu Val Lys Cys Ala Glu Lys
                230                 235                 240

Glu Lys Thr Phe Cys Val Asn Gly Gly Glu Cys Phe Met Val Lys
                245                 250                 255

Asp Leu Ser Asn Pro Ser Arg Tyr Leu Cys Lys Cys Pro Asn Glu
                260                 265                 270

Phe Thr Gly Asp Arg Cys Gln Asn Tyr Val Met Ala Ser Phe Tyr
                275                 280                 285

Ser Thr Ser Thr Pro Phe Leu Ser Leu Pro Glu
                290                 295

<210> SEQ ID NO 4
<211> LENGTH: 2540
<212> TYPE: DNA
<213> ORGANISM: Rattus norvegicus
<220> FEATURE:
<221> NAME/KEY: CDS
<222> LOCATION: 370..2458
<223> OTHER INFORMATION: SMDF_2a amino acid sequence

<400> SEQUENCE: 4
gaattcggca cgaggcggca gcttgcttcc tattttggtc ccctgccttc ttgaccaacc      60
cggcatggtt tggagaagca tttgaaagaa ctgaaaaagt gtcccagaaa caacagctca    120
agatatttcg gtacacttct atttcatagt tgctagaagc cctttctttt ttcgtttttt    180
ttttttcttt ttcttttttct ttttcttttt cctttttcctg cttcctccta agctctggta   240
ctttgggtaa ttgccttgga cttgggtgcc ttatcgattt cccccctccaa gatgctgtat   300 catttggttg gggggagctc tgcgtggtaa tgcactgtga gagaggccag gccttctgga    360
ggtgagccga tggagattta ttccccagac atgtctgagg tagctggcgg gaggtcctcc    420
agcccctcca ctcagctgag tgcagttcca tctcttgatg ggcttccggc agcggaggaa    480
catataccag acacccacac agaagatgag agaagccctg gactcctggg cctggcggtg    540
ccctgctgtg tgtgcctgga agctgagcgc ctgagagggt gtctcaactc gagaagatc     600 tgcattgttc ccattctggc ttgcctagtc agcctctgcc tctgcattgc tggcctgaag    660
tgggtatttg tggacaagat atttgaatac gactctccta cccaccttga ccctggggg     720 ttaggccagg accctgtgat ttctctggat ccaactgctg ccccagccat tttggtatca    780
tccgaggcat acacttcacc tgtctctaag gtcagtctg aagctgggc tcatgttaca     840 gtacaaggtg accatgctgc tgtggcctct gaaccttcag cagtaccgac ccggaagaac    900
cggctgtctc ctttttcctcc ctttcaccct actgcaccgc ccttcccttc tccagctcgg    960 accctgagg tgagaacacc caagtcagga actcagccac aaacaacaga aactaacctg   1020
```

-continued

```
caaactgctc ctaaactttc cacatcaaca tccacgactg ggaccagcca tctcataaag    1080
tgtgcggaga aggagaaaac tttctgtgtg aatgggggcg agtgcttcac ggtgaaggac    1140
ctgtcaaacc cgtcaagata cttgtgcaag tgccaacctg gattcactgg agcaagatgt    1200
actgagaatg tacccatgaa agtccaaacc caagaaaaag cggaggaact ctaccagaag    1260
agggtgctga caattactgg catctgtatc gccctgctgg tggtcggcat catgtgtgtg    1320
gtggcctact gcaaaaccaa gaagcagcgg cagaagcttc atgatcggct tcggcagagt    1380
cttcggtcag aacggagcaa cctggtgaac atagcgaatg ggcctcacca cccaaacccg    1440
ccgccagaga acgtgcagct ggtgaatcaa tacgtatcta aaaacgtcat ctccagtgag    1500
catattgttg agagagaagt ggagacttcc ttttccacca gtcattacac ttccacagcc    1560
catcactcca cgactgtcac ccagactcct agtcacagct ggagtaatgg gcacacggag    1620
agcgtcattt cagaaagcaa ctccgtaatc atgatgtctt cggtagagaa cagcaggcac    1680
agcagtcccg ccgggggccc acgaggacgt cttcatggcc tgggaggccc tcgtgataac    1740
agcttcctca ggcatgccag agaaacccct gactcctaca gagactctcc tcatagcgaa    1800
aggtatgtat cagccatgac caccccggct cgtatgtcac ctgtagattt ccacacgcca    1860
agctccccta aatcgccccc ttcggaaatg tctccacccg tgtccagcat gacggtgtcc    1920
atgccctctg tggcagtcag cccctttgtg aagaagagag ggcctctgct gcttgtgacg    1980
ccaccaaggc tacgggagaa gaaatatgat catcaccccc agcaactcaa ctcctttcat    2040
cacaaccctg cacatcagag taccagcctc cccctagcc cactgaggat agtggaggat    2100
gaggagtacg agacgaccca ggagtatgag tcagttcaag agcccgttaa gaaagtcacc    2160
aatagccggc gggccaaaag aaccaagccc aatggccaca ttgccaatag gttggaaatg    2220
gacagcaaca caagttctgt gagcagtaac tcagaaagtg agacagaaga cgaaagagta    2280
ggtgaagaca caccattcct gggcatacag aacccctgg cagccagcct tgaggtggcc    2340
cccgccttcc gtctggctga gagcaggact aacccagcag ccgcttctc cacacaggag    2400 gaattacagg ccaggctgtc tagtgtaatc gctaaccaag accctattgc tgtataaaac    2460
ctaaataaac acatagattc acctgtaaaa ctttatttta tataataaag tatttcacct    2520
taaaaaaaaa aaaaaaaaa                                                 2540
```

<210> SEQ ID NO 5
<211> LENGTH: 695
<212> TYPE: PRT
<213> ORGANISM: Rattus norvegicus
<220> FEATURE:
<223> OTHER INFORMATION: SMDF_2a amino acid sequence

<400> SEQUENCE: 5

```
Met Glu Ile Tyr Ser Pro Asp Met Ser Glu Val Ala Gly Gly Arg
             5                  10                  15

Ser Ser Ser Pro Ser Thr Gln Leu Ser Ala Val Pro Ser Leu Asp
            20                  25                  30

Gly Leu Pro Ala Ala Glu Glu His Ile Pro Asp Thr His Thr Glu
            35                  40                  45

Asp Glu Arg Ser Pro Gly Leu Leu Gly Leu Ala Val Pro Cys Cys
            50                  55                  60

Val Cys Leu Glu Ala Glu Arg Leu Arg Gly Cys Leu Asn Ser Glu
            65                  70                  75

Lys Ile Cys Ile Val Pro Ile Leu Ala Cys Leu Val Ser Leu Cys
            80                  85                  90
```

-continued

```
Leu Cys Ile Ala Gly Leu Lys Trp Val Phe Val Asp Lys Ile Phe
             95                 100                 105

Glu Tyr Asp Ser Pro Thr His Leu Asp Pro Gly Gly Leu Gly Gln
            110                 115                 120

Asp Pro Val Ile Ser Leu Asp Pro Thr Ala Ala Pro Ala Ile Leu
            125                 130                 135

Val Ser Ser Glu Ala Tyr Thr Ser Pro Val Ser Lys Ala Gln Ser
            140                 145                 150

Glu Ala Gly Ala His Val Thr Val Gln Gly Asp His Ala Ala Val
            155                 160                 165

Ala Ser Glu Pro Ser Ala Val Pro Thr Arg Lys Asn Arg Leu Ser
            170                 175                 180

Ala Phe Pro Pro Phe His Pro Thr Ala Pro Pro Phe Pro Ser Pro
            185                 190                 195

Ala Arg Thr Pro Glu Val Arg Thr Pro Lys Ser Gly Thr Gln Pro
            200                 205                 210

Gln Thr Thr Glu Thr Asn Leu Gln Thr Ala Pro Lys Leu Ser Thr
            215                 220                 225

Ser Thr Ser Thr Thr Gly Thr Ser His Leu Ile Lys Cys Ala Glu
            230                 235                 240

Lys Glu Lys Thr Phe Cys Val Asn Gly Gly Glu Cys Phe Thr Val
            245                 250                 255

Lys Asp Leu Ser Asn Pro Ser Arg Tyr Leu Cys Lys Cys Gln Pro
            260                 265                 270

Gly Phe Thr Gly Ala Arg Cys Thr Glu Asn Val Pro Met Lys Val
            275                 280                 285

Gln Thr Gln Glu Lys Ala Glu Glu Leu Tyr Gln Lys Arg Val Leu
            290                 295                 300

Thr Ile Thr Gly Ile Cys Ile Ala Leu Leu Val Val Gly Ile Met
            305                 310                 315

Cys Val Val Ala Tyr Cys Lys Thr Lys Lys Gln Arg Gln Lys Leu
            320                 325                 330

His Asp Arg Leu Arg Gln Ser Leu Arg Ser Glu Arg Ser Asn Leu
            335                 340                 345

Val Asn Ile Ala Asn Gly Pro His His Pro Asn Pro Pro Pro Glu
            350                 355                 360

Asn Val Gln Leu Val Asn Gln Tyr Val Ser Lys Asn Val Ile Ser
            365                 370                 375

Ser Glu His Ile Val Glu Arg Glu Val Glu Thr Ser Phe Ser Thr
            380                 385                 390

Ser His Tyr Thr Ser Thr Ala His His Ser Thr Thr Val Thr Gln
            395                 400                 405

Thr Pro Ser His Ser Trp Ser Asn Gly His Thr Glu Ser Val Ile
            410                 415                 420

Ser Glu Ser Asn Ser Val Ile Met Met Ser Ser Val Glu Asn Ser
            425                 430                 435

Arg His Ser Ser Pro Ala Gly Gly Pro Arg Gly Arg Leu His Gly
            440                 445                 450

Leu Gly Gly Pro Arg Asp Asn Ser Phe Leu Arg His Ala Arg Glu
            455                 460                 465

Thr Pro Asp Ser Tyr Arg Asp Ser Pro His Ser Glu Arg Tyr Val
            470                 475                 480
```

Ser Ala Met Thr Thr Pro Ala Arg Met Ser Pro Val Asp Phe His
            485                 490                 495

Thr Pro Ser Ser Pro Lys Ser Pro Ser Glu Met Ser Pro Pro
        500                 505                 510

Val Ser Ser Met Thr Val Ser Met Pro Ser Val Ala Val Ser Pro
            515                 520                 525

Phe Val Glu Glu Glu Arg Pro Leu Leu Leu Val Thr Pro Pro Arg
            530                 535                 540

Leu Arg Glu Lys Lys Tyr Asp His His Pro Gln Gln Leu Asn Ser
            545                 550                 555

Phe His His Asn Pro Ala His Gln Ser Thr Ser Leu Pro Pro Ser
            560                 565                 570

Pro Leu Arg Ile Val Glu Asp Glu Glu Tyr Glu Thr Thr Gln Glu
            575                 580                 585

Tyr Glu Ser Val Gln Glu Pro Val Lys Lys Val Thr Asn Ser Arg
            590                 595                 600

Arg Ala Lys Arg Thr Lys Pro Asn Gly His Ile Ala Asn Arg Leu
            605                 610                 615

Glu Met Asp Ser Asn Thr Ser Ser Val Ser Ser Asn Ser Glu Ser
            620                 625                 630

Glu Thr Glu Asp Glu Arg Val Gly Glu Asp Thr Pro Phe Leu Gly
            635                 640                 645

Ile Gln Asn Pro Leu Ala Ala Ser Leu Glu Val Ala Pro Ala Phe
            650                 655                 660

Arg Leu Ala Glu Ser Arg Thr Asn Pro Ala Gly Arg Phe Ser Thr
            665                 670                 675

Gln Glu Glu Leu Gln Ala Arg Leu Ser Ser Val Ile Ala Asn Gln
            680                 685                 690

Asp Pro Ile Ala Val
            695

<210> SEQ ID NO 6
<211> LENGTH: 897
<212> TYPE: DNA
<213> ORGANISM: Rattus norvegicus
<220> FEATURE:
<223> OTHER INFORMATION: Partial cDNA sequence of SMDF_2b

<400> SEQUENCE: 6
actctactgc accgcccttc ccttctccag ctcggacccc tgaggtgaga acacccaagt      60
caggaactca gccacaaaca acagaaacta acctgcaaac tgctcctaaa ctttccacat    120
caacatccac gactgggacc agccatctca taaagtgtgc ggagaaggag aaaactttct    180
gtgtgaatgg gggcgagtgc ttcacggtga aggacctgtc aaacccgtca agatacttgt    240
gcaagtgcca acctggattc actggagcaa gatgtactga gaatgtaccc atgaaagtcc    300
aaacccaaga aaaagcggag gaactctacc agaagagggt gctgacaatt actggcatct    360
gtatcgccct gctggtggtc ggcatcatgt gtgtggtggc ctactgcaaa accaagaagc    420
agcggcagaa gcttcatgat cggcttcggc agagtcttcg gtcagaacgg agcaacctgg    480
tgaacatagc gaatgggcct caccacccaa acccgccgcc agagaacgtg cagctggtga    540
atcaatacgt atctaaaaac gtcatctcca gtgagcatat tgttgagaga aagtggagag    600
cttccttttc accagtcatt acacttcca cagcccatca ctccacgact gtcacccaga    660
ctcctagtca cagctggagt aatgggcaca cggagagcgt catttcagaa agcaactccg    720

```
taatcatgat gtcttcggta gagaacagca ggcacagcag tcccgccggg ggcccacgag    780
gacgtcttca tggcctggga ggccctcgtg ataacagctt cctcaggcat gccagagaaa    840
cccctgactc ctacagagac tctcctcata gcgaaagaca taaccttata gctgagc      897
```

<210> SEQ ID NO 7
<211> LENGTH: 298
<212> TYPE: PRT
<213> ORGANISM: Rattus norvegicus
<220> FEATURE:
<223> OTHER INFORMATION: Partial amino acid sequence of SMDF_2b

<400> SEQUENCE: 7

```
Ser Thr Ala Pro Pro Phe Pro Ser Pro Ala Arg Thr Pro Glu Val
                5                  10                  15

Arg Thr Pro Lys Ser Gly Thr Gln Pro Gln Thr Thr Glu Thr Asn
             20                  25                  30

Leu Gln Thr Ala Pro Lys Leu Ser Thr Ser Thr Ser Thr Thr Gly
         35                  40                  45

Thr Ser His Leu Ile Lys Cys Ala Glu Lys Glu Lys Thr Phe Cys
     50                  55                  60

Val Asn Gly Gly Glu Cys Phe Thr Val Lys Asp Leu Ser Asn Pro
 65                  70                  75

Ser Arg Tyr Leu Cys Lys Cys Gln Pro Gly Phe Thr Gly Ala Arg
             80                  85                  90

Cys Thr Glu Asn Val Pro Met Lys Val Gln Thr Gln Glu Lys Ala
         95                 100                 105

Glu Glu Leu Tyr Gln Lys Arg Val Leu Thr Ile Thr Gly Ile Cys
    110                 115                 120

Ile Ala Leu Leu Val Val Gly Ile Met Cys Val Val Ala Tyr Cys
    125                 130                 135

Lys Thr Lys Lys Gln Arg Gln Lys Leu His Asp Arg Leu Arg Gln
    140                 145                 150

Ser Leu Arg Ser Glu Arg Ser Asn Leu Val Asn Ile Ala Asn Gly
    155                 160                 165

Pro His His Pro Asn Pro Pro Glu Asn Val Gln Leu Val Asn
    170                 175                 180

Gln Tyr Val Ser Lys Asn Val Ile Ser Ser Glu His Ile Val Glu
    185                 190                 195

Arg Glu Val Glu Thr Ser Phe Ser Thr Ser His Tyr Thr Ser Thr
    200                 205                 210

Ala His His Ser Thr Thr Val Thr Gln Thr Pro Ser His Ser Trp
    215                 220                 225

Ser Asn Gly His Thr Glu Ser Val Ile Ser Glu Ser Asn Ser Val
    230                 235                 240

Ile Met Met Ser Ser Val Glu Asn Ser Arg His Ser Ser Pro Ala
    245                 250                 255

Gly Gly Pro Arg Gly Arg Leu His Gly Leu Gly Gly Pro Arg Asp
    260                 265                 270

Asn Ser Phe Leu Arg His Ala Arg Glu Thr Pro Asp Ser Tyr Arg
    275                 280                 285

Asp Ser Pro His Ser Glu Arg His Asn Leu Ile Ala Glu
    290                 295
```

<210> SEQ ID NO 8
<211> LENGTH: 333

<212> TYPE: DNA
<213> ORGANISM: Rattus norvegicus
<220> FEATURE:
<223> OTHER INFORMATION: Partial cDNA sequence of SMDF_2

<400> SEQUENCE: 8

| | | |
|---|---|---|
| gcttttcctc cctttcactc tactgcaccg cccttccctt ctccagctcg gacccctgag | 60 |
| gtgagaacac ccaagtcagg aactcagcca caaacaacag aaactaacct gcaaactgct | 120 |
| cctaaacttt ccacaacaac atccacgact gggaccagcc atctcataaa gtgtgcggag | 180 |
| aaggagaaaa ctttctgtgt gaatggggc gagtgcttca cggtgaagga cctgtcaaac | 240 |
| ccgtcaagat acttgtgcaa gtgcccaaat gagtttactg gtgatcgttg ccaaaactac | 300 |
| gtaatggcca gcttctacaa agcggaggaa ctc | 333 |

<210> SEQ ID NO 9
<211> LENGTH: 111
<212> TYPE: PRT
<213> ORGANISM: Rattus norvegicus
<220> FEATURE:
<223> OTHER INFORMATION: Partial amino acid sequence of SMDF_2

<400> SEQUENCE: 9

Ala Phe Pro Pro Phe His Ser Thr Ala Pro Pro Phe Pro Ser Pro
                5                  10                  15

Ala Arg Thr Pro Glu Val Arg Thr Pro Lys Ser Gly Thr Gln Pro
              20                  25                  30

Gln Thr Thr Glu Thr Asn Leu Gln Thr Ala Pro Lys Leu Ser Thr
              35                  40                  45

Thr Thr Ser Thr Thr Gly Thr Ser His Leu Ile Lys Cys Ala Glu
              50                  55                  60

Lys Glu Lys Thr Phe Cys Val Asn Gly Gly Glu Cys Phe Thr Val
              65                  70                  75

Lys Asp Leu Ser Asn Pro Ser Arg Tyr Leu Cys Lys Cys Pro Asn
              80                  85                  90

Glu Phe Thr Gly Asp Arg Cys Gln Asn Tyr Val Met Ala Ser Phe
              95                 100                 105

Tyr Lys Ala Glu Glu Leu
             110

<210> SEQ ID NO 10
<211> LENGTH: 808
<212> TYPE: DNA
<213> ORGANISM: Rattus norvegicus
<220> FEATURE:
<223> OTHER INFORMATION: Partial cDNA sequence of SMDF_3

<400> SEQUENCE: 10

| | | |
|---|---|---|
| cacccacaca gaagatgaga gaagccctgg actcctgggc ctggcggtgc cctgctgtgt | 60 |
| gtgcctggaa gctgagcgcc tgagagggtg tctcaactcc gagaagatct gcattgttcc | 120 |
| cattctggct tgcctagtca gcctctgcct ctgcattgct ggcctgaagt gggtatttgt | 180 |
| ggacaagata tttgaatacg actctcctac ccaccttgac cctgggggt taggccagga | 240 |
| ccctgtgatt tctctggatc caactgctgc cccagccatt ttggtatcat ccaggcata | 300 |
| cacttcacct gtctctaagg ctcagtctga agctggggct catgttacag tacaaggtga | 360 |
| ccatgctgct gtggcctctg aaccttcagc agtaccgacc cggaagaacc ggctgtctgc | 420 |
| ttttcctccc tttcactcta ctgcaccgcc cttcccttct ccagctcgga cccctgaagt | 480 |

```
gagaacaccc aagtcaggaa ctcagccaca acaacagaa actaacctgc aaactgctcc    540
taaactttcc acatcaacat ccacgactgg gaccagccat ctcataaagt gtgcggagaa    600
ggagaaaact ttctgtgtga atggggggga gtgcttcacg gtgaaggacc tgtcaaaccc    660
gtcaagatac ttgtgcaagt gcccaaatga gtttactggt gatcgttgcc aaaactacgt    720
aatggccagc ttctacagta cgtccactcc ctttctgtct ctgcctgagt aggagcatgc    780
tcagtcgatg ctgctttctt gttgctac                                      808
```

<210> SEQ ID NO 11
<211> LENGTH: 256
<212> TYPE: PRT
<213> ORGANISM: Rattus norvegicus
<220> FEATURE:
<223> OTHER INFORMATION: Partial amino acid sequence of SMDF_3

<400> SEQUENCE: 11

```
Thr His Thr Glu Asp Glu Arg Ser Pro Gly Leu Leu Gly Leu Ala
                5                  10                  15

Val Pro Cys Cys Val Cys Leu Glu Ala Glu Arg Leu Arg Gly Cys
             20                  25                  30

Leu Asn Ser Glu Lys Ile Cys Ile Val Pro Ile Leu Ala Cys Leu
             35                  40                  45

Val Ser Leu Cys Leu Cys Ile Ala Gly Leu Lys Trp Val Phe Val
             50                  55                  60

Asp Lys Ile Phe Glu Tyr Asp Ser Pro Thr His Leu Asp Pro Gly
             65                  70                  75

Gly Leu Gly Gln Asp Pro Val Ile Ser Leu Asp Pro Thr Ala Ala
             80                  85                  90

Pro Ala Ile Leu Val Ser Ser Glu Ala Tyr Thr Ser Pro Val Ser
             95                 100                 105

Lys Ala Gln Ser Glu Ala Gly Ala His Val Thr Val Gln Gly Asp
            110                 115                 120

His Ala Ala Val Ala Ser Glu Pro Ser Ala Val Pro Thr Arg Lys
            125                 130                 135

Asn Arg Leu Ser Ala Phe Pro Pro Phe His Ser Thr Ala Pro Pro
            140                 145                 150

Phe Pro Ser Pro Ala Arg Thr Pro Glu Val Arg Thr Pro Lys Ser
            155                 160                 165

Gly Thr Gln Pro Gln Thr Thr Glu Thr Asn Leu Gln Thr Ala Pro
            170                 175                 180

Lys Leu Ser Thr Ser Thr Ser Thr Gly Thr Ser His Leu Ile
            185                 190                 195

Lys Cys Ala Glu Lys Glu Lys Thr Phe Cys Val Asn Gly Gly Glu
            200                 205                 210

Cys Phe Thr Val Lys Asp Leu Ser Asn Pro Ser Arg Tyr Leu Cys
            215                 220                 225

Lys Cys Pro Asn Glu Phe Thr Gly Asp Arg Cys Gln Asn Tyr Val
            230                 235                 240

Met Ala Ser Phe Tyr Ser Thr Ser Thr Pro Phe Leu Ser Leu Pro
            245                 250                 255

Glu
```

<210> SEQ ID NO 12
<211> LENGTH: 408
<212> TYPE: DNA

```
<213> ORGANISM: Rattus norvegicus
<220> FEATURE:
<223> OTHER INFORMATION: Partial cDNA sequence of SMDF_4

<400> SEQUENCE: 12
gcttttcctc cctttcactc tactgcaccg cccttccctt ctccagctcg gacccctgag      60
gtgagaacac ccaagtcagg aactcagcca caaacaacag aaactaacct gcaaactgct     120
cctaaacttt ccacatcaac atccacgact gggaccagcc atctcataaa gtgtgcggag     180
aaggagaaaa ctttctgtgt gaatggggc gagtgcttca cggtgaagga cctgtcaaac     240
ccgtcaagat acttgtgcaa gtgcccaaat gagtttactg gtgatcgttg ccaaaactac     300
gtaatggcca gcttctacat gacttctagg aggaaaaggc aagaaacaga gaagcctcta     360
gaaagaaaat tggatcatag ccttgtgaaa gaatcgaaag cggaggaa                 408

<210> SEQ ID NO 13
<211> LENGTH: 136
<212> TYPE: PRT
<213> ORGANISM: Rattus norvegicus
<220> FEATURE:
<223> OTHER INFORMATION: Partial amino acid sequence of SMDF_4

<400> SEQUENCE: 13

Ala Phe Pro Pro Phe His Ser Thr Ala Pro Pro Phe Pro Ser Pro
                 5                  10                  15

Ala Arg Thr Pro Glu Val Arg Thr Pro Lys Ser Gly Thr Gln Pro
             20                  25                  30

Gln Thr Thr Glu Thr Asn Leu Gln Thr Ala Pro Lys Leu Ser Thr
             35                  40                  45

Ser Thr Ser Thr Thr Gly Thr Ser His Leu Ile Lys Cys Ala Glu
         50                  55                  60

Lys Glu Lys Thr Phe Cys Val Asn Gly Gly Glu Cys Phe Thr Val
         65                  70                  75

Lys Asp Leu Ser Asn Pro Ser Arg Tyr Leu Cys Lys Cys Pro Asn
         80                  85                  90

Glu Phe Thr Gly Asp Arg Cys Gln Asn Tyr Val Met Ala Ser Phe
         95                 100                 105

Tyr Met Thr Ser Arg Arg Lys Arg Gln Glu Thr Glu Lys Pro Leu
            110                 115                 120

Glu Arg Lys Leu Asp His Ser Leu Val Lys Glu Ser Lys Ala Glu
            125                 130                 135

Glu

<210> SEQ ID NO 14
<211> LENGTH: 21
<212> TYPE: DNA
<213> ORGANISM: Artificial sequence
<220> FEATURE:
<223> OTHER INFORMATION: Synthetic oligonucleotide corresponding to
      common SMDF amino terminus forward used for PCR of SMDF isoforms

<400> SEQUENCE: 14
tatgttcctc cgctgccgga a                                                21

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide used for PCR of SMDF
```

-continued isoforms

<400> SEQUENCE: 15
gcttttcctc cctttcac                                                18

<210> SEQ ID NO 16
<211> LENGTH: 21
<212> TYPE: DNA
<213> ORGANISM: Artificial sequence
<220> FEATURE:
<223> OTHER INFORMATION: Synthetic oligonucleotide used for PCR of SMDF
     isoforms

<400> SEQUENCE: 16
cacccacaca gaagatgaga g                                        21

<210> SEQ ID NO 17
<211> LENGTH: 23
<212> TYPE: DNA
<213> ORGANISM: Artificial sequence
<220> FEATURE:
<223> OTHER INFORMATION: Synthetic oligonucleotide for 5' untranslated
     region of SMDF(1a cDNA (pSLC135)

<400> SEQUENCE: 17
cagacgcctg aggtgagaaa cat                                   23

<210> SEQ ID NO 18
<211> LENGTH: 24
<212> TYPE: DNA
<213> ORGANISM: Artificial sequence
<220> FEATURE:
<223> OTHER INFORMATION: Synthetic oligonucleotide for 5' untranslated
     region of SMDF(1a cDNA (pSLC135)

<400> SEQUENCE: 18
aagtccaagg caattaccca aagt                                24

<210> SEQ ID NO 19
<211> LENGTH: 6
<212> TYPE: DNA
<213> ORGANISM: Unknown
<220> FEATURE:
<221> NAME/KEY: polyA_signal
<222> LOCATION: 1..6
<223> OTHER INFORMATION: eukaryotic polyadenylation signal

<400> SEQUENCE: 19 aataaa                                                                  6

<210> SEQ ID NO 20
<211> LENGTH: 3086
<212> TYPE: DNA
<213> ORGANISM: Rattus norvegicus
<220> FEATURE:
<223> OTHER INFORMATION: GGF_1a cDNA sequence

<400> SEQUENCE: 20
gaattcggca cgagcccagc gtgggctcgg tgcaggagct ggcccggcgc gccgcggtgg    60
tgatcgaggg aaaggtgcac ccgccgcggc ggcagcaggg ggcactcgac aggaaggcag  120
caggcgaggc aggggcaggg gcgcgggacc agcccgtcca ggactcgcca ccttcacagg  180
accctctgcc tgctgtcaac tggaccctgc ccactggggg cccgagccc agcaccgatc  240 agcccgggga ccccgcgccc tatctggtca aggtgcacca ggtgtgggct gtgaaagccg  300

-continued

```
ggggtttgaa gaaggactcg ctactcaccg tgcgcctgga tacctggggc cacccagcct    360
tcccgtcctg cgggcggctc aaggaggaca gcaggtacat cttcttcatg gagccggatg    420
ccaacagcag cggccgcgcg ccgcccgcct tccgagcctc gtttccccca ctggagactg    480
gccgcaacct caagaaggag gtcagccggg tgttgtgcaa gcggtgcgca ctgcctccca    540
gattgaaaga aatgaagagc caggagtcag ctgcaggctc caagctagtg ctccggtgcg    600
aaaccagctc cgagtactcc tcactcagat tcaaatggtt caagaatggg aacgagctga    660
accgcaaaaa taaccagaa aacatcaaga tacagaagaa gccagggaag tcagagcttc    720
gaattaacaa agcatccctg gctgactctg gagagtatat gtgcaaagtg atcagcaagt    780
taggaaatga cagtgcctct gccaacatca ccattgttga gtcaaacgag ttcatcactg    840
gcatgccagc ctcgactgag acagcctatg tgtcctcaga gtctcccatt agaatctcag    900
tttcaacaga aggcgcaaac acttcttcat ccacatcgac atccacgact gggaccagcc    960
atctcataaa gtgcgcggag aaggagaaaa ctttctgtgt gaatgggggc gagtgcttca   1020
cggtgaagga cctgtcaaac ccgtcaagat acttgtgcaa gtgcccaaat gagtttactg   1080
gtgatcgttg ccaaaactac gtaatggcca gcttctacaa gcatcttggg attgaattta   1140
tggaagcgga ggaactctac cagaagaggg tgctgacaat tactggcatc tgtatcgccc   1200
tgctggtggt cggcatcatg tgtgtggtgg cctactgcaa aaccaagaag cagcggcaga   1260
agcttcatga tcggcttcgg cagagtcttc ggtcagaacg gagcaacctg gtgaacatag   1320
cgaatgggcc tcaccaccca aacccgccgc cagagaacgt gcagctggtg aatcaatacg   1380
tatctaaaaa cgtcatctcc agtgagcata ttgttgagag agaagtggag acttccttt    1440
ccaccagtca ttacacttcc acagcccatc actccacgac tgtcacccag actcctagtc   1500
acagctggag taatgggcac acggagagcg tcatttcaga aagcaactcc gtaatcatga   1560
tgtcttcggt agagaacagc aggcacagca gtccgccgg gggcccacga ggacgtcttc   1620
atggcctggg aggccctcgt gataacagct tcctcaggca tgccagagaa acccctgact   1680
cctacagaga ctctccctca tagcgaaaggt atgtatcagc catgaccacc ccggctcgta   1740
tgtcacctgt agatttccac acgccaagct cccctaaatc gccccctttcg gaaatgtctc   1800
cacccgtgtc cagcatgacg gtgtccatgc cctctgtggc agtcagcccc tttgtggaag   1860
aagagaggcc tctgctgctt gtgacgccac caaggctacg ggagaagaaa tatgatcatc   1920
accccagca actcaactcc tttcatcaca acctgcaca tcagagtacc agcctccccc   1980
ctagcccact gaggatagtg gaggatgagg agtacgagac gacccaggag tatgagtcag   2040
ttcaagagcc cgttaagaaa gtcaccaata gccggcgggc caaaagaacc aagcccaatg   2100
gccacattgc caataggttg gaaatggaca gcaacacaag ttctgtgagc agtaactcag   2160
aaagtgagac agaagacgaa agagtaggtg aagcacacc attcctgggc atacagaacc   2220
ccctggcagc cagccttgag gtggcccccg ccttccgtct ggctgagagc aggactaacc   2280
cagcaggccg cttctccaca caggaggaat acaggccag ctgtctagt gtaatcgcta   2340
accaagaccc tattgctgta taaaacctaa ataaacacat agattcacct gtaaaacttt   2400
attttatata ataagtatt tcaccttaaa ttaaacaatt tatttatttt tagcagttct   2460
gcaaatagaa aacaggaaga aaaaactttt tataaattaa atatatgtat gtaaaaatgt   2520
gttatgtgcc atatgtagca attttttaca gtatttcaaa aacgagaaag atatcaatgg   2580
tgcctttatg ttctgttatg tcgagagcaa gttttataaa gttatggtga tttcttttc   2640
acagtatttc agcaaaacct cccatatatt cagtttctgc tggcttttg tggattgcat   2700
```

```
tatgatgttg actggatgta tggtttgcaa ggctagcagc tagctcgcac tcgctctctc    2760
tctctctctc tctctgtctg tctctctgtc tctctctctc tctctctctc tctctgtctc    2820
tctctctctc tctctctctc tctctctctc agcttcccgt agctcccaac ccgtactgtc    2880
ttggactggc acatccatcc aaatacctttc ctactttgta tgaagttttc tttgctttcc   2940
caatatgaaa tgagttctct ctactctgtc agccaaaggt ttgcttcact ggactctgag    3000
ataatagtag acccagcagc atgctactat tatgtatagc aggaaactgc accaagtaat    3060
gtccaataat aggaagaaac gatatc                                          3086
```

<210> SEQ ID NO 21
<211> LENGTH: 782
<212> TYPE: PRT
<213> ORGANISM: Rattus norvegicus
<220> FEATURE:
<223> OTHER INFORMATION: GGF_1a amino acid sequence

<400> SEQUENCE: 21

```
Pro Ser Val Gly Ser Val Gln Glu Leu Ala Arg Arg Ala Ala Val
                 5                  10                  15

Val Ile Glu Gly Lys Val His Pro Pro Arg Arg Gln Gln Gly Ala
                20                  25                  30

Leu Asp Arg Lys Ala Ala Gly Glu Ala Gly Ala Gly Ala Arg Asp
                35                  40                  45

Gln Pro Val Gln Asp Ser Pro Ser Gln Asp Pro Leu Pro Ala
                50                  55                  60

Val Asn Trp Thr Leu Pro Thr Gly Gly Pro Glu Pro Ser Thr Asp
                65                  70                  75

Gln Pro Gly Asp Pro Ala Pro Tyr Leu Val Lys Val His Gln Val
                80                  85                  90

Trp Ala Val Lys Ala Gly Gly Leu Lys Lys Asp Ser Leu Leu Thr
                95                 100                 105

Val Arg Leu Asp Thr Trp Gly His Pro Ala Phe Pro Ser Cys Gly
               110                 115                 120

Arg Leu Lys Glu Asp Ser Arg Tyr Ile Phe Phe Met Glu Pro Asp
               125                 130                 135

Ala Asn Ser Ser Gly Arg Ala Pro Pro Ala Phe Arg Ala Ser Phe
               140                 145                 150

Pro Pro Leu Glu Thr Gly Arg Asn Leu Lys Lys Glu Val Ser Arg
               155                 160                 165

Val Leu Cys Lys Arg Cys Ala Leu Pro Pro Arg Leu Lys Glu Met
               170                 175                 180

Lys Ser Gln Glu Ser Ala Ala Gly Ser Lys Leu Val Leu Arg Cys
               185                 190                 195

Glu Thr Ser Ser Glu Tyr Ser Ser Leu Arg Phe Lys Trp Phe Lys
               200                 205                 210

Asn Gly Asn Glu Leu Asn Arg Lys Asn Lys Pro Glu Asn Ile Lys
               215                 220                 225

Ile Gln Lys Lys Pro Gly Lys Ser Glu Leu Arg Ile Asn Lys Ala
               230                 235                 240

Ser Leu Ala Asp Ser Gly Glu Tyr Met Cys Lys Val Ile Ser Lys
               245                 250                 255

Leu Gly Asn Asp Ser Ala Ser Ala Asn Ile Thr Ile Val Glu Ser
               260                 265                 270
```

-continued

```
Asn Glu Phe Ile Thr Gly Met Pro Ala Ser Thr Glu Thr Ala Tyr
            275                 280                 285

Val Ser Ser Glu Ser Pro Ile Arg Ile Ser Val Ser Thr Glu Gly
            290                 295                 300

Ala Asn Thr Ser Ser Ser Thr Ser Thr Ser Thr Thr Gly Thr Ser
            305                 310                 315

His Leu Ile Lys Cys Ala Glu Lys Glu Lys Thr Phe Cys Val Asn
            320                 325                 330

Gly Gly Glu Cys Phe Thr Val Lys Asp Leu Ser Asn Pro Ser Arg
            335                 340                 345

Tyr Leu Cys Lys Cys Pro Asn Glu Phe Thr Gly Asp Arg Cys Gln
            350                 355                 360

Asn Tyr Val Met Ala Ser Phe Tyr Lys His Leu Gly Ile Glu Phe
            365                 370                 375

Met Glu Ala Glu Leu Tyr Gln Lys Arg Val Leu Thr Ile Thr
            380                 385                 390

Gly Ile Cys Ile Ala Leu Leu Val Val Gly Ile Met Cys Val Val
            395                 400                 405

Ala Tyr Cys Lys Thr Lys Lys Gln Arg Gln Lys Leu His Asp Arg
            410                 415                 420

Leu Arg Gln Ser Leu Arg Ser Glu Arg Ser Asn Leu Val Asn Ile
            425                 430                 435

Ala Asn Gly Pro His His Pro Asn Pro Pro Glu Asn Val Gln
            440                 445                 450

Leu Val Asn Gln Tyr Val Ser Lys Asn Val Ile Ser Ser Glu His
            455                 460                 465

Ile Val Glu Arg Glu Val Glu Thr Ser Phe Ser Thr Ser His Tyr
            470                 475                 480

Thr Ser Thr Ala His His Ser Thr Thr Val Thr Gln Thr Pro Ser
            485                 490                 495

His Ser Trp Ser Asn Gly His Thr Glu Ser Val Ile Ser Glu Ser
            500                 505                 510

Asn Ser Val Ile Met Met Ser Ser Val Glu Asn Ser Arg His Ser
            515                 520                 525

Ser Pro Ala Gly Gly Pro Arg Gly Arg Leu His Gly Leu Gly Gly
            530                 535                 540

Pro Arg Asp Asn Ser Phe Leu Arg His Ala Arg Glu Thr Pro Asp
            545                 550                 555

Ser Tyr Arg Asp Ser Pro His Ser Glu Arg Tyr Val Ser Ala Met
            560                 565                 570

Thr Thr Pro Ala Arg Met Ser Pro Val Asp Phe His Thr Pro Ser
            575                 580                 585

Ser Pro Lys Ser Pro Pro Ser Glu Met Ser Pro Pro Val Ser Ser
            590                 595                 600

Met Thr Val Ser Met Pro Ser Val Ala Val Ser Pro Phe Val Glu
            605                 610                 615

Glu Glu Arg Pro Leu Leu Leu Val Thr Pro Pro Arg Leu Arg Glu
            620                 625                 630

Lys Lys Tyr Asp His His Pro Gln Gln Leu Asn Ser Phe His His
            635                 640                 645

Asn Pro Ala His Gln Ser Thr Ser Leu Pro Pro Ser Pro Leu Arg
            650                 655                 660

Ile Val Glu Asp Glu Glu Tyr Glu Thr Thr Gln Glu Tyr Glu Ser
```

-continued

```
                    665                 670                 675

Val Gln Glu Pro Val Lys Lys Val Thr Asn Ser Arg Arg Ala Lys
                680                 685                 690

Arg Thr Lys Pro Asn Gly His Ile Ala Asn Arg Leu Glu Met Asp
                695                 700                 705

Ser Asn Thr Ser Ser Val Ser Ser Asn Ser Glu Ser Glu Thr Glu
                710                 715                 720

Asp Glu Arg Val Gly Glu Asp Thr Pro Phe Leu Gly Ile Gln Asn
                725                 730                 735

Pro Leu Ala Ala Ser Leu Glu Val Ala Pro Ala Phe Arg Leu Ala
                740                 745                 750

Glu Ser Arg Thr Asn Pro Ala Gly Arg Phe Ser Thr Gln Glu Glu
                755                 760                 765

Leu Gln Ala Arg Leu Ser Ser Val Ile Ala Asn Gln Asp Pro Ile
                770                 775                 780

Ala Val

<210> SEQ ID NO 22
<211> LENGTH: 952
<212> TYPE: DNA
<213> ORGANISM: Rattus norvegicus
<220> FEATURE:
<223> OTHER INFORMATION: GGF_2 cDNA sequence

<400> SEQUENCE: 22
ccctctgcct gctgtcaact ggaccctgcc cactgggggc cccgagccca gcaccgatca     60
gcccggggac cccgcgccct atctggtcaa ggtgcaccag gtgtgggctg tgaaagccgg    120
gggtttgaag aaggactcgc tactcaccgt gcgcctggat acctggggcc acccagcctt    180
cccgtcctgc gggcggctca aggaggacag caggtacatc ttcttcatgg agccggatgc    240
caacagcagc ggccgcgcgc cgcccgcctt ccgagcctcg tttcccccac tggagactgg    300
ccgcgacctc aagaaggagg tcagccgggt gttgtgcaag cggtgcgcac tgcctcccag    360
attgaaagaa atgaagagcc aggagtcagc tgcaggctcc aagctagtgc tccggtgcga    420
aaccagctcc gagtactcct cactcagatt caaatggttc aagaatggga acgagctgaa    480
ccgcaaaaat aaaccagaaa acatcaagat acagaagaag ccaggaagt cagagcttcg    540 aattaacaaa gcatccctgg ctgactctgg agagtatatg tgcaaagtga tcagcaagtt    600
aggaaatgac agtgcctctg ccaacatcac cattgttgag tcaaacgagt tcatcactgg    660
catgccagcc tcgactgaga cagcctatgt gtcctcagag tctcccatta gaatctcagt    720
ttcaacagaa ggcgcaaaca cttcttcatc cacatcgaca tccacgactg ggaccagcca    780
tctcataaag tgcgcggaga aggagaaaac tttctgtgtg aatggggcg agtgcttcac    840 ggtgaaggac ctgtcaaacc cgtcaagata cttgtgcaag tgcccaaatg agtttactgg    900
tgatcgttgc caaaactacg taatggccag cttctacaaa gcggaggaac tc           952

<210> SEQ ID NO 23
<211> LENGTH: 317
<212> TYPE: PRT
<213> ORGANISM: Rattus norvegicus
<220> FEATURE:
<223> OTHER INFORMATION: GGF_2 amino acid sequence

<400> SEQUENCE: 23

Pro Leu Pro Ala Val Asn Trp Thr Leu Pro Thr Gly Gly Pro Glu
                  5                  10                  15
```

```
Pro Ser Thr Asp Gln Pro Gly Asp Pro Ala Pro Tyr Leu Val Lys
             20                  25                  30

Val His Gln Val Trp Ala Val Lys Ala Gly Gly Leu Lys Lys Asp
         35                  40                  45

Ser Leu Leu Thr Val Arg Leu Asp Thr Trp Gly His Pro Ala Phe
             50                  55                  60

Pro Ser Cys Gly Arg Leu Lys Glu Asp Ser Arg Tyr Ile Phe Phe
             65                  70                  75

Met Glu Pro Asp Ala Asn Ser Ser Gly Arg Ala Pro Pro Ala Phe
             80                  85                  90

Arg Ala Ser Phe Pro Pro Leu Glu Thr Gly Arg Asp Leu Lys Lys
             95                 100                 105

Glu Val Ser Arg Val Leu Cys Lys Arg Cys Ala Leu Pro Pro Arg
            110                 115                 120

Leu Lys Glu Met Lys Ser Gln Glu Ser Ala Ala Gly Ser Lys Leu
            125                 130                 135

Val Leu Arg Cys Glu Thr Ser Ser Glu Tyr Ser Ser Leu Arg Phe
            140                 145                 150

Lys Trp Phe Lys Asn Gly Asn Glu Leu Asn Arg Lys Asn Lys Pro
            155                 160                 165

Glu Asn Ile Lys Ile Gln Lys Lys Pro Gly Lys Ser Glu Leu Arg
            170                 175                 180

Ile Asn Lys Ala Ser Leu Ala Asp Ser Gly Glu Tyr Met Cys Lys
            185                 190                 195

Val Ile Ser Lys Leu Gly Asn Asp Ser Ala Ser Ala Asn Ile Thr
            200                 205                 210

Ile Val Glu Ser Asn Glu Phe Ile Thr Gly Met Pro Ala Ser Thr
            215                 220                 225

Glu Thr Ala Tyr Val Ser Ser Glu Ser Pro Ile Arg Ile Ser Val
            230                 235                 240

Ser Thr Glu Gly Ala Asn Thr Ser Ser Ser Thr Ser Thr Ser Thr
            245                 250                 255

Thr Gly Thr Ser His Leu Ile Lys Cys Ala Glu Lys Glu Lys Thr
            260                 265                 270

Phe Cys Val Asn Gly Gly Glu Cys Phe Thr Val Lys Asp Leu Ser
            275                 280                 285

Asn Pro Ser Arg Tyr Leu Cys Lys Cys Pro Asn Glu Phe Thr Gly
            290                 295                 300

Asp Arg Cys Gln Asn Tyr Val Met Ala Ser Phe Tyr Lys Ala Glu
            305                 310                 315

Glu Leu

<210> SEQ ID NO 24
<211> LENGTH: 1004
<212> TYPE: DNA
<213> ORGANISM: Rattus norvegicus
<220> FEATURE:
<223> OTHER INFORMATION: GGF_3 cDNA sequence

<400> SEQUENCE: 24
ccctctgcct gctgtcaact ggaccctgcc cactgggggc cccgagccca gcaccgatca      60
gcccggggac cccgcgccct atctggtcaa ggtgcaccag gtgtgggctg tgaaagccgg     120
gggtttgaag aaggactcgc tactcaccgt gcgcctggat acctggggcc acccagcctt     180
```

-continued

```
cccgtcctgc gggcggctca aggaggacag caggtacatc ttcttcatgg agccggatgc    240
caacagcagc ggccgcgcgc cgcccgcctt ccgagcctcg tttcccccac tggagactgg    300
ccgcaacctc aagaaggagg tcagccgggt gttgtgcaag cggtgcgcac tgcctcccag    360
attgaaagaa atgaagagcc aggagtcagc tgcaggctcc aagctagtgc tccggtgcga    420
aaccagctcc gagtactcct cactcagatt caaatggttc aagaatggga acagctgaa    480 ccgcaaaaat aaaccagaaa acatcaagat acagaagaag ccagggaagt cagagcttcg    540
aattaacaaa gcatccccgg ctgactctgg agagtatatg tgcaaagtga tcagcaagtt    600
aggaaatgac agtgcctctg ccaacatcac cattgttgag tcaaacgagt tcatcactgg    660
catgccagcc tcgactgaga cagcctatgt gtcctcagag tctcccatta gaatctcagt    720
ttcaacagaa ggcgcaaaca cttcttcatc cacatcaaca tccacgactg ggaccagcca    780
tctcataaag tgtgcggaga aggagaaaac tttctgtgtg aatggggcg agtgcttcac    840 ggtgaaggac ctgtcaaacc cgtcaagata cttgtgcaag tgcccaaatg agtttactgg    900
tgatcgttgc caaaactacg taatggccag cttctacagt acgtccaccc cctttctgtc    960
tctgcctgag taggagcacg ctcagtcgat gctgctttct tgtt                    1004
```

<210> SEQ ID NO 25
<211> LENGTH: 323
<212> TYPE: PRT
<213> ORGANISM: Rattus norvegicus
<220> FEATURE:
<223> OTHER INFORMATION: GGF_3 amino acid sequence

<400> SEQUENCE: 25

```
Pro Leu Pro Ala Val Asn Trp Thr Leu Pro Thr Gly Gly Pro Glu
                5                  10                  15

Pro Ser Thr Asp Gln Pro Gly Asp Pro Ala Pro Tyr Leu Val Lys
               20                  25                  30

Val His Gln Val Trp Ala Val Lys Ala Gly Gly Leu Lys Lys Asp
               35                  40                  45

Ser Leu Leu Thr Val Arg Leu Asp Thr Trp Gly His Pro Ala Phe
               50                  55                  60

Pro Ser Cys Gly Arg Leu Lys Glu Asp Ser Arg Tyr Ile Phe Phe
               65                  70                  75

Met Glu Pro Asp Ala Asn Ser Ser Gly Arg Ala Pro Pro Ala Phe
               80                  85                  90

Arg Ala Ser Phe Pro Pro Leu Glu Thr Gly Arg Asn Leu Lys Lys
               95                 100                 105

Glu Val Ser Arg Val Leu Cys Lys Arg Cys Ala Leu Pro Pro Arg
              110                 115                 120

Leu Lys Glu Met Lys Ser Gln Glu Ser Ala Ala Gly Ser Lys Leu
              125                 130                 135

Val Leu Arg Cys Glu Thr Ser Ser Glu Tyr Ser Ser Leu Arg Phe
              140                 145                 150

Lys Trp Phe Lys Asn Gly Asn Glu Leu Asn Arg Lys Asn Lys Pro
              155                 160                 165

Glu Asn Ile Lys Ile Gln Lys Lys Pro Gly Lys Ser Glu Leu Arg
              170                 175                 180

Ile Asn Lys Ala Ser Pro Ala Asp Ser Gly Glu Tyr Met Cys Lys
              185                 190                 195

Val Ile Ser Lys Leu Gly Asn Asp Ser Ala Ser Ala Asn Ile Thr
              200                 205                 210
```

Ile Val Glu Ser Asn Glu Phe Ile Thr Gly Met Pro Ala Ser Thr
            215                 220                 225

Glu Thr Ala Tyr Val Ser Ser Glu Ser Pro Ile Arg Ile Ser Val
            230                 235                 240

Ser Thr Glu Gly Ala Asn Thr Ser Ser Thr Ser Thr Ser Thr
            245                 250                 255

Thr Gly Thr Ser His Leu Ile Lys Cys Ala Glu Lys Glu Lys Thr
            260                 265                 270

Phe Cys Val Asn Gly Gly Glu Cys Phe Thr Val Lys Asp Leu Ser
            275                 280                 285

Asn Pro Ser Arg Tyr Leu Cys Lys Cys Pro Asn Glu Phe Thr Gly
            290                 295                 300

Asp Arg Cys Gln Asn Tyr Val Met Ala Ser Phe Tyr Ser Thr Ser
            305                 310                 315

Thr Pro Phe Leu Ser Leu Pro Glu
            320

<210> SEQ ID NO 26
<211> LENGTH: 1027
<212> TYPE: DNA
<213> ORGANISM: Rattus norvegicus
<220> FEATURE:
<223> OTHER INFORMATION: GGF_4 cDNA sequence

<400> SEQUENCE: 26
ccctctgcct gctgtcaact ggaccctgcc cactgggggc cccgagccca gcaccgatca    60
gcccggggac cccgcgccct atctggtcaa ggtgcaccag gtgtgggctg tgaaagccgg   120
gggtttgaag aaggactcgc tactcaccgt gcgcctggat acctggggcc acccagcctt   180
cccgtcctgc gggcggctca aggaggacag caggtacatc ttcttcatgg agccggatgc   240
caacagcagc ggccgcgcgc cgcccgcctt ccgagcctcg tttccccac tggagactgg   300
ccgcaacctc aagaaggagg tcagccgggt gttgtgcaag cggtgcgcac tgcctcccag   360
attgaaagaa atgaagagcc aggagtcagc tgcaggctcc aagctagtgc tccggtgcga   420
aaccagctcc gagtactcct cactcagatt caaatggttc aagaatggga acgagctgaa   480
ccgcaaaaat aaaccagaaa acatcaagat acagaagaag ccaggaagt cagagcttcg   540
aattaacaaa gcatccctgg ctgactctgg agagtatatg tgcaaagtga tcagcaagtt   600
aggaaatgac agtgcctctg ccaacatcac cattgttgag tcaaacgagt tcatcactgg   660
catgccagcc tcgactgaga cagcctatgt gtcctcagag tctcccatta gaatctcagt   720
ttcaacagaa ggcgcaaaca cttcttcatc cacatcaaca tccacgactg ggaccagcca   780
tctcataaag tgtgcggaga aggagaaaac tttctgtgtg aatggggcg agtgcttcac   840
ggtgaaggac ctgtcaaacc cgtcaagata cttgtgcaag tgcccaaatg agtttactgg   900
tgatcgttgc caaaactacg taatggccag cttctacatg acttctagga ggaaaaggca   960
agaaacagag aagcctctag aaagaaaatt ggatcatagc cttgtgaaag aatcgaaagc  1020
ggaggaa                                                           1027

<210> SEQ ID NO 27
<211> LENGTH: 342
<212> TYPE: PRT
<213> ORGANISM: Rattus norvegicus
<220> FEATURE:
<223> OTHER INFORMATION: GGF_4 amino acid sequence -continued

```
<400> SEQUENCE: 27

Pro Leu Pro Ala Val Asn Trp Thr Leu Pro Thr Gly Gly Pro Glu
                 5                  10                  15

Pro Ser Thr Asp Gln Pro Gly Asp Pro Ala Pro Tyr Leu Val Lys
             20                  25                  30

Val His Gln Val Trp Ala Val Lys Ala Gly Gly Leu Lys Lys Asp
             35                  40                  45

Ser Leu Leu Thr Val Arg Leu Asp Thr Trp Gly His Pro Ala Phe
             50                  55                  60

Pro Ser Cys Gly Arg Leu Lys Glu Asp Ser Arg Tyr Ile Phe Phe
             65                  70                  75

Met Glu Pro Asp Ala Asn Ser Ser Gly Arg Ala Pro Pro Ala Phe
             80                  85                  90

Arg Ala Ser Phe Pro Pro Leu Glu Thr Gly Arg Asn Leu Lys Lys
             95                 100                 105

Glu Val Ser Arg Val Leu Cys Lys Arg Cys Ala Leu Pro Pro Arg
            110                 115                 120

Leu Lys Glu Met Lys Ser Gln Glu Ser Ala Ala Gly Ser Lys Leu
            125                 130                 135

Val Leu Arg Cys Glu Thr Ser Ser Glu Tyr Ser Ser Leu Arg Phe
            140                 145                 150

Lys Trp Phe Lys Asn Gly Asn Glu Leu Asn Arg Lys Asn Lys Pro
            155                 160                 165

Glu Asn Ile Lys Ile Gln Lys Lys Pro Gly Lys Ser Glu Leu Arg
            170                 175                 180

Ile Asn Lys Ala Ser Leu Ala Asp Ser Gly Glu Tyr Met Cys Lys
            185                 190                 195

Val Ile Ser Lys Leu Gly Asn Asp Ser Ala Ser Ala Asn Ile Thr
            200                 205                 210

Ile Val Glu Ser Asn Glu Phe Ile Thr Gly Met Pro Ala Ser Thr
            215                 220                 225

Glu Thr Ala Tyr Val Ser Ser Glu Ser Pro Ile Arg Ile Ser Val
            230                 235                 240

Ser Thr Glu Gly Ala Asn Thr Ser Ser Thr Ser Thr Ser Thr
            245                 250                 255

Thr Gly Thr Ser His Leu Ile Lys Cys Ala Glu Lys Glu Lys Thr
            260                 265                 270

Phe Cys Val Asn Gly Gly Glu Cys Phe Thr Val Lys Asp Leu Ser
            275                 280                 285

Asn Pro Ser Arg Tyr Leu Cys Lys Cys Pro Asn Glu Phe Thr Gly
            290                 295                 300

Asp Arg Cys Gln Asn Tyr Val Met Ala Ser Phe Tyr Met Thr Ser
            305                 310                 315

Arg Arg Lys Arg Gln Glu Thr Glu Lys Pro Leu Glu Arg Lys Leu
            320                 325                 330

Asp His Ser Leu Val Lys Glu Ser Lys Ala Glu Glu
            335                 340
```